(12) United States Patent
Lu et al.

(10) Patent No.: US 11,701,054 B2
(45) Date of Patent: Jul. 18, 2023

(54) SYSTEMS AND METHODS FOR MEASURING BEHAVIOR CHANGES OF PROCESSES

(71) Applicants: Ohio State Innovation Foundation, Columbus, OH (US); Adaptive Sensory Technology, Inc., San Diego, CA (US)

(72) Inventors: Zhong-Lin Lu, Dublin, OH (US); Yukai Zhao, Columbus, OH (US); Luis A. Lesmes, San Diego, CA (US)

(73) Assignees: OHIO STATE INNOVATION FOUNDATION, Columbus, OH (US); ADAPTIVE SENSORY TECHNOLOGY, INC., San Diego, CA (US)

( * ) Notice: Subject to any disclaimer, the term of this patent is extended or adjusted under 35 U.S.C. 154(b) by 893 days.

(21) Appl. No.: 16/492,525

(22) PCT Filed: Mar. 12, 2018

(86) PCT No.: PCT/US2018/021944
§ 371 (c)(1),
(2) Date: Sep. 9, 2019

(87) PCT Pub. No.: WO2018/169838
PCT Pub. Date: Sep. 20, 2018

(65) Prior Publication Data
US 2021/0007654 A1    Jan. 14, 2021

Related U.S. Application Data

(60) Provisional application No. 62/470,542, filed on Mar. 13, 2017.

(51) Int. Cl.
*A61B 5/00*     (2006.01)
*G06N 20/00*    (2019.01)
(Continued)

(52) U.S. Cl.
CPC .............. *A61B 5/4005* (2013.01); *A61B 5/16* (2013.01); *A61B 5/4082* (2013.01);
(Continued)

(58) Field of Classification Search
CPC ....... A61B 5/4005; A61B 5/16; A61B 5/4082; A61B 5/4088; A61B 5/4842; A61B 3/14;
(Continued)

(56) References Cited

U.S. PATENT DOCUMENTS 10,026,330 B2 *   7/2018  Burford ................. G09B 5/125
10,546,508 B2 *   1/2020  Quinlan ................. G06F 3/013
(Continued)

OTHER PUBLICATIONS

International Search Report and Written Opinion in International Application No. PCT/US18/21944, dated May 30, 2018 (9 pages).

*Primary Examiner* — Molly Wilburn
(74) *Attorney, Agent, or Firm* — Benesch, Friedlander, Coplan & Aronoff LLP

(57) ABSTRACT

The present disclosure relates to systems and methods for characterizing a behavior change of a process. A behavior model that can include a set of behavior parameters can be generated based on behavior data characterizing a prior behavior change of a process. A stimulus parameter for a performance test can be determined based on the set of behavior parameters. An application of the performance test to the process can be controlled based on the stimulus parameter to provide a measure of behavior change of the process. Response data characterizing one or more responses associated with the process during the performance test can be received. The set of behavior parameters can be updated based on the response data to update the behavior model characterizing the behavior change of the process. In some examples, the behavior model can be evaluated to improve or affect a future behavior performance of the process.

27 Claims, 27 Drawing Sheets

(51) Int. Cl.
*G16H 50/30* (2018.01)
*A61B 5/16* (2006.01)
*G06N 7/00* (2023.01)

(52) U.S. Cl.
CPC .......... *A61B 5/4088* (2013.01); *A61B 5/4842* (2013.01); *G06N 7/005* (2013.01); *G06N 20/00* (2019.01); *G16H 50/30* (2018.01)

(58) Field of Classification Search
CPC ........ A61B 3/063; G06N 7/005; G06N 20/00; G16H 50/30
See application file for complete search history.

(56) References Cited

U.S. PATENT DOCUMENTS

| | | | |
|---|---|---|---|
| 2010/0007851 A1* | 1/2010 | Lu ..................... | A61B 3/028 351/242 |
| 2012/0307204 A1 | 12/2012 | Trachtman | |
| 2013/0176534 A1* | 7/2013 | Frankfort ............ | A61B 3/0025 351/209 |
| 2014/0234826 A1* | 8/2014 | Breznitz ................ | G09B 7/00 434/362 |
| 2017/0256173 A1* | 9/2017 | Burford ................ | G09B 5/125 |
| 2018/0158359 A1* | 6/2018 | Quinlan ................ | G06F 3/013 |
| 2019/0216392 A1* | 7/2019 | Bower ................ | A61B 5/4076 |
| 2021/0007654 A1* | 1/2021 | Lu ....................... | A61B 5/4842 |

* cited by examiner

Table 1. Accuracy and precision of CSF estimates by the qCD

| Time (s) | HWCI | SD | Bias |
|---|---|---|---|
| 10 | 0.1833 | 0.1219 | 0.1384 |
| 20 | 0.1259 | 0.1103 | 0.1226 |
| 50 | 0.0768 | 0.0687 | 0.0818 |
| 100 | 0.0567 | 0.0533 | 0.0555 |
| 200 | 0.0436 | 0.0428 | 0.0403 |
| 300 | 0.0382 | 0.0404 | 0.0381 |

FIG. 22

SYSTEMS AND METHODS FOR MEASURING BEHAVIOR CHANGES OF PROCESSES

CROSS-REFERENCE TO RELATED APPLICATION

This application is a national stage entry of International Patent Application No. PCT/US2018/021944, filed on Mar. 12, 2018, entitled "SYSTEMS AND METHODS FOR MEASURING BEHAVIOR CHANGES OF PROCESSES," which claims the benefit of U.S. Provisional Application No. 62/470,542, filed on Mar. 13, 2017, entitled "SYSTEMS AND METHODS FOR MEASURING BEHAVIOR CHANGES OF PROCESSES," the contents of which are incorporated herein by reference in their entirety.

GOVERNMENT SPONSORSHIP

This invention was made with government support under grant number EY021553 awarded by the National Institute of Health. The government has certain rights in the invention.

TECHNICAL FIELD

This disclosure generally relates to systems and methods for measuring behavior changes of processes. Specifically, this disclosure relates to systems and methods for measuring behavior changes of complex systems, activities and patterns. More particularly, this disclosure relates to systems and methods for measuring behavioral changes of sensory systems.

BACKGROUND

Methodologies exist for measuring behavior changes of processes of complex systems, activities and patterns. For example, a behavior of a sensory system, such as a visual system (e.g., human eye), an auditory system, a somatosensory system, an olfactory system, or a gustatory system, can be evaluated according to a known methodology. Knowledge of a behavioral performance of the visual system (e.g., retinal function) can allow, for instance, a clinician to make diagnoses, monitor disease progression and prescribe appropriate treatments. Visual adaptation describes a process in which the visual system alters its properties, such as sensitivity, in response to changes in the environment. Visual adaptation is the ability of the human visual system to adapt to (e.g., adjust a sensitivity) to various levels of darkness and light (e.g., luminance values). Perceptual sensitivity of the human eye is not constant but changes with time, even varying from one moment to the next. Perceptual learning is improvement of performance in perceptual tasks through training or practice.

The perceptual sensitivity of the visual system can vary along many stimulus dimensions, and can change over a wide range of time scales and time courses. For example, changes in perceptual sensitivity can be characterized not only in a single stimulus dimension, such as a detection threshold in dark adaptation, but also along more complex stimulus dimensions, such as a contrast sensitivity function, which characterizes a sensitivity of the human eye as a function of spatial frequency, or a modulation transfer function, which characterizes the sensitivity of the human eye as a function of a temporal frequency. The time scales of perceptual sensitivity change can vary from seconds or minutes, such as in dark adaptation, to days, months or years, such as in some forms of perceptual learning, disease progression, or treatment monitoring. Auditory sensitivity can also vary along multiple dimensions such as temporal frequency, duration, and change with adaptation or learning. Somatosensory, olfactory, gustatory sensitivity can also vary along multiple dimensions.

Currently parametric and non-parametric methodologies exist for measuring perceptual sensitivity (e.g., luminance threshold, contrast threshold, or feature difference threshold, auditory detection threshold, auditory modulation detection threshold, sensitivity to speech, sensitivity to touch, smell, or taste). For example, a method of constant stimuli (MCS), a type of classical psychophysical methodology, can measure perceptual sensitivity of the visual system of the subject by providing a stimulus that only varies in a single stimulus dimension (e.g., luminance or contrast) while keeping remaining stimulus dimensions fixed (e.g., spatial frequency, temporal frequency, duration, orientation). To measure the perceptual sensitivity as a function of the remaining stimulus dimension characteristics, such as spatial frequency, the MCS has to be repeated for each value (e.g., spatial frequency) on that stimulus dimension. Thus, the MCS is inefficient and takes hundreds or thousands of trials (hours for a single subject) to measure perceptual sensitivity functions, such as a contrast sensitivity function.

A number of adaptive psychophysical methodologies have been developed to provide more efficient measures of perceptual sensitivity relative to classical psychophysical methodologies, such as the MCS. These adaptive methodologies can include non-parametric methodologies for characterizing the perceptual sensitivity. For instance, staircase procedures can be used to converge to single thresholds at desired accuracy levels. More recently, methodologies based on Bayesian adaptive frameworks have been developed to measure a single perceptual sensitivity, sensitivity and slope of a psychometric function, sensitivity and bias parameters in Yes-No tasks or contrast sensitivity functions.

SUMMARY

In an example, a computer-implemented method can include receiving behavior data characterizing a prior behavior change of a process, generating a behavior model that can include a set of behavior parameters based on the behavior data. determining one or more stimulus parameters for a performance test based on the one or more behavior parameters, controlling an application of the performance test to the process based on the one or more stimulus parameters to provide a measure of behavior change of the process, receiving response data characterizing one or more responses associated with the process during the performance test and updating the set of behavior parameters based on the response data to update the behavior model characterizing the behavior change of the process.

In another example, a system can include a non-transitory memory to store machine-readable instructions and data, and a processor to access the memory and execute the machine-readable instructions. The machine-readable instructions can cause the processor to: generate a behavior model that can include a set of behavior parameters based on behavior data characterizing a prior behavior change of a sensory system of a subject, control an application of a sensory test to the sensory system based on one or more stimulus parameters to provide a measure of behavior change of the sensory system, receive response data characterizing one or more responses associated with the sensory system during the sensory test, update the set of behavior parameters based on the response data to update the behavior model characterizing the behavior change of the sensory system according to a stopping criterion, evaluate the behavior model after a given sensory test, and generate behavior adjustment data based on the evaluation. The behavior adjustment data can include information for improving or affecting a future behavior performance of the sensory system.

In another example, a system can include a non-transitory memory to store machine-readable instructions and data, and a processor to access the memory and execute the machine-readable instructions. The machine-readable instructions can cause the processor to: receive behavior data characterizing a prior behavior change of a visual system of one of a human and an animal and generate a behavior model that can include a set of behavior parameters based on the behavior data. The behavior model can correspond to a perceptual sensitivity function characterizing a time course of perceptual sensitivity change of the visual system. The machine-readable instructions can further cause the processor to: determine one or more stimulus parameters for a vision test based on the one or more behavior parameters, control an application of the vision test to the visual system based on the one or more stimulus parameters to provide a measure of behavior change of the visual system, receive response data characterizing one or more responses associated with the vision system during the vision test, update the set of behavior parameters based on the response data to update the behavior model according to a stopping criterion and repeat the determining, the controlling, the receiving and the updating over a plurality of vision tests to update the behavior model characterizing the time course of perceptual sensitivity change of the visual system.

This Summary is provided merely for purposes of summarizing some example embodiments to provide a basic understanding of some aspects of the disclosure. Accordingly, it will be appreciated that the above described example embodiments are merely examples and should not be construed to narrow the scope or spirit of the disclosure in any way. Other embodiments, aspects, and advantages of various disclosed embodiments will become apparent from the following detailed description taken in conjunction with the accompanying drawings which illustrate, by way of example, the principles of the described embodiments.

BRIEF DESCRIPTION OF THE DRAWINGS

Features, objects and advantages other than those set forth above will become more readily apparent when consideration is given to the detailed description below. Such detailed description makes reference to the following drawings.

FIG. 22 depicts Table 1 summarizing an average absolute bias, an average 68.2% HWCI and an average standard deviation of the simulations of the quick CSF change detection method.

DETAILED DESCRIPTION

Figure 1:
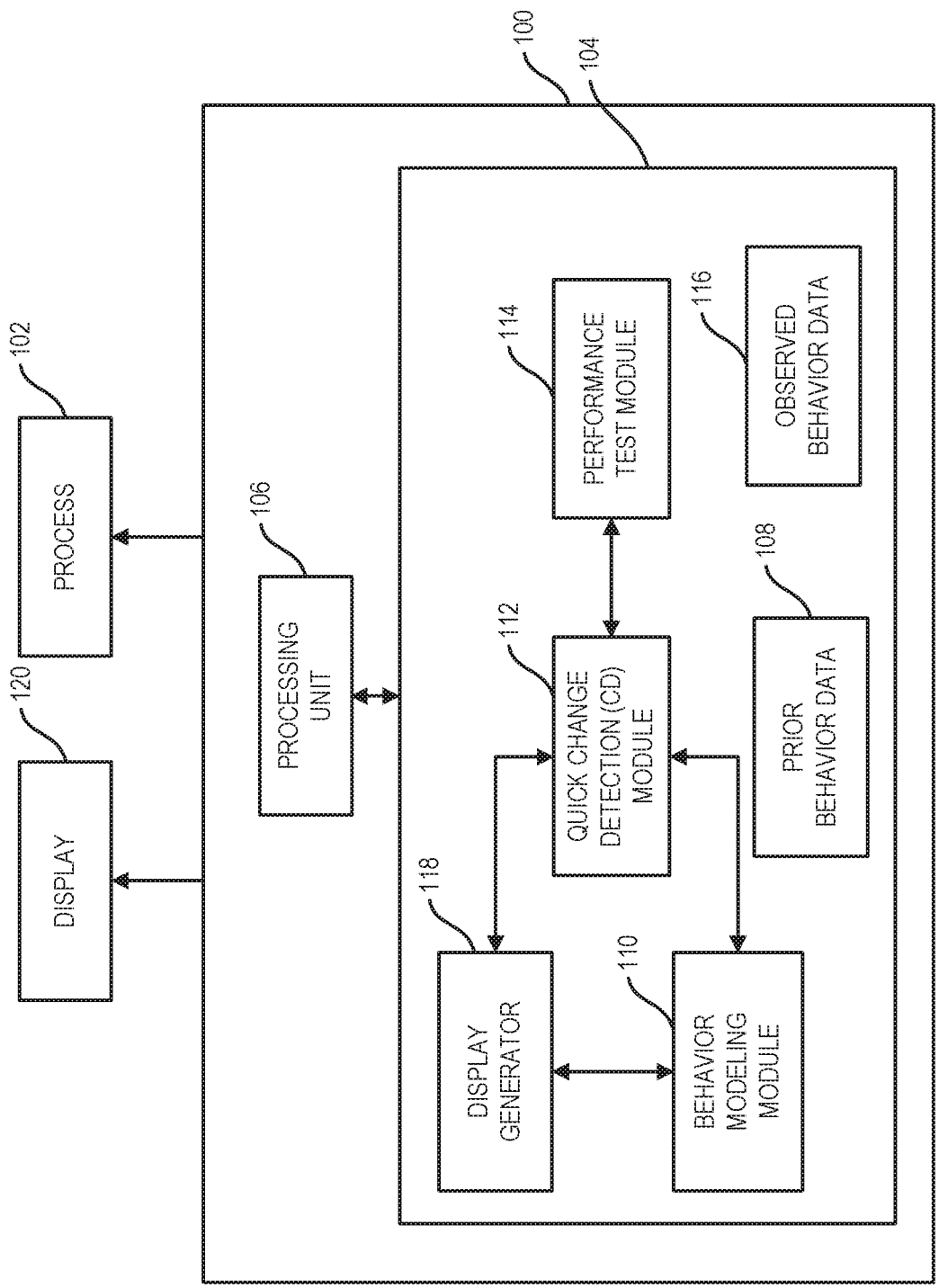
FIG. 1 depicts an example of a behavior analysis system (BAS) for measuring behavior changes of a process.

The present disclosure relates to systems and methods for measuring behavior changes of processes, including perceptual sensitivity. According to the systems and methods described herein, a given performance test can be applied to a corresponding process to provide a measure of behavioral performance of the process. The given performance test can include, but not limited to, a detection task (e.g., whether a light, sound, taste, touch, or smell is present or not), an identification task (e.g., which one of visual patterns, objects, voices, tastes, smells, or touches is presented), a discrimination task (e.g., whether the stimulus sequence AB or BA is presented), a magnitude estimation task (e.g., how bright is the light, how loud is a voice, etc.), an eye movement, a physiological response to a sensory stimulus (e.g., electroencephalogram (EEG), skin conductance, functional magnetic resonance imaging (fMRI), magnetoencephalogram (MEG), heart rate, blood pressure, etc.), structural changes (e.g., MRI, CT, OCT, fundus images, etc.), and/or a response time task (e.g., how fast can one respond to a sensory stimulus). Some examples as described herein, the measured behavioral performance can be evaluated to control an administration of a therapy, treatment, and the like. Additionally, or alternatively, the measured behavioral performance can be evaluated to improve (or affect) a future behavioral performance of the process (e.g., accuracy, quality, functionality, etc.). Each performance test can be administered sequentially over a time interval or between events. In examples were the performance test is a vision test, the vision test can be applied over a single time interval (e.g., during a single sitting of the vision test) or between medical treatments. The systems and methods described herein can precisely, accurately, and efficiently characterize the behavior change of the process based on the given performance test. The term "behavior" as used herein, can generally refers to any dynamic type or form of an action, change, outcome or result, produced by a process. The advantages and technical improvements that the systems and methods described herein have over existing techniques for measuring behavioral changes of processes will become more readily apparent and better appreciated by the examples described herein.

In some examples, according to the systems and methods described herein, a performance test can be applied to provide a measure of perceptual sensitivity change for the subject. Methodologies exist for measuring perceptual sensitivity by repeating measurements at multiple time points. However, existing methodologies are prone to biasing and imprecise estimates since these methodologies only characterize an average of the perceptual sensitivity over a plurality of time-intervals (or tests). Existing methodologies do not consider how perceptual sensitivity behaves within each of the plurality of time-intervals. By using the systems and methods and described herein, precisely, perceptual sensitivity change can be accurately, and efficiently characterized based on the performance test. As such, the systems and methods described herein address the technical challenges associated with existing methodologies for measuring perceptual sensitivity change.

Aspects of the present disclosure are described herein in context of measuring behavior changes of a physiological process, such as visual sensitivity of a visual system. However, the present disclosure should not be construed and/or limited to only measuring behavioral changes of visual sensitivity. The present disclosure can provide a measure of behavioral performance of other processes, including, but not limited to, a psychophysical process (e.g., contrast sensitivity), a physiological process, an activity, a pattern, and combinations thereof. Thus, the present disclosure can provide a measure of behavioral performance of complex systems, including, but not limited to, the visual system, an auditory system, a somatosensory system, a gustatory system, an olfactory system and a physiological system. The physiological system can include, but not limited to, lungs, a heart, and a brain.

In some examples, the present disclosure described herein can be extended to measuring behavior changes of processes, including, but not limited to, physiological (e.g., EEG, MEG, fMRI, functional near-infrared spectroscopy (fNIR), skin conductance, a heart rate and a release of a chemical from a body of the human), perceptual (e.g., vision, audition, taste, tactile, olfaction, proprioception), cognitive (e.g., attention, memory, language, learning, executive function, social cognition, sematic cognition, numerical cognition), disease prognosis and its treatment evaluation (e.g., maculopathy such as age-related macular degeneration, inherited retinal disorders, retinal detachment, central serous retinopathy, diabetic retinopathy, diabetic macular edema, choroidal neovascularization, amblyopia, myopia, dyslexia, schizophrenia, neurodegenerative disorders such as Alzheimer's disease, Amyotrophic lateral sclerosis, multiple sclerosis, Huntington's disease, Parkinson's disease), contextual and environmental.

The present disclosure described herein can further be extended to measuring behavior changes of derived information, analytical status information, contextual information, continuous information, discrete information, time series information, event information, raw information, processed information, metadata, third party information, physiological state information, psychological state information, survey information, medical information, genetic information, environmental information, transactional information, economic information, socioeconomic information, demographic information, psychographic information, sensed information, continuously monitored information, manually entered information, inputted information, continuous information, real-time information, pattern information, such as traffic pattern information (e.g., a number of cars, road designs, traffic signals car crash rate, etc.), traffic flow information (e.g., a possibility of traffic jam), popularity information (e.g., a popularity of a movie) and sales information (e.g., box office sales of the movie).

FIG. 1 depicts an example of a behavior measuring system (BMS) 100 for measuring behavior changes of a process 102. The BMS 100 can be implemented on a computer, such as a laptop computer, a desktop computer, a server, a tablet computer, a workstation, or the like. The BMS 100 can include memory 104 for storing data and machine-readable instructions. The memory 104 can be implemented, for example, as a non-transitory computer storage medium, such as volatile memory (e.g., random access memory), non-volatile memory (e.g., a hard disk drive, a solid-state drive, flash memory or the like) or a combination thereof.

The BMS 100 can also include a processing unit 106 to access the memory 104 and execute the machine-readable instructions stored in the memory 104. The processing unit 106 could be implemented, for example, as one or more processor cores. In the present example, although the components of the BMS 100 are illustrated as being implemented on the same system, in other examples, the different components could be distributed across different systems and communicate, for example, over a network. The processing unit 106 can be configured to receive prior behavior data 108 for the process 102. The prior behavior data 108 can correspond to a prior behavior change of the process 102 over a given time interval. The processing unit 106 can be configured to store the prior behavior data 108 in the memory 104.

The BMS 100 can include a behavior modeling module 110. The behavior modeling module 110 can be programmed to generate a behavior model based on the prior behavior data 108. The behavior model can provide an estimate of the behavior change of the process 102 (e.g., over a period of time, or between events). Thus, the behavior model can characterize the behavioral performance of the process 102. The behavior model can include parametric information that can be quantified in one of joint distribution of parameters, product of subsets of joint distributions of parameters with known independence, fixed discrete grid with pre-determined values of each parameter, dynamic grid, forms other than grid, such as particle filters, parameters of individuals and/or of groups and parameters from competing models. The behavior model can include a set of behavior parameters. The set of behavior parameters can characterize a complete estimate of the behavior change of the process 102. Initially, the set of behavior parameters can be defined to provide prior estimate values based on the prior behavior data 108. The prior estimate values can be updated based on future behavior data associated with the process 102 in accordance to the methods described herein to refine the behavior model to provide a more accurate behavior change estimate of the process 102.

The BMS 100 can include a quick change detection (qCD) module 112. The qCD module 112 can be programmed to update the set of behavior parameters of the behavior model (e.g., update the estimate values) based on future behavior data. The future behavior data can be generated in response to a plurality of performance tests that can be applied to the process 102. The qCD module 112 can be programmed to update the set of behavior parameters of the behavior model according to a Bayesian inference. The qCD module 112 can be programmed to start with a prior probability distribution of each combination of behavior parameters of the set of behavior parameters and update the probability distribution of the behavior parameters according to future behavior data generated in response to each application of the performance test to the process 102.

The qCD module 112 can be programmed to characterize each behavior parameter of the set of behavior parameters by a probability density function to represent a relative likelihood that a value of a given parameter would equal that sample. In some examples, each of the prior probability density functions is one of a uniform density function, a hyperbolic probability density function and a combination thereof. Additionally, or alternatively, the behavior model can be one of parametric and non-parametric. The non-parametric (e.g., Bayesian) methods include, but are not limited to, Dirichlet process (DP) models, Polya trees, wavelet based models, neural network models, and spline regression. In an example, the qCD module 112 can be programmed to characterize each behavior parameter of the behavior model by an n-dimensional joint probability distribution in a parameter space, wherein "n" is an integer greater than one. The parameter space can represent all possible variations of the behavior model. For example, if the behavior model is an exponential decay function, the parameter space can represent all possible variations of the exponential decay function.

The qCD module 112 can be programmed to determine one or more test parameters for each application of the performance test to the process 102. The performance test can be applied to provide a measure of behavior performance of the process 102. The BMS 100 can include a performance test module 114. The performance test module 114 can be programmed to control an application of the performance test to the process 102 based on the one or more determined test parameters. The performance test module 114 can be programmed to receive observed behavior data 116 characterizing one or more observed behavior performances of the process 102 during the performance test. In an example, the one or more responses can be provided by an observer (not shown in FIG. 1) associated with the process 102. The observer can include, but not limited to, a human, an animal, an artificial intelligence system, or a monitoring system. Alternatively, the one or more responses can be provided by the process 102 in response to the performance test. The performance test module 114 can be programmed to store the observed behavior data 116 in the memory 104.

The qCD module 112 can be programmed, after each application of the performance test, to update the prior distribution of the joint probability density functions for each combination of the set of behavior parameters of the behavior model to a posterior distribution based on the observed behavior data 116 by a Bayes' rule:

$$p_{t_n}(\vec{\theta} \mid r_n, x_n) = \frac{p_{t_n}(r_n \mid \vec{\theta}, x_n) p_{t_n}(\vec{\theta})}{p_{t_n}(r_n \mid x_n)}, \quad (1)$$

$$p_{t_n}(r_n \mid x_n) = \Sigma_{\vec{\theta}} p_{t_n}(r_n \mid \vec{\theta}, x_n) p_{t_n}(\vec{\theta}), \quad (2)$$

wherein $\vec{\theta}$ represents parameters of the behavior model, $p_{t_n}(\vec{\theta})$ is the prior probability density function of $\vec{\theta}$ of a given application of the performance test, $p_{t_n}(r_n \mid \vec{\theta}, x_n)$ is a likelihood of observing a response (e.g., a desired response) given $\vec{\theta}$ and stimulus parameter $x_n$, $r_n$ is the response of the process 102 in the given application of the performance test, $p_{t_n}(\vec{\theta} \mid r_n, x_n)$ is the posterior distribution of $\vec{\theta}$ after the given application of the performance test, and $\Sigma_{\vec{\theta}}$ is the summation over all dimensions in the parameter space $\vec{\theta}$. The best estimate of the behavior model can be a mean of the set of behavior parameters from the posterior distribution after an $n^{th}$ application of the performance test, wherein "n" is greater than two.

The qCD module 112 can be programmed to update the probability density function for each combination of the behavior parameters of the behavior model by determining one or more corresponding stimulus parameters for each application of the performance test of a plurality of application of the performance test. The qCD module 112 can be programmed to control each application of the performance test to the process based on the corresponding stimulus parameter(s). The qCD module 112 can be programmed to refine the prior probability density function for each combination of the behavior parameters of the behavior model based on the response data of the given application of the performance test to generate the posterior probability density function for each combination of the behavior parameters of the behavior model. The posterior probability density function for each combination of the behavior parameters of the behavior model can be used by the qCD module 112 to determine the corresponding parameter(s) for the subsequent application of the performance test to the process 102.

The qCD module 112 can be programmed to select one or more appropriate test stimulus parameters for the performance test among a plurality of test parameters in a stimulus parameter space that maximizes an expected information gain about the set of behavior parameters of the behavior model. In some examples, the qCD module 112 can be programmed to perform a one-step ahead search for a minimum or near minimum entropy. To determine the appropriate test parameter(s) for an $n^{th}$ application of the performance test, the qCD module 112 can be programmed to predict a processes response to every possible test parameter(s) in the $n^{th}$ application of the performance test based on the current estimated posterior probability density functions of the set of parameters. The qCD module 112 can be programmed to compute an expected entropy of the posterior distribution of the set of parameters for each possible test parameter(s). The test parameter(s) among the plurality of test parameters with one of the least expected entropies is selected by the qCD module 112 for the $n^{th}$ application of the performance test. This is equivalent to improving the expected information gain, quantified as the entropy change between the prior and the posterior.

The BMS 100 can be programmed for a plurality of application of the performance test to the process 102 to update the parameters of the probability density functions for each of the behavior parameters of the behavior model based on the observed behavior data 116 generated during each application of the performance test to the process 102 according to the Bayes' rule, and thus update the behavior model to provide a more accurate representation of the behavior performance of the process 102. The BMS 100 can be programmed to refine the behavior model according to a stopping criterion. In some examples, the stopping criterion is a given number of application of the behavior test to the process 102. In other examples, the stopping criterion is a precision level for a defined objective. By refining the behavior parameters of the behavior model according to the Bayes' rule based the performance test data 116 obtained during each application of the performance test to the process 102, the behavior model can be dynamically updated to more precisely, accurately and efficiently represent the behavior change of the process 102.

In some examples, the qCD module 112 can be programmed to communicate with a display generator 118 stored in the memory 104. The display generator 118 can be programmed to provide data to a display 120. The data can include a graphical representation of the behavior model. The display generator 118 can be programmed to provide updated versions of the behavior model during each update of the behavior model (e.g., updating of the behavior parameters of the behavior model) following each performance test. The display 120 can be configured to render the graphical representation of the behavior model. Thus, the BMS 100 can be configured to accurately, precisely and efficiently measure a behavior change of the process 102.

Additionally, or alternatively, the qCD module 112 can be programmed to evaluate the behavior model to improve (or affect) a future behavioral performance of the process 102. The improvement (or affect) can include, but not limited to, an accuracy of the process, a quality of the process, a functionality of the process (e.g., by adjusting parameters and/or variables associated with the process), and combination thereof. The qCD module 112 can be programmed to generate behavior adjustment data based on the evaluation. The behavior adjustment data can be used, for example, by the BMS 112, an external system (not shown in FIG. 1), apparatus, device, or a human, to improve (or affect) the process 102. Accordingly, the BMS 100 can be configured relative to the process 102 and function as a feedback mechanism for improving (or affecting) the behavioral performance for the process 102.

Figure 2:
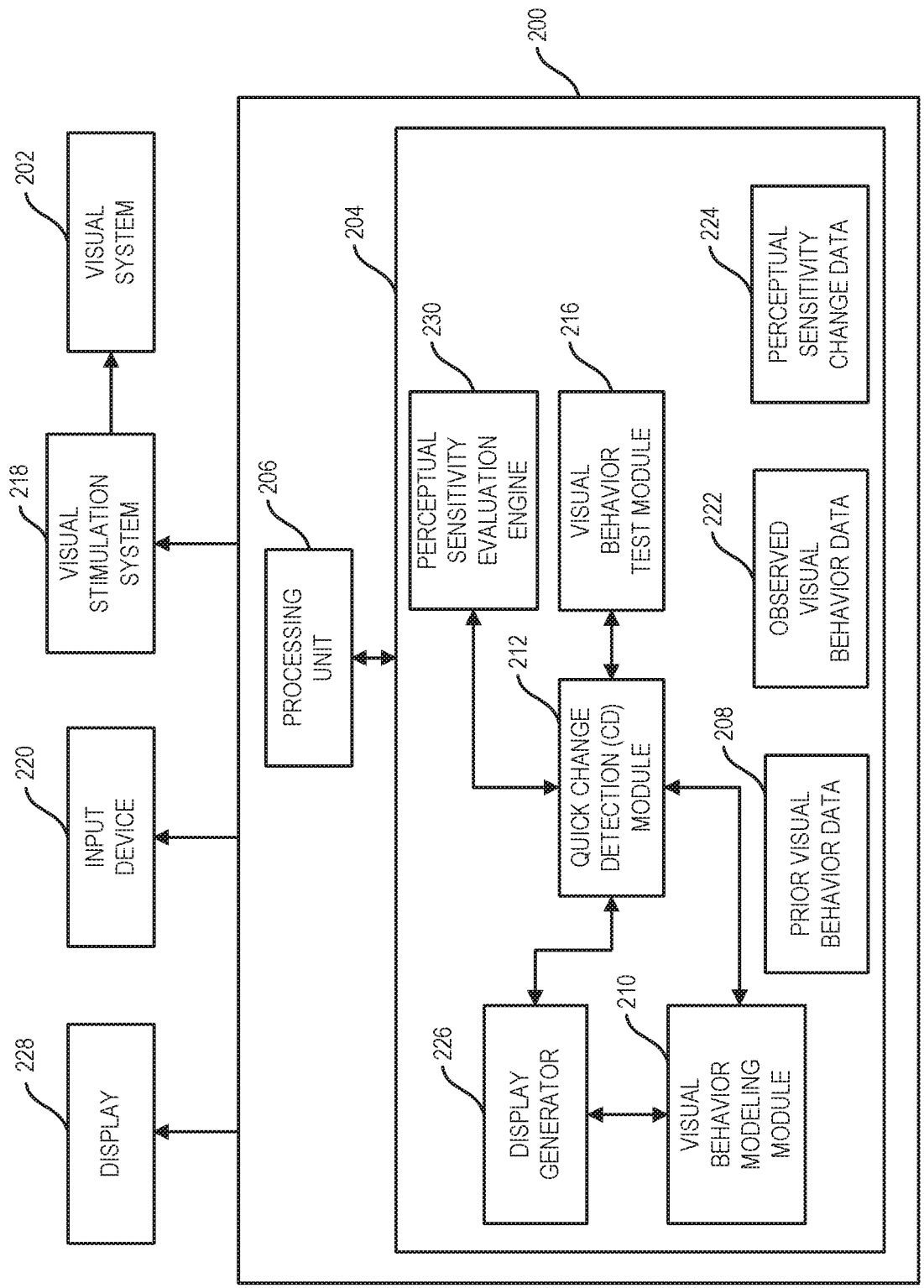
FIG. 2 depicts an example of a BAS for measuring a time course of perceptual sensitivity change of a visual system.

FIG. 2 depicts an example of a behavior measuring system (BMS) 200 for measuring time course of perceptual sensitivity changes of a visual system 202 of an observer. The observer can include one of a human, an artificial intelligence system, and an animal. The BMS 200 can be configured to characterize a time course of perceptual sensitivity changes of the visual system 202 of the observer. Such characterization can provide a quantitative measure of retinal function of the visual system 202, for example, in dark adaptation. Additionally or alternatively, the BMS 200 can be configured to characterize a time course of contrast sensitivity function (CSF) changes of the visual system 202, as described herein.

In some examples, the BMS 200 can be configured substantially similar to the BMS 100, as illustrated in FIG. 1. The BMS 200 can be implemented on a computer, such as a laptop computer, a desktop computer, a server, a tablet computer, a workstation or the like. The BMS 200 can include memory 204 for storing data and machine-readable instructions. The memory 204 can be implemented, for example, as a non-transitory computer storage medium, such as volatile memory (e.g., random access memory), non-volatile memory (e.g., a hard disk drive, a solid-state drive, flash memory or the like) or a combination thereof.

The BMS 200 can also include a processing unit 206 to access the memory 204 and execute the machine-readable instructions stored in the memory 204. The processing unit 206 could be implemented, for example, as one or more processor cores. In the present example, although the components of the BMS 200 are illustrated as being implemented on the same system, in other examples, the different components could be distributed across different systems and communicate, for example, over a network. The processing unit 206 can receive and store in the memory 204 prior visual behavior data 208. The prior visual behavior data 208 can corresponds to a prior measured time course of behavior change of the visual system 202. For example, the prior visual behavior data 208 can correspond to a prior measured time course of perceptual sensitivity changes (e.g., luminance thresholds) in dark adaptation. The term "dark adaptation" as used herein can refer to how the visual system (e.g., an eye) recovers sensitivity in the dark following exposure to light. In an example, the prior visual behavior data 208 can be generated based on a population of subjects. The subjects can include a human, an animal or a combination thereof.

The BMS 200 can be configured to employ a visual behavior modeling module 210 and a quick change detection (qCD) module 212. In some examples, the visual behavior modeling module 210 and the qCD module 212 can be implemented substantially similar to the behavior modeling module 110 and the qCD module 112, as illustrated in FIG. 1. The qCD module 212 can be programmed to control the visual behavior modeling module 210 to generate a perceptual sensitivity model based on the prior visual behavior data 208 to provide an estimate of a time course of a behavior change of the visual system 202 (e.g., perceptual sensitivity change). The perceptual sensitivity model can be one of a parametric, non-parametric model and a combination thereof. The perceptual sensitivity model can have any functional form, including parametric, non-parametric or a combination thereof.

The perceptual sensitivity model can include a set of behavior parameters. The set of behavior parameters can characterize a complete estimate of the time course of a behavior performance of the visual system 202. Thus, the set of behavior parameters can define the perceptual sensitivity model. In an example, the perceptual sensitivity model can include a luminance threshold decay function. The luminance threshold decay function can be described by the following exponential function:

$$\alpha(\vec{\theta}, t) = \alpha_0 + \alpha_1 \exp(-t/\tau), \quad (3)$$

where $\vec{\theta} = (\theta_1, \theta_2, \theta_3) = (\alpha_0, \alpha_1, \tau)$ can be the set of parameters of the luminance threshold decay function, t can be an amount of time elapsed since a start of a test measured in one of seconds and minutes, $\alpha(\vec{\theta}, t)$ can be a luminance threshold corresponding to a sensitivity index of d'=1.5, $\alpha_0$ can be an asymptotic threshold parameter, $\alpha_0 + \alpha_1$ can be a threshold parameter at t=0 second, and r can be a time constant parameter of the exponential function.

The luminance threshold decay function can be measured at a given performance level, indexed by d', a statistic of signal detection theory that can provide a separation between means of a signal and noise distribution, compared against a standard deviation of the noise distribution. The functional form can assume a different formula (e.g., a power function) that can have general decaying characteristics. Initially, the set of behavior parameters of the luminance threshold decay function can be defined to provide prior estimate values based on the prior visual behavior data 208. The prior estimate values can be updated based on future visual behavior data associated with the visual system 202 in accordance to the methods described herein to refine the behavior model to provide a more accurate estimate of the time course of the behavior change of the visual system 202.

The BMS 200 can be configured to employ the qCD module 212 to update the set of behavior parameters of the luminance threshold decay function (e.g., update the estimate values) to refine the luminance threshold decay function based on observed visual behavior data 214 for the visual system 202 generated during each vision test applied to the visual system 202. In some examples, the vision test is a signal detection test. Thus, in some examples, the vision test can include an eight-alternative-forced-choice task (8AFC). In other examples, the vision test is a sensory test. The BMS 200 can be programmed to refine the luminance threshold decay function to provide a more accurate approximation of the time course of perceptual sensitivity change by updating the set of behavior parameters of the luminance threshold decay function based on the observed visual behavior data 214 from each application of the vision test to the visual system 202. The qCD module 212 can be programmed to update the set of behavior parameters of the luminance threshold decay function using a Bayesian inference. The qCD module 212 can be programmed to start with a prior probability distribution of each behavior parameter of the set of behavior parameters and update the probability distribution of each of the behavior parameters based on the observed data generated during each application of the vision test to the visual system 202.

The qCD module 212 can be programmed to characterize the set of behavior parameters by a probability density function, $p(\vec{\theta})$, to represent a relative likelihood that the value of a given parameter would equal that sample. In some examples, each of the prior probability density functions, $p(\vec{\theta})$, are one of a uniform density function, a hyperbolic probability density function and a combination thereof. Additionally, or alternatively, the qCD module 212 can be programmed to characterize each behavior parameter of the behavior model by a three-dimensional joint probability distribution in a parameter space. The qCD module 212 can be programmed to define a broad joint prior distribution $p_0(\vec{\theta})$ (uniform or hyperbolic) in a three-dimensional parameter space $\vec{\theta} = (\alpha_0, \alpha_1, \tau)$. The parameter space can represent all possible variations of the luminance threshold decay function.

The qCD module 212 can be programmed to determine a stimulus parameter x for each application of the vision test. The determined stimulus parameter can include a luminance level corresponding to a given luminance intensity value measured in candela per square meter ($cd/m^2$). The vision test can be performed according to the stimulus parameter relative to the visual system 202. The vision test can be performed to provide a measure of perceptual sensitivity change of the visual system 202. The qCD module 212 can be programmed to provide the determined stimulus parameter to a visual behavior test module 216.

The visual behavior test module 216 can be programmed to control a visual stimulation system 218 to perform the vision test on the visual system 202 based on the determined stimulus parameter. The visual behavior test module 216 can apply the vision test according to the determined stimulus parameter to the visual system 202 by controlling the visual stimulation system 218. Thus, the visual behavior test module 216 can be programmed to control the visual stimulation system 218 to expose the visual system 202 to light having an intensity value specified by the stimulus parameter.

During each administration of the vision test to the visual system 202, the observer can provide one or more responses $r_n$, based on stimulus parameter x. The one or more responses $r_n$, can include information characterizing a stimulus and/or information related to the stimulus. The subject can provide the one or more responses $r_n$, via an input device 220 during the vision test. The input device 220 can include an audio input device, such as a microphone, or the like. Additionally, or alternatively, the input device can include a keyboard, a mouse, an eye tracker or the like. The input device 220 can be configured to generate observed visual behavior data 222 based on the one or more responses provided by the observer to the input device 220 during the vision test. The observed visual behavior data 222 can be stored in the memory 204. In an example, the one or more response can include one of an indication that the light was detected, the light was not detected and a combination thereof.

The qCD module 212 can be programmed, after each application of the vision test, to update the prior distribution of the probability density function of the set of behavior parameters of the luminance threshold decay function to a posterior distribution based on the vision test data 214 by a Bayes' rule:

$$p_{t_n}(\vec{\theta} \mid r_n, x_n) = \frac{p_{t_n}(r_n \mid \vec{\theta}, x_n) p_{t_n}(\vec{\theta})}{p_{t_n}(r_n \mid x_n)}, \quad (4)$$

$$p_{t_n}(r_n \mid x_n) = \Sigma_{\vec{\theta}} p_{t_n}(r_n \mid \vec{\theta}, x_n) p_{t_n}(\vec{\theta}), \quad (5)$$

wherein $\vec{\theta}$ represents parameters of the luminance threshold decay function, $p_{t_n}(\vec{\theta})$ is the prior probability density function of $\vec{\theta}$ of a previous application of the vision test, $p_{t_n}(r_n \mid \vec{\theta}, x_n)$ is a likelihood of observing a response (e.g., correct or incorrect) given $\vec{\theta}$ and stimulus $x_n$, $r_n$ is the observer's response in a subsequent application of the vision test, $p_{t_n}(\vec{\theta} \mid r_n, x_n)$ is the posterior distribution of B after the subsequent application of the vision test, and $\sigma_{\vec{\theta}}$ is the summation over the three-dimensional parameter space, that is, $\Sigma_{\vec{\theta}} = \Sigma_{\alpha_0} \Sigma_{\alpha_1} \Sigma_{\tau}$. Thus, a given observer's response $r_n$ to a stimulus with luminance x presented at time t(n) in a $n^{th}$ test (e.g., trial), the prior distribution $p_{t_n}(\vec{\theta})$ can be updated to the posterior distribution $p_{t_n}(\vec{\theta} \mid r_n, x_n)$ by the Bayes' rule.

The qCD module 212 can be programmed to use the posterior distribution of $n^{th}$ test as the prior of $n+1^{th}$ test:

$$p_{t_{n+1}}(\vec{\theta}) = p_{t_n}(\vec{\theta} \mid r_n, x_n). \quad (6)$$

The qCD module 212 can be programmed to compute marginal posterior distributions of the parameters via a summation:

$$p_{t_n}(\alpha_0 \mid r_n, x_n) = \Sigma_{\alpha_1} \Sigma_{\tau} p_{t_n}(\vec{\theta} \mid r_n, x_n), \quad (7)$$

$$p_{t_n}(\alpha_1 \mid r_n, x_n) = \Sigma_{\alpha_0} \Sigma_{\tau} p_{t_n}(\vec{\theta} \mid r_n, x_n), \quad (8)$$

$$p_{t_n}(\tau \mid r_n, x_n) = \Sigma_{\alpha_0} \Sigma_{\alpha_1} p_{t_n}(\vec{\theta} \mid r_n, x_n). \quad (9)$$

The expected mean of the marginal posterior distributions can be the estimates of the parameters of the exponential decay function after $n^{th}$ test:

$$\bar{\theta}_{a,n} = \Sigma_{\theta_a} \theta_a \cdot p_{t_n}(\theta_a \mid r_n, x_n), \quad (10)$$

where $\theta_a = \alpha_0$, $\alpha_1$, and $\tau$, for a=1, 2 and 3.

To determine $p_{t_n}(r_n \mid \vec{\theta}, x_n)$, the likelihood of observing a correct and incorrect response given $\vec{\theta}$, the qCD module 212 can be programmed to determine a probability correct p(r=1) psychometric function according to a Weibull function:

$$p'_t(r = 1 \mid \vec{\theta}, x) = g + (1-g)\left(1 - \exp\left(-\left(\frac{x}{\alpha_w(\vec{\theta}, t)}\right)^\gamma\right)\right), \quad (11)$$

$$p_t(r = 1 \mid \vec{\theta}, x) = (1-\lambda) p'_t(r = 1 \mid \vec{\theta}, x) + \lambda g, \quad (12)$$

where the subscript t is time, r is the response (1 for correct, 0 for incorrect), x is the luminance of the stimulus, g=0.125 is a guessing rate of a given AFC task, in an example, the given AFC is an 8AFC, γ=3.8959 is the slope of the psychometric function, λ=0.04 is the lapse rate and x is the stimulus luminance.

$\alpha_w(\vec{\theta}, t)$ is a threshold at time t given parameter $\vec{\theta}$:

$$\log_{10} \alpha_w(\vec{\theta}, t) = \log_{10}(\alpha(\vec{\theta}, t)) - \frac{1}{\gamma} \log_{10}\left(\log\left(\frac{1-g}{1-p_{1.5}}\right)\right), \quad (13)$$

where $p_{1.5} = 0.553$ is the probability correct when d'=1.5 in the 8AFC task. Therefore, $p_t(r=1 \mid \vec{\theta}, x)$ is the observed probability of a correct response (r=1) at time t since the beginning of the dark adaptation, conditioned on parameters $\vec{\theta}$ and stimulus luminance x.

The probability of an incorrect response (r=0) is:

$$p_t(r=0 \mid \vec{\theta}, x) = 1 - p_t(r=1 \mid \vec{\theta}, x). \quad (14)$$

The qCD module 212 can be programmed to determine a given stimulus parameter x for each application of the vision test to the visual system 202. The qCD module 212 can be programmed to select an appropriate stimulus parameter x among a plurality of stimulus parameters x in a one-dimension stimulus luminance space X that can cover all possible luminance x∈X that maximizes an expected information gain about the set of behavior parameters of the luminance threshold decay function. In an example, the qCD module 212 can be programmed to perform a one-step ahead search for minimum or near minimum entropy.

To determine given stimulus parameter x for an $n^{th}$ application of the vision test, the qCD module 212 can be programmed to predict the visual system's 202 response to every possible stimulus parameter x in the $n^{th}$ application of the vision test based on the current estimated posterior probability density functions of the set of parameters. The qCD module 212 can be programmed to compute the expected posterior distribution of the set of parameters for each possible stimulus parameter. The stimulus parameter x among the plurality of stimulus parameters x with one of the least expected entropies is selected by the qCD module 212 for the $n^{th}$ application of the vision test. This is equivalent to improving the expected information gain, quantified as the entropy change between the prior and the posterior. In an example, the stimulus parameter x to be presented in the next vision test is randomly picked among the plurality of stimulus parameters x, for example with a top 10% of an expected information gain. The expected information gain of stimulus x can be defined as $I_t(x)$:

$$I_t(x) = h(\Sigma_{\vec{\theta}} p_t(\vec{\theta}) p_t(r=1 \mid \vec{\theta}, x)) - \Sigma_{\vec{\theta}} p_t(\vec{\theta}) h(p_t(r=1 \mid \vec{\theta}, x)), \quad (15)$$

$$h(p) = p \log(p) - (1-p) \log(1-p). \quad (16)$$

The BMS 200 can be programmed for a plurality of application of the vision test to the visual system 202 to update the parameters of the probability density functions of the behavior parameters of the luminance threshold decay function. The BMS 200 can update the parameters based on the observed visual behavior data 214 received by the visual behavior test module 216 during each application of the vision test to the visual system 202 by the visual stimulation system 222 according to the Bayes' rule. The BMS 200 can update the luminance threshold decay function to provide a more accurate representation of the time course of perceptual sensitivity change of the visual system 202. The BMS 200 can be programmed to update the luminance threshold decay function according to a stopping criterion. In an example the stopping criterion is a given number of application of the vision test to the visual system 202. In another example, the stopping criterion is a precision level fora defined objective, such as an average credible interval of less or equal to 0.1 log 10 units for the estimated thresholds. Accordingly, by refining the behavior parameters of the probability density, $p(\vec{\theta})$, for the behavior parameters of the luminance threshold decay function based vision test response behavior data 214 received during each application of the vision test according to the Bayes' rule, the time course of perceptual sensitivity change of the visual system 202 can be precisely, accurately and efficiently measured.

The qCD module 212 can further be programmed to generate perceptual sensitivity change data 224. The perceptual sensitivity data 224 can be stored in the memory 224 and characterize the time course of perceptual sensitivity change of the visual system 202. The qCD module 212 can be programmed to communicate with a display generator 226 stored in the memory 204 of the BMS 200. The display generator 226 can be programmed to generate display data based on the perceptual sensitivity change data 224. The display data can be provided to a display and the display can render the display data on the display, which can include a graphical representation the time course of perceptual sensitivity change of the visual system 202. Accordingly, the BMS 200 can be configured to accurately, precisely and efficiently measure the time course of perceptual sensitivity change of the visual system 202.

Additionally or alternatively, the BMS 200 can include a perceptual sensitivity evaluation engine (PSEE) 230. The PSEE 230 can be in communication with the qCD module 212. The PSEE 230 can be programmed to receive the perceptual sensitivity change data 224. The PSEE 230 can be programmed to evaluate the perceptual sensitivity change data 224. The PSEE 230 can be programmed to evaluate the perceptual sensitivity change data 224 to make diagnostics, monitor a disease progression and determine an optimal treatment for a disease, such as a maculopathy of the visual system 202, which includes, but is not limited to, age-related macular degeneration (AMD), inherited retinal disorders, retinal detachment, central serous retinopathy, diabetic retinopathy, diabetic macular edema, and choroidal neovascularization. As such, the BMS 200 can be configured to improve (or affect) the behavioral performance of the visual system 202.

In some examples, the PSEE 230 can be programmed to evaluate the perceptual sensitivity change data 224 determine if the patient needs treatment and if yes, the appropriate type, dose, and frequency of the treatment. In other examples, a clinician can evaluate the time course of perceptual sensitivity change of the visual system 202 (e.g., by evaluating the display data on the display 228) and determine if the patient needs treatment and if yes, the appropriate type, dose, and frequency of the treatment. In furthermore examples, the PSEE 230 can be programmed to evaluate the perceptual sensitivity change data 224 determine the efficacy of a treatment. In other examples, a clinician can evaluate the time course of perceptual sensitivity change of the visual system 202 and determine the efficacy of a treatment. Additionally, or alternatively, an appropriate amount of supplements (e.g., antioxidants, carotenoids, omega-3 fatty acids, etc.) for a nutrient therapy can be determined based on the time course of perceptual sensitivity change of the visual system 202 to treat one or more diseases.

Figure 3:
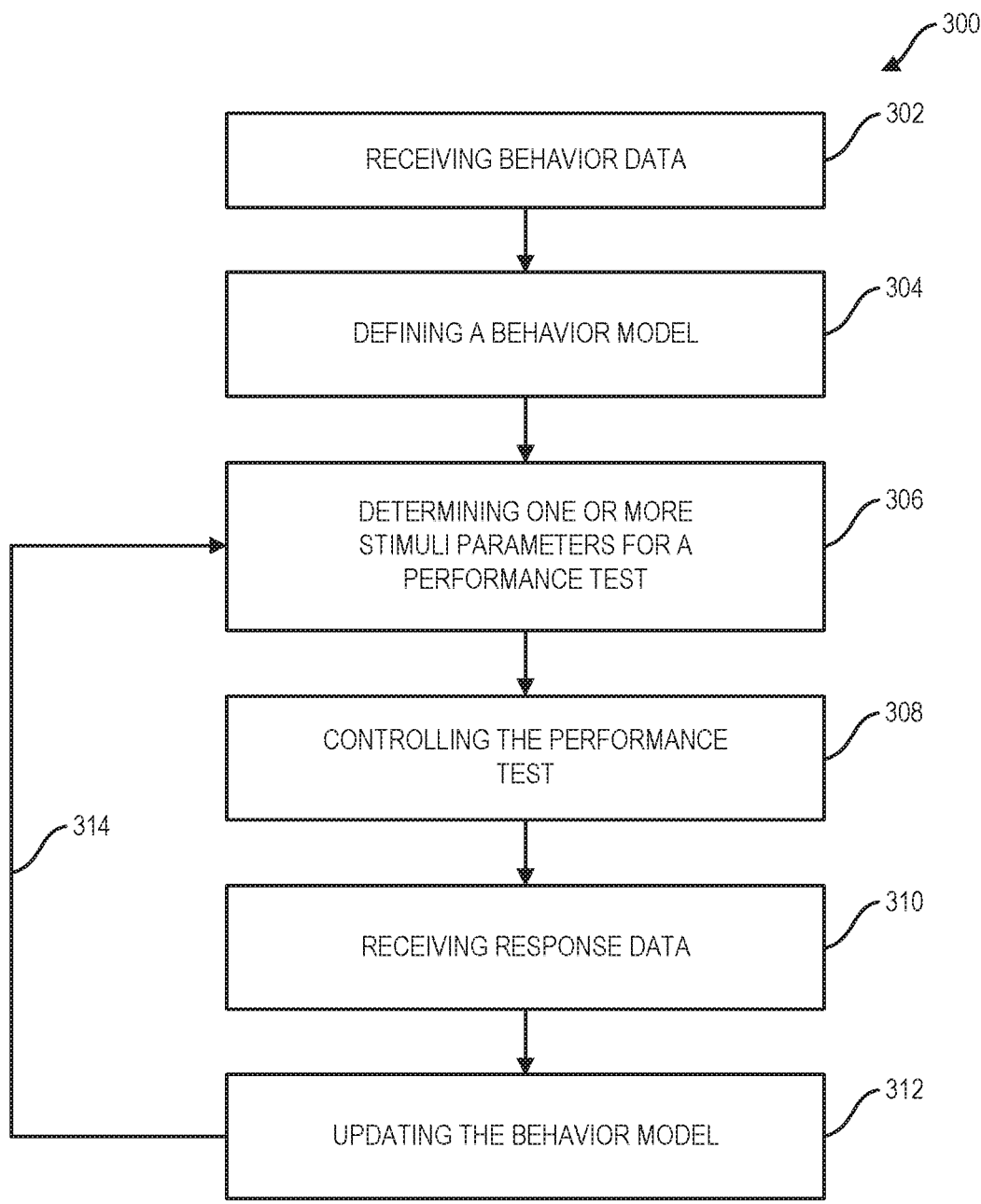
FIG. 3 depicts an example of a flow diagram illustrating an example method for measuring behavior changes of a process.
Figure 4:
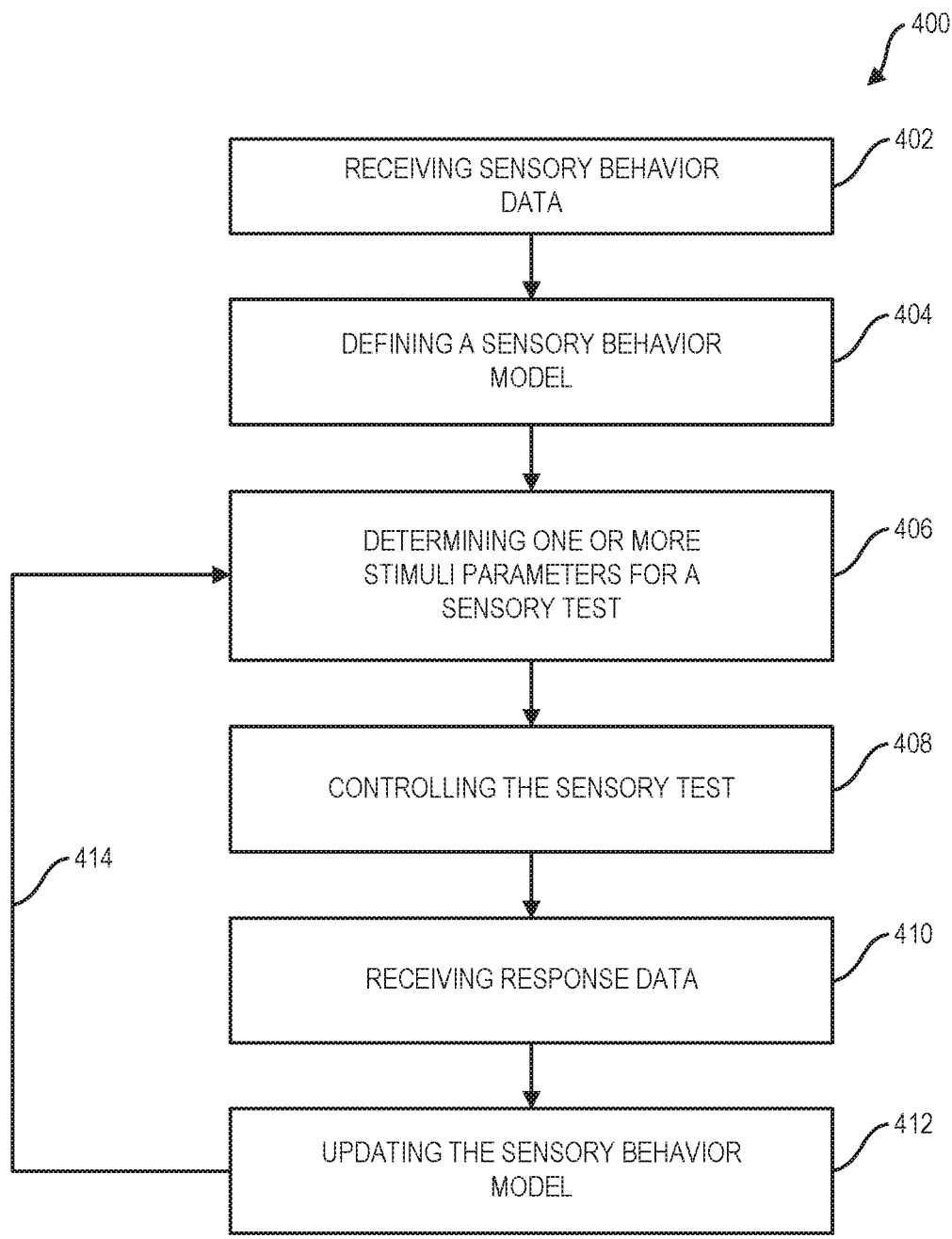
FIG. 4 depicts an example of a flow diagram illustrating an example method for measuring a time course of perceptual sensitivity change of a sensory system.

In view of the foregoing structural and functional features described above, methods that can be implemented will be better appreciated with reference to FIGS. 3-4. While, for purposes of simplicity of explanation, the methods of FIGS. 3-4 are shown and described as executing serially, it is to be understood and appreciated that such methods are not limited by their illustrated orders, as some aspects could, in other examples, occur in different orders and/or concurrently with other aspects from that shown and described herein. Moreover, not all illustrated features may be required to implement a method (e.g., rescoring data from other methods using the features of the component described herein). The method or portions thereof can be implemented as instructions stored in one or more non-transitory storage media as well as be executed by a processing resource (e.g., one or more processor cores) of a computer system, for example.

FIG. 3 depicts an example of a method 300 for measuring behavior changes of a process (e.g., the process 102, as depicted in FIG. 1). For example, the method 300 can be implemented by the BMS 100, as depicted in FIG. 1. The method can begin at 302 by receiving behavior data (e.g. the prior-behavior data 108 of FIG. 1) characterizing a prior behavioral change of the process. At 304, a behavior model can be defined that can include one or more behavior parameters based on the behavior data. At 306, one or more stimulus parameters for a performance test can be determined based on the one or more behavior parameters. The performance test can be applied to the process to provide a measure of behavior change of the process. At 308, an application of the performance test to the process can be controlled based on the stimulus parameter(s). At 310, response data characterizing one or more responses associated with the process during the performance can be received. In some examples, the response data can correspond to the observed behavior data 116, as depicted in FIG. 1. At 312, the one or more behavior parameters can be updated based on the response data. At 314, the behavior model characterizing the behavior change of the process can be updated by repeating 306, 308 and 310 for a plurality of applications of the performance test to the process. Additionally, or alternatively, a rescoring procedure by the method 300 can be done by providing trial-by-trial stimulus parameters and response from other methods into 306 and 310, respectively, while skipping 308.

FIG. 4 depicts an example of a flow diagram illustrating an example method for measuring time course of perceptual sensitivity change of a sensory system. For example, the method 400 can be implemented by the BMS 100, as depicted in FIG. 1, or the BMS 200, as depicted in FIG. 2. The method can begin at 402 by receiving sensory behavior data (e.g. the prior visual behavior data 208, as depicted in FIG. 2). The sensory behavior data can characterize a prior behavior change of the visual system. At 404, a sensory behavior model can be defined based on the sensory behavior data. The sensory behavior model can include one or more behavior parameters. At 406, one or more stimulus parameters for a sensory test can be determined based on the one or more behavior parameters. The sensory test can be applied to the sensory system to provide a measure of behavior change of the sensory system.

At 408, an application of the sensory test to the sensory system can be controlled based on the stimulus parameter(s). At 410, response data characterizing one or more responses of the sensory system (e.g., the observed visual behavior data 222, as depicted in FIG. 2) can be received based on the stimulus parameter. At 412, the one or more behavior parameters can be updated based on the response data. At 414, the sensory behavior model characterizing the behavior change of the sensory system can be updated by repeating 406, 408, 410 and 412, for example, according to a stopping criterion. Additionally, or alternatively, a rescoring procedure by the method 300 can be done by providing trial-by-trial stimulus parameters and response from other methods into 406 and 410, respectively, while skipping 408.

The following examples are intended to illustrate a performance of a qCD method (e.g., the method 300, as depicted in FIG. 3, or the method 400, as depicted in FIG. 4) relative to two other methods, a quick force-choice (qFC) method and a weighted staircase (WS) method (example 1 and 3) or a 3-down/1-up staircase (SC) method (examples 4 and 5). The qCD method can be implemented by the BMS 100, as depicted in FIG. 1, or the BMS 200, as depicted in FIG. 2. In a first example, the three methods were evaluated in Monte Carlo simulations of a psychophysical experiment of dark adaptation. In a second example, the qCD method was employed to access a cascade exponential function evaluated in Monte Carlo simulations of a psychophysical experiment of dark adaptation. In a third example, the qCD method was validated and compared with the qFC method in the psychophysical experiment of dark adaptation. In both the simulations and the psychophysical experiment of dark adaptation, the qCD method had a higher efficiency, accuracy and precision than the other two methods. In a fourth example, the qCD method was validated and compared with the SC method in a perceptual learning experiment. In a fifth example, the data collected by the SC method in example 4 was rescored using the qCD method. In a sixth example, a non-parametric perceptual sensitivity model (210 and 212 in FIG. 2) was used to access the time course of perceptual sensitivity change of the visual system 202.

The qFC method is a Bayesian based method that measures an average perceptual sensitivity over multiple trials by updating, trial-by-trial, a distribution of a sensitivity parameter, such as luminance threshold. The qFC method includes setting a broad prior distribution of luminance threshold, selecting a luminance stimulus for a subsequent trial that maximizes an expected gain on the sensitivity parameter, updating a posterior distribution of the luminance threshold by a Bayes' rule based on an observer's response after each trial and repeating the selecting and the updating until a stop criterion is met, such as a given number trials. The luminance threshold $\alpha_{FC}$ corresponds to d'=1.5 and is assumed to be constant for a duration of the qFC method. The broad prior distribution $p_0(\theta_{FC})$ is defined in a parameter space $\theta_{FC}=\alpha_{FC}$ and a one-dimension stimulus luminance space X covers all possible luminance thresholds $x \in X$. A Weibull function is used to approximate the psychometric function in the qFC method:

$$p'_t(r = 1 \mid \theta_{FC}, x) = g + (1-g)\left(1 - \exp\left(-\left(\frac{x}{\alpha_w(\theta_{FC})}\right)^\gamma\right)\right), \quad (17)$$

$$p_t(r = 1 \mid \theta_{FC}, x) = (1-\lambda)p'_t(r = 1 \mid \theta_{FC}, x) + \lambda g, \quad (18)$$

$$\log_{10}\alpha_w(\theta_{FC}) = \log_{10}(\alpha_{FC}) - \frac{1}{\gamma}\log_{10}\left(\log\left(\frac{1-g}{1-p_{1.5}}\right)\right). \quad (19)$$

The WS method is a weighted up-down method that relies on observer's responses to measure an average perceptual sensitivity. The weighted up-down method measures the luminance threshold at the accuracy level $p_{1.5}$=0.553, the probability correct when d'=1.5 in an 8-alternative-forced-choice (8AFC). Each correct response from an observer results in a decrease, $S_{down}$, in the luminance threshold and each incorrect response results in an increase, $S_{up}$, of the luminance threshold. In order to measure the threshold at $p_{1.5}$, $S_{down}$ and $S_{up}$ are constrained by the equation:

$$S_{down}p_{1.5}=S_{up}(1-p_{1.5}) \quad (20)$$

The Weibull function used to approximate the psychometric function in the staircase is:

$$p'_t(r = 1 \mid \theta_{SC}, x) = g + (1-g)\left(1 - \exp\left(-\left(\frac{x}{\alpha_w}\right)^\gamma\right)\right), \quad (21)$$

$$p_t(r = 1 \mid \theta_{SC}, x) = (1-\lambda)p'_t(r = 1 \mid \theta_{SC}, x) + \lambda g, \quad (22)$$

$$\log_{10}\alpha_w = \log_{10}(\alpha_{SC}) - \frac{1}{\gamma}\log_{10}\left(\log\left(\frac{1-g}{1-p_{1.5}}\right)\right), \quad (23)$$

where $\theta_{SC}=\alpha_{SC}$ is the luminance tested at the current step by the staircase.

Example 1

Simulation. Three observers were simulated $\vec{\theta}_{i,observer}=(\alpha_0, \alpha_1, \tau)$:

$\vec{\theta}_{1,observer}=(0.000376, 0.0113, 20)$ $\vec{\theta}_{2,observer}=(0.000376, 0.0113, 45)$ $\vec{\theta}_{3,observer}=(0.000376, 0.0113, 100)$ Performance of the qCD method, the WS method and the qFC method were evaluated and compared by a Monte Carlo simulation. Possible stimulus luminance was sampled from 0.000075 to 0.075 cd/m$^2$ with 120 equally spaced samples on a logarithmic scale.

In the qCD method, parameter space included 50 log-linearly spaced $\alpha_0$ values equally between 0.000075 and 0.0060 cd/m$^2$, 50 log-linearly spaced $\alpha_1$ values equally between 0.0023 and 0.030 cd/m$^2$, and 50 log-linearly spaced $\tau$ values equally between 5 and 200 seconds. For $\alpha_1$, 0 was also included to account for constant threshold. The prior distribution, $p_0(\vec{\theta})$, in the qCD method was defined by a hyperbolic secant function:

$$p_0(\vec{\theta})=\text{sech}(\alpha_{0,confidence}(\log_{10}(\alpha_0)-\log_{10}(\alpha_{0,guess})))\times$$
$$\text{sech}(\alpha_{1,confidence}(\log_{10}(\alpha_1)-\log_{10}(\alpha_{1,guess})))\times$$
$$(\text{sech}(\tau_{confidence,1}(\log_{10}(\tau)-\log_{10}(\Sigma_{guess,1})))+\text{sech}$$
$$(\tau_{confidence,2}(\log_{10}(\tau)\log_{10}(\tau)-\log_{10}(\tau_{guess,2})))), \quad (24)$$

where $$\text{sech}(x) = \frac{2}{e^x + e^{-x}};$$

$(\alpha_{0,guess}, \alpha_{1,guess}, \tau_{guess,1}, \tau_{guess,2})=(0.00075, 0.0075, 20, 100)$ are the peaks of the respective secant functions; $(\alpha_{0,confidence}, \alpha_{1,confidence}, \tau_{confidence,1}, \tau_{confidence,2})=(4, 4, 6, 6)$ are the spreads of the respective secant functions. Note that we use a distribution with two modes in setting up the prior for $\tau$ based on pilot experiment. The prior $p_0(\vec{\theta})$ is the multiplication of two secant functions of $\alpha_0$ and $\alpha_1$ and the average of two secant functions of $\tau$. The joint prior distribution $p_0(\vec{\theta})$ was updated trial-by-trial throughout the simulated experiment. The simulation was performed 1000 times for each simulated observer.

In the qFC method, parameter space included 120 log-linearly spaced $\alpha_w$ values equally between 0.000075 to 0.075 cd/m². The prior distribution, $p_0(\theta_{FC})$, in the qFC method was defined by a hyperbolic secant function:

$$p_0(\theta_{FC}) = \text{sech}(\alpha_{w,confidence} \times (\log_{10}(\alpha_{w,confidence}) - \log_{10}(\alpha_{w,guess}))), \quad (25)$$

where $\alpha_{w,confidence} = 3.16$ and $\alpha_{w,guess} = 0.0023$.

In the staircase, the range of the possible luminance was from 0.000075 to 0.075 cd/m². The starting luminance was 0.0075 cd/m². The step sizes were 0.05 and 0.062 log 10 units for $S_{down}$ and $S_{up}$, respectively.

Each simulated experimental run consisted of 300 trials and lasted for 600 seconds with 2-second inter-trial-interval (ITI). A simulated observer performed an 8AFC location identification task in a signal detection procedure. In each trial, a luminance disk appeared randomly in one of eight locations on an imaginary circle. The task of the simulated observer was to identify the location where the luminance disk appeared. The probability of a correct response was calculated for the qCD method by (11), for the qFC method by (17), and for the WS method by (21).

The response was simulated by drawing a random number y from a uniform distribution over the interval from 0 to 1. The response was scored as correct (r=1) if $y < p_r(r=1|\vec{\theta}, x)$, and incorrect otherwise. In the qCD method, the joint prior distribution $p_0(\theta)$ was updated trial-by-trial throughout one run of the 600-second experimental run. In the qFC method, threshold averages were estimated every 10-second. The prior distribution $p_0(\vec{\theta}_{FC} = \alpha_{FC})$ in the qFC method was updated only during the corresponding 10-second interval, which resulted in 60 posterior distributions after one run of the 600-second experimental run. The 60 posterior distributions obtained in one experimental run were used as the priors in the next experimental run. Ten repeated qFC runs were simulated. In the WS method, sixty staircases were run, one for each 10-second interval. In the first 600-second run, the luminance tested was updated continuously. Starting from the second run, each staircase was updated independently only during the corresponding 10-second interval. Ten repeated staircase runs were simulated. The simulations were performed 100 times for each method, thus in total 100 independent simulations qCD runs, 100 independent simulations of 10 repeated qFC runs, and 100 independent simulations of 10 repeated staircase runs.

Analysis. A trial-by-trial threshold can be estimated from the posterior distribution after each trial using a re-sampling method. The method does not impose any constraint on the posterior distribution. As such, the posterior distribution could vary from trial to trial, and the underlying exponential function could have different parameters from trial to trial.

In addition, a segment-by-segment estimate of the dark adaptation curve can be computed because the parameters of the curve may not change during some time intervals. The posterior distributions were partitioned based on their central tendency across time. The distance between the central tendency of the posterior distributions at two time points is quantified by a modified Mahalanobis distance MD:

$$MD(p_{t_{n_1}}(\vec{\theta}|r_{n_1},x_{n_1}), p_{t_{n_2}}(\vec{\theta}|r_{n_2},x_{n_2})) = \sqrt{\vec{y}C^{-1}\vec{y}^T}, \quad (26)$$

$$C = [C_1 + C_2]/2, \quad (27)$$

where $\vec{y} = [y_1, y_2, y_3]$, $y_i = \bar{\theta}_{a,n_1} - \bar{\theta}_{a,n_2}$, $\theta_a = \alpha_0$, $\alpha_1$, and $\tau$, for a=1, 2 and 3, respectively; $\vec{y}^T$ is the transpose of $\vec{y}$; $C^{-1}$ is the inverse of the matrix C; $C_b$(b=1 or 2) is the 3×3 covariance matrix of the posterior $$p_{t_{n_b}}(\vec{\theta}|r_{n_b},x_{n_b})$$

for which the diagonal elements $c_{b,a_1a_1}$ and the off-diagonal elements $c_{b,a_1a_2}$ ($a_1, a_2 \in [1,2,3]$, $a_1 \neq a_2$) are defined as:

$$c_{b,a_1a_1} = \text{Var}(\theta_{a_1,n_b}) = \Sigma_{\vec{\theta}}(\theta_{a_1} - \bar{\theta}_{a_1,n_b})^2 \cdot p_{t_{n_b}}(\vec{\theta}|r_{n_b},x_{n_b}), \quad (28)$$

$$c_{b,a_1a_2} = \quad (29)$$
$$\text{Cov}(\theta_{a_1,n_b}, \theta_{a_2,n_b}) = \Sigma_{\vec{\theta}}(\theta_{a_1} - \bar{\theta}_{a_1,n_b})(\theta_{a_2} - \bar{\theta}_{a_2,n_b}) \cdot p_{t_{n_b}}(\vec{\theta}|r_{n_b},x_{n_b}).$$

The null hypothesis is that the posterior distributions $$p_{t_{n_1}}(\vec{\theta}|r_{n_1},x_{n_1}) \text{ and } p_{t_{n_2}}(\vec{\theta}|r_{n_2},x_{n_2})$$

are the same. The null hypothesis is rejected when $$MD(p_{t_{n_1}}(\vec{\theta}|r_{n_1},x_{n_1}), p_{t_{n_2}}(\vec{\theta}|r_{n_2},x_{n_2})) > MD_0, \quad (30)$$

where $MD_0$ is a predetermined criterion.

To describe how the posterior distributions of the dark adaptation curve were partitioned, some notations were defined here: $n_{u_l,l}$ is the trial number in the experiment, where the subscripts l and $u_l$ refer to the $l^{th}$ segment and the $u_l^{th}$ trial in the $l^{th}$ segment, respectively. $U_l$ is the total number of trials in the $l^{th}$ segment and L is the number of segment(s) of the entire dark adaptation curve. To partition the dark adaptation curve into segments, we start from the last trial of the entire experiment, $n_{U_L,L}$. The MD between $$p_{t_{n_{U_L,L}}}(\vec{\theta}|r_{n_{U_L,L}},x_{n_{U_L,L}}) \text{ and } p_{t_{n_{u_L,L}}}(\vec{\theta}|r_{n_{u_L,L}},x_{n_{u_L,L}}),$$

the posterior distributions of the last trial and the posterior distributions of the previous trials, are calculated until $n_{U_{L-1},L-1}$, the last trial of the L–1$^{th}$ segment is found:

$$MD(p_{t_{n_{U_L,L}}}(\vec{\theta}|r_{n_{U_L,L}},x_{n_{U_L,L}}), p_{t_{n_{u_L,L}}}(\vec{\theta}|r_{n_{u_L,L}},x_{n_{u_L,L}})) \leq MD_0, \quad (31)$$
$$\forall u_L \in [1, U_L - 1],$$

$$MD(p_{t_{n_{U_L,L}}}(\vec{\theta}|r_{n_{U_L,L}},x_{n_{U_L,L}}), p_{t_{n_{1,L-1}}}(\vec{\theta}|r_{n_{1,L-1}},x_{n_{1,L-1}})) > MD_0, \quad (32)$$

where $n_{1,L} - 1 = n_{U_{L-1},L-1}$.

The procedure is repeated to find all the segments. Therefore, for the $l^{th}$ segment, $$MD(p_{t_{n_{U_l,l}}}(\vec{\theta}|r_{n_{U_l,l}},x_{n_{U_l,l}}), p_{t_{n_{u_l,l}}}(\vec{\theta}|r_{n_{u_l,l}},x_{n_{u_l,l}})) \leq MD_0, \quad (33)$$

-continued $$MD\left(p_{t_{n_{U_l,l}}}(\vec{\theta}|r_{n_{U_l,l}}, x_{n_{U_l,l}}), p_{t_{n_1,l-1}}(\vec{\theta}|r_{n_1,l-1}, x_{n_1,l-1})\right) > MD_0, \quad \forall u_l \in [1, U_l - 1], \quad (34)$$

Because the dark adaptation curve is continuous, the following constraint can be imposed on the posterior distributions between segments:

$$p_{n_{u_l,l}}(\alpha_0 + \alpha_1) = p_{t_{n_{U_{l-1},l-1}}}\left(\alpha_{t_{n_{U_{l-1},l-1}}}\right), \quad (35)$$

where $$p_{n_{u_l,l}}(\alpha_0 + \alpha_1)$$

is the marginal prior distribution of $\alpha_0 + \alpha_1$ at the trial $n_{u_{l,l}}$ ($u_l^{th}$ trial in the $l^{th}$ segment) and $$p_{t_{n_{U_{l-1},l-1}}}\left(\alpha_{t_{n_{U_{l-1},l-1}}}\right)$$

is the probability distribution of the threshold estimate at $$t_{n_{U_{l-1},l-1}}$$

of the $l-1^{th}$ segment.

Following segmentation, the posterior in the last trial of each segment $$p_{t_{n_{U_l,l}}}(\vec{\theta}|r_{n_{U_l,l}}, x_{n_{U_l,l}})$$

can be used to compute the estimated thresholds in the entire segment.

Evaluation. Following the simulations of each method, the simulations were evaluated. In the evaluation of threshold estimates by the three methods, time points, $t_k$, k=1~60, from 10 to 600 separated by 10 seconds, were included.

$$\begin{cases} t_1 = 10 \\ t_{k+1} - t_k = 10, \forall k > 1 \end{cases} \quad (36)$$

Accuracy was quantified by an average absolute bias and precision was quantified by an average standard deviation and an average 68.2% half width of credible interval. Both accuracy and precision were expressed in log 10 units.

In the qCD method, the average bias of parameter estimates after $n^{th}$ trial was determined according to:

$$\Sigma_m(\log_{10}(\overline{\theta}_{anm}) - \log_{10}(\theta_{a,true}))/M, \quad (37)$$

$$\overline{\theta}_{anm} = \Sigma_{\theta_a} \theta_a \cdot p_{t_{n,m}}(\theta_a | r_{nm}, x_{nm}), \quad (38)$$

where $\theta_{a,true}$ is the true parameter value of the simulated observer; $\theta_{anm}$, $t_{nm}$, $r_{nm}$, $c_{nm}$ and $p_{t_{nm}}(\theta_a | r_{nm}, x_{nm})$ are the estimate of the parameter $\theta_a$, the time at which the stimulus was presented, the observer's response, the stimulus luminance, and the marginal distribution defined in (7)~(9) after the $n^{th}$ trial in the $m^{th}$ simulation; M (=1000) is the total number of simulated runs. The average half width of the 68.2% credible interval (68.2% HWCI) of the estimated parameter $\theta_a$ is the half of the width of the interval within which the true value lies with 68.2% probability based on the marginal distribution $p_{t_{nm}}(\theta_a | r_{nm}, x_{nm})$.

The estimated threshold after the $n^{th}$ trial in the $m^{th}$ simulation is computed via a resampling procedure. 1000 parameter vectors $\vec{\theta}_{znm}$ are independently sampled based the joint posterior distribution $p_{t_{nm}}(\vec{\theta}|r_{nm}, x_{nm})$, where $z \in [1, 1000]$ and Z=1000 is the total number of samples. $\vec{\theta}_{znm}$ are used to compute 1000 sets of estimated values of the exponential functions at time point $t_k$.

The estimated threshold $\hat{\alpha}_{nm}^{t_k}$ at time $t_k$ in the $n^{th}$ trial in the $m^{th}$ simulation is the average of the 1000 samples:

$$\hat{\alpha}_{nm}^{t_k} = \Sigma_z \alpha_{znm}^{t_k}/Z = \Sigma_z \alpha(\vec{\theta}_{znm}, t_k)/Z, \quad (39)$$

where $\alpha(\vec{\theta}_{znm}, t_k)$ defined in (3), therefore an estimated threshold can be computed at any non-negative evaluation time $t_k$ regardless of the stimulus presentation time $t_{nm}$.

The accuracy of the estimated thresholds from the qCD was quantified by the average absolute bias across independent simulation runs. The trial-by-trial absolute bias of the estimated threshold at evaluation time $t_k$ after the $n^{th}$ trial across M runs is defined as:

$$|\Sigma_m(\log_{10}(\hat{\alpha}_{nm}^{t_k}) - \log_{10}(\alpha_{true}^{t_k}))|/M \quad (40)$$

where $\hat{\alpha}_{nm}^{t_k}$ is defined in (39), $\alpha_{true}^{t_k}$ is the true threshold of the simulated observer at time $t_k$. The average absolute bias of the estimated time course of perceptual sensitivity after the $n^{th}$ trial across M runs is defined as:

$$\Sigma_k |\Sigma_m(\log_{10}(\hat{\alpha}_{nm}^{t_k}) - \log_{10}(\alpha_{true}^{t_k}))|/(M \times K). \quad (41)$$

Precision was quantified by the standard deviation across independent simulation runs and by the half width of the credible interval within one run. The average trial-by-trial standard deviation of the estimated threshold after the $n^{th}$ trial across M runs is defined as:

$$\sqrt{\frac{\Sigma_m\left(\log_{10}(\hat{\alpha}_{nm}^{t_k}) - \log_{10}(\overline{\hat{\alpha}}_n^{t_k})\right)^2}{M}}. \quad (42)$$

$\overline{\hat{\alpha}}_n^{t_k}$ is the average estimated threshold after the $n^{th}$ trial across M runs:

$$\overline{\hat{\alpha}}_n^{t_k} = \Sigma_m \hat{\alpha}_n^{t_k}/M. \quad (43)$$

The standard deviation of the estimated time course of perceptual sensitivity change after the $n^{th}$ trial across M runs is defined as:

$$\sqrt{\frac{\Sigma_k \Sigma_m\left(\log_{10}(\hat{\alpha}_{nm}^{t_k}) - \log_{10}(\overline{\hat{\alpha}}_n^{t_k})\right)^2}{M \times K}}. \quad (44)$$

The credible interval represents the range within which the true value lies with a certain probability. A 68.2% HWCI is the half of the width of the interval within which the true value lies with 68.2% probability.

The estimated parameter $\hat{\alpha}_{n_{FC}m}^{t_k}$ is defined as the threshold estimate at time $t_k$ in the end of the $k^{th}$ 10-second measurement interval in the $n_{FC}^{th}$ iterated run in the $m^{th}$ simulation run. In other words, $\hat{\alpha}_{n_{FC}m}$ is the threshold estimate of the $k^{th}$ interval in the $n_{FC}^{th}$ iterated run in the $m^{th}$ simulation run. The average absolute bias of threshold estimates in the $n_{FC}^{th}$ iterated run across M simulation runs is defined as:

$$\Sigma_k \Sigma_m (\log_{10}(\hat{\alpha}_{n_{FC}m}^{t_k}) - \log_{10}(\alpha_{true}^{t_k}))|/(M \times K). \quad (45)$$

The standard deviation is defined as:

$$\sqrt{\frac{\Sigma_k \Sigma_m \left(\log_{10}(\hat{\alpha}_{n_{FC}m}^{t_k}) - \log_{10}(\overline{\hat{\alpha}}_{n_{FC}}^{t_k})\right)^2}{M \times K}}. \quad (46)$$

where $\overline{\hat{\alpha}}_{n_{FC}}^{t_k}$ is the average of the threshold estimate of the $k^{th}$ interval in the $n_{FC}^{th}$ iterated run across M simulations:

$$\overline{\hat{\alpha}}_{n_{FC}}^{t_k} = \Sigma_m \hat{\alpha}_{n_{FC}m}^{t_k}/M. \quad (47)$$

In the WS method, for each staircase, the average of the reversal points was the threshold estimate at $t_k$ in the end of the corresponding 10-second interval. The first two reversal points were discarded. The last reversal point was discarded if the number of the reversal points was odd. The average absolute bias of threshold estimates in the $n_{SC}^{th}$ iterated run is defined as:

$$\Sigma_k \Sigma_m (\log_{10}(\hat{\alpha}_{n_{SC}m}^{t_k}) - \log_{10}(\alpha_{true}^{t_k}))|/(M \times K). \quad (48)$$

where $\overline{\hat{\alpha}}_{n_{SC}}^{t_k}$ is the estimated threshold of $k^{th}$ interval in the $n_{SC}^{th}$ iterated run in the $m^{th}$ simulation.

The standard deviation was defined as:

$$\sqrt{\frac{\Sigma_k \Sigma_m \left(\log_{10}(\hat{\alpha}_{n_{SC}m}^{t_k}) - \log_{10}(\overline{\hat{\alpha}}_{n_{SC}}^{t_k})\right)^2}{M \times K}}. \quad (49)$$

where $\overline{\hat{\alpha}}_{n_{SC}}^{t_k}$ is the average of the threshold estimate of $k^{th}$ interval in the $n_{SC}^{th}$ iterated run across M simulations:

$$\overline{\hat{\alpha}}_{n_{SC}}^{t_k} = \Sigma_m \hat{\alpha}_{n_{SC}m}^{t_k}/M. \quad (50)$$

Figure 5A:
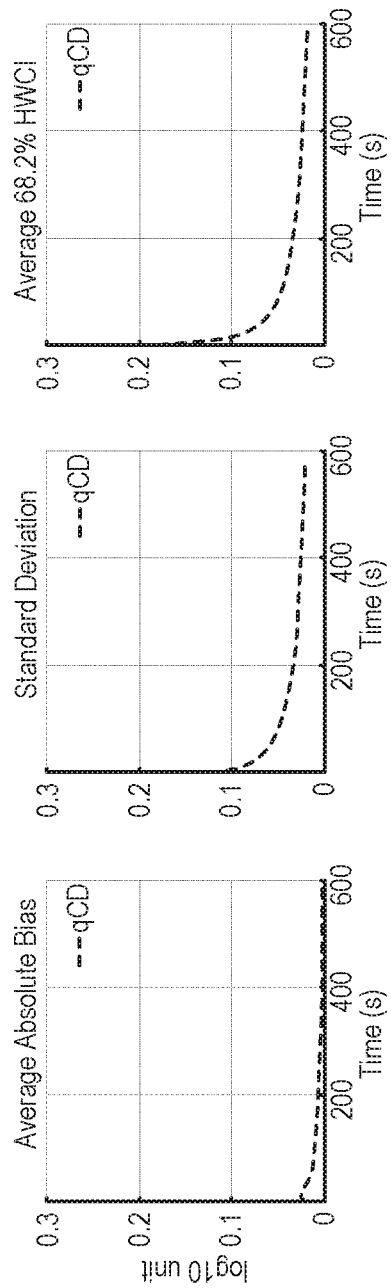
FIG. 5(a) depicts bias and precision as a function of time in seconds for three simulated observers in one qCD simulated run in a dark adaptation experiment.
Figure 5B:
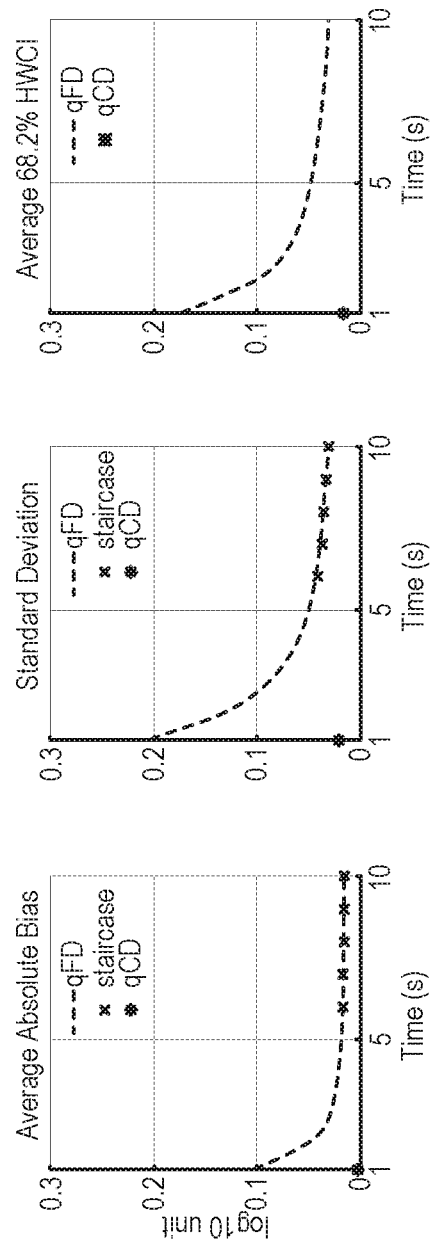
FIG. 5(b) depicts bias and precision as a function of run number of the qCD, qFC and weighted up-and-down staircase methods for three simulated observers in a dark adaptation experiment.

Example Results. Accuracy and precision of the estimated qCD parameters and the estimated thresholds by the qCD method, the qFC method and the WS method increased with trial number. Higher accuracy was indicated by smaller absolute average bias, and higher precision was indicated by smaller average standard deviation (of the threshold estimates only) and narrower average 68.2% HWCI (by qCD and qFC). Estimates by a single qCD run resulted in higher accuracy and precision in contrast to the 10 repeated qFC runs and the 10 repeated staircase runs. FIG. 5(a) shows the bias and precision (of the three simulated observers) as a function of time in seconds in one qCD simulation run. At t=0 second, the average absolute bias, standard deviation, and average 68.2% HWCI was 0.018, 0.136, and 0.188 log 10 units, respectively. These values decreased to 0.002, 0.021, and 0.017 log 10 units, respectively, at t=600 seconds. In comparison, FIG. 5(b) shows the bias and precision as a function of run number for the qFC and staircase methods. Asterisks represent the bias and precision in the end of a single qCD run. Dashed lines represent the bias and precision of qFC as a function of run number. Crosses represent accuracy and precision of the weighted up-and-down staircase method as a function of run number. The staircase did not converge until the 6$^{th}$ run. After one single qCD run, ten qFC runs and ten staircase runs, the average absolute bias was 0.002, 0.015 and 0.019 log 10 units, respectively; the standard deviation was 0.021, 0.031 and 0.031 log 10 units, respectively. The average 68.2% HWCI was 0.017 and 0.032 log 10 units after one single qCD run and ten qFC runs, respectively. Therefore, one single qCD run achieved higher accuracy and precision than those by the 10 qFC runs and the 10 staircase runs. Furthermore, while both the qFC and staircase methods had persistent bias, qCD had nearly zero bias.

Figure 6A:
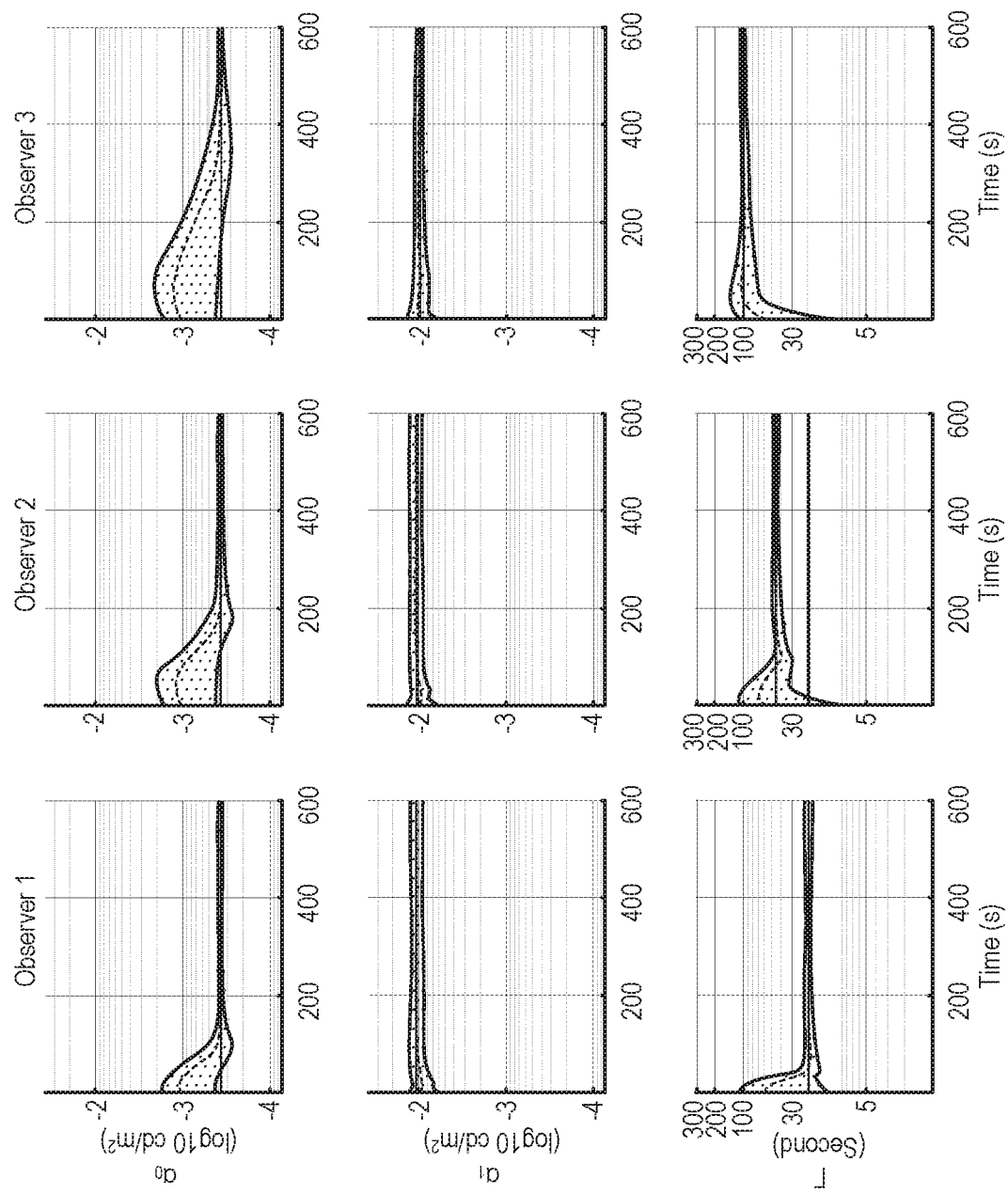
FIG. 6(a) depicts trial-by-trial parameter estimates for three simulated observers in a dark adaptation experiment.
Figure 6B:
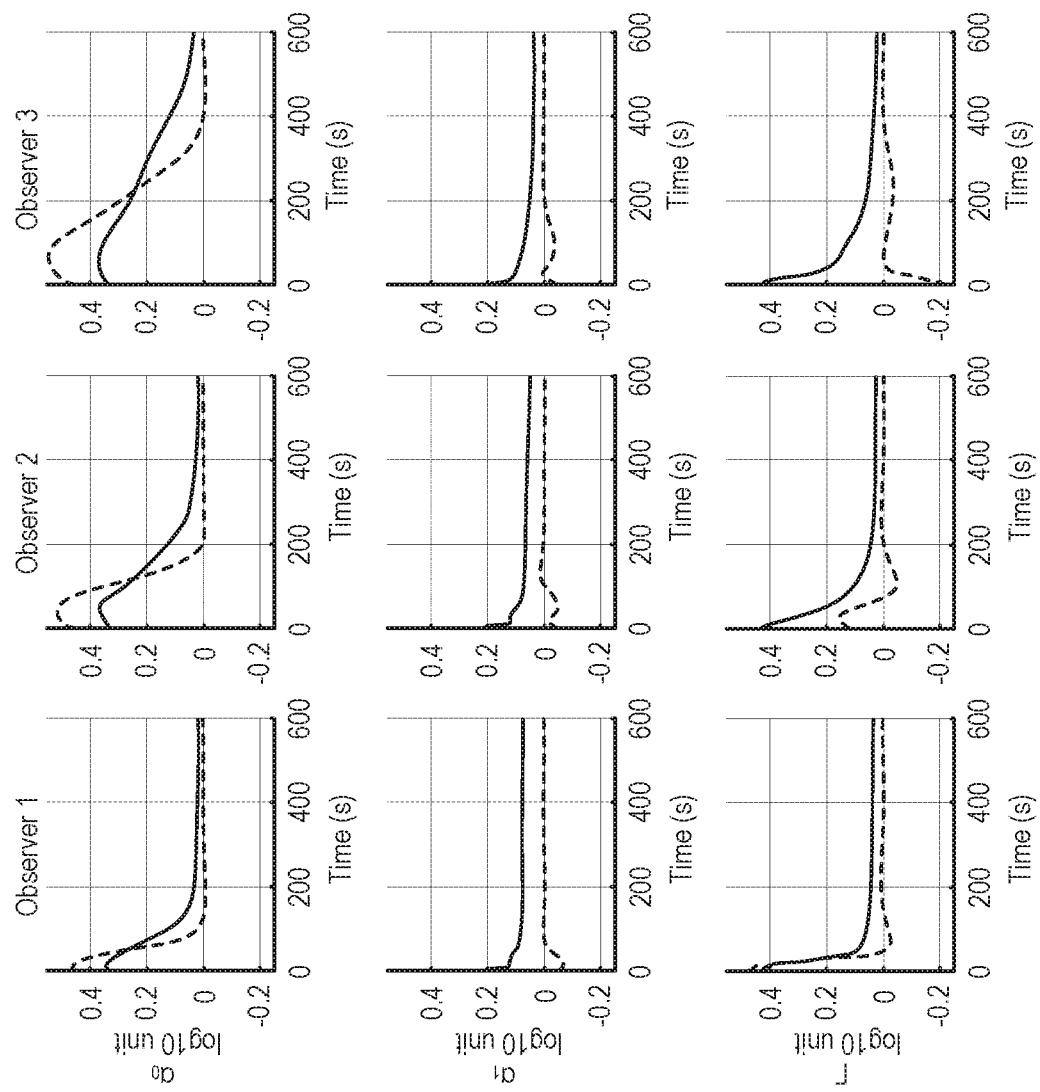
FIG. 6(b) depicts accuracy and precision of trial-by-trial parameter estimates for three simulated observers in a dark adaptation experiment.

FIG. 6(a)-6(b) illustrate the trial-by-trial parameter estimates and their accuracy and precision averaged across 1000 qCD simulations. FIG. 6(a) shows the narrowing and convergence of the posterior distribution to the true parameter values (solid lines) as the decrease of the average 68.2% HWCIs (shaded area) of the marginal posterior distributions of the parameters and the decrease of the bias of the parameter estimates (distance between the dashed lines and solid lines), respectively. FIG. 6(b) shows the bias (dashed lines) and average 68.2% HWCI (solid lines) of $\alpha_0$, $\alpha_1$, and $\tau$ for observers 1~3. For $\alpha_0$, the average bias was 0.445, 0.444, and 0.444 log 10 units for simulated observer 1, 2, and 3, respectively, in the beginning at t=0 second. It became 0.001, 0.000, and 0.000 log 10 units after 600 seconds. For $\alpha_1$, the average bias was −0.044, −0.047, and −0.050 log 10 units for simulated observer 1, 2, and 3, respectively, at t=0. It became 0.000, −0.003, and 0.001 log 10 units after 600 seconds. For $\tau$, the average bias was 0.477, 0.125, and −0.222 log 10 units for simulated observer 1, 2, and 3, respectively, at t=0. It became 0.003, 0.004, and 0.001 log 10 units after 600 seconds. For $\alpha_0$, the average 68.2% HWCI was 0.333, 0.333, and 0.332 log 10 units for simulated observer 1, 2, and 3, respectively, at t=0. It decreased to 0.017, 0.019, and 0.037 log 10 units after 600 seconds. For $\alpha_1$, the average 68.2% HWCI was 0.210, 0.210, and 0.211 log 10 units for simulated observer 1, 2, and 3, respectively, at t=0. It decreased to 0.076, 0.052, and 0.037 log 10 units after 600 seconds. For $\tau$, the average 68.2% HWCI was 0.432, 432, and 0.432 log 10 units for simulated observer 1, 2, 3 and 4, respectively, at t=0. It decreased to 0.040, 0.029, and 0.026 log 10 units after 600 seconds. Therefore, the accuracy and precision of parameter estimates improved with time for all three simulated observers.

Figure 7:
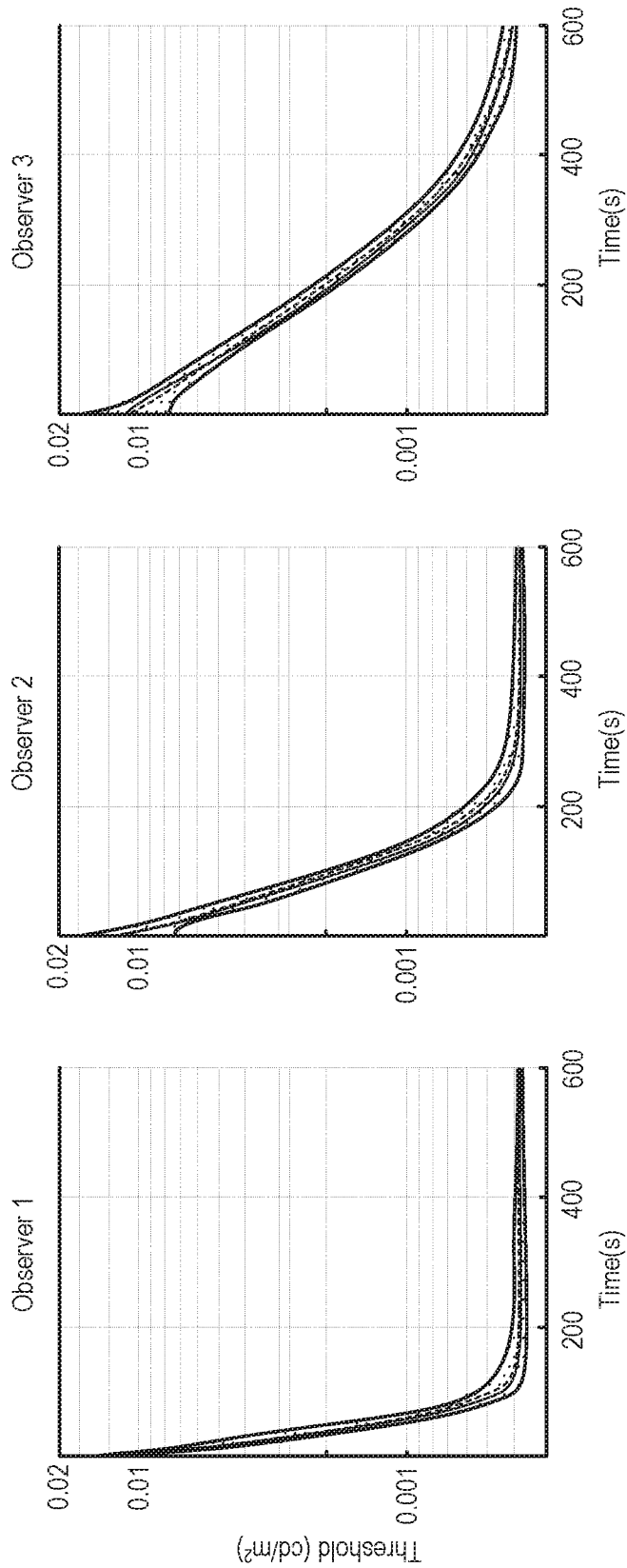
FIG. 7 depicts trial-by-trial threshold estimates for three simulated observers in qCD simulations in a dark adaptation experiment.

FIG. 7 illustrates the trial-by-trial threshold estimates by qCD for the three simulated observers. To compute the trial-by-trial threshold, the posterior distribution after each trial was used. Threshold estimates (log 10 scale on y-axis) are plotted as functions of time (in seconds) elapsed since the beginning of the dark adaptation. The solid lines represent the true values of the simulated observers, the dashed lines represent the average estimates and the shaded areas represent the average 68.2% HWCI. For simulated observer 1, the average absolute bias, standard deviation, and average 68.2% HWCI of the estimated thresholds during 600-second dark adaptation was 0.010, 0.032, and 0.031 log 10 units, respectively. For simulated observer 2, the average absolute bias, standard deviation, and average 68.2% HWCI of the estimated thresholds in the 600-second dark adaptation was 0.013, 0.039, and 0.039 log 10 units, respectively. For simulated observer 3, the average absolute bias, standard deviation, and average 68.2% HWCI of the estimated thresholds in the 600-second dark adaptation was 0.015, 0.039, and 0.043 log 10 units, respectively. These results thus demonstrate the high precision and accuracy of the trial-by-trial qCD estimates.

In the trial-by-trial procedure, the posterior distribution after each trial is used to estimate the threshold in that trial. While the procedure achieved high precision and accuracy, the segment-by-segment estimation further improved the accuracy and precision. The criterion $MD_0$ in (29) was set to 6.58. Out of the 1000 simulated runs, 0, 10, and 21 runs resulted in two posterior segments for simulated observer 1, 2, and 3, respectively while all the remaining runs only indicated one segment for the entire 600-second experiment. Based on this criterion, only one posterior distribution is necessary to describe the dark adaptation curves of the three simulated observers. Therefore, the posterior distributions at 600 seconds were used to compute the estimated thresholds on the entire dark adaptation curve for each simulated observer.

Figure 8:
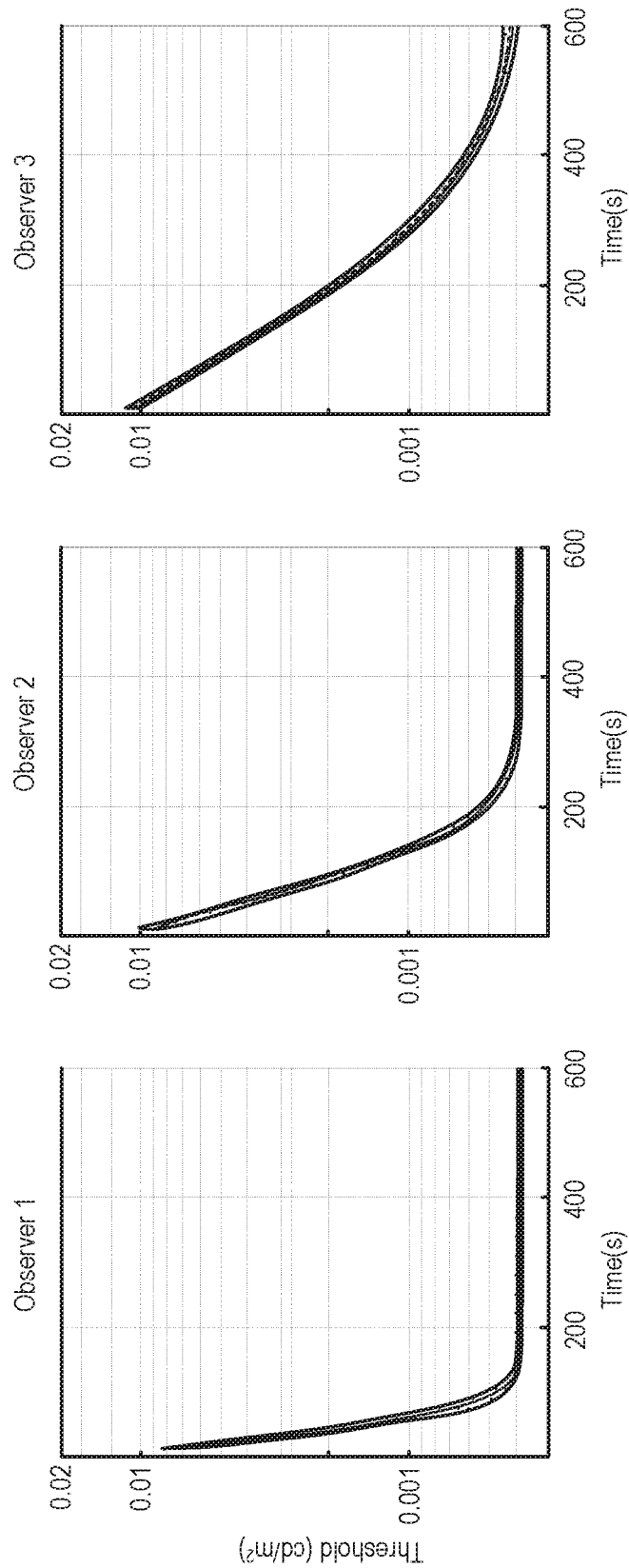
FIG. 8 depicts segment-by-segment threshold estimates for three simulated observers in qCD simulations in a dark adaptation experiment.

FIG. 8 illustrates the estimated dark adaptation curve in the end of one qCD run for the three simulated observers. The solid lines represent the true exponential decay functions of the simulated observers, the dashed lines represent the estimated exponential decay functions and the shaded areas represent the average 68.2% HWCI. For simulated observer 1, the average absolute bias, standard deviation, and average 68.2% HWCI was 0.002, 0.020, and 0.013 log 10 units, respectively. For simulated observer 2, the average absolute bias, standard deviation, and average 68.2% HWCI was 0.002, 0.021, and 0.017 log 10 units, respectively. For simulated observer 3, the average absolute bias, standard deviation, and average 68.2% HWCI was 0.002, 0.020, and 0.017 log 10 units, respectively.

Figure 9A:
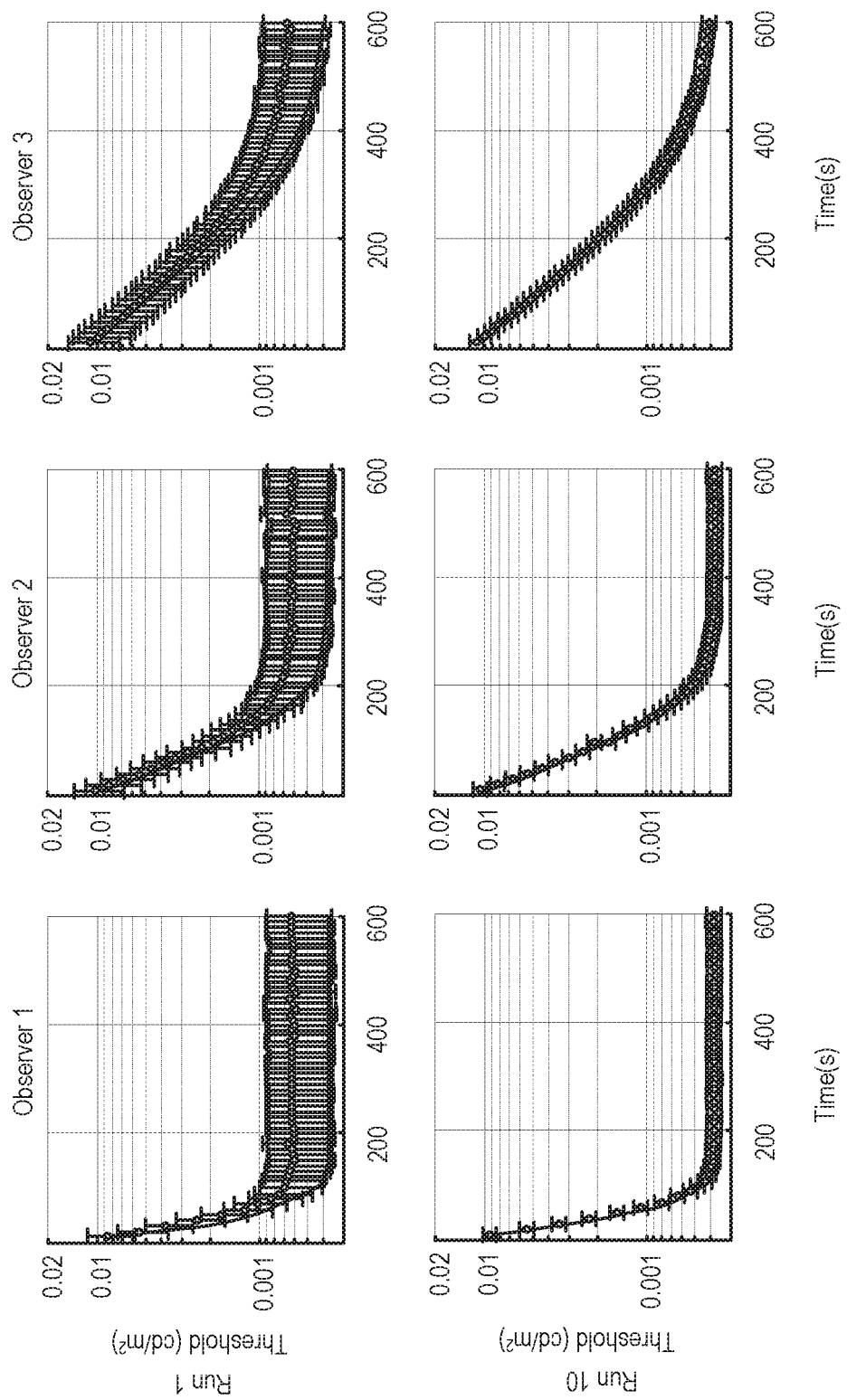
FIG. 9(a) depicts a history of estimated thresholds for three simulated observers by the qFC method in a dark adaptation experiment.
Figure 9B:
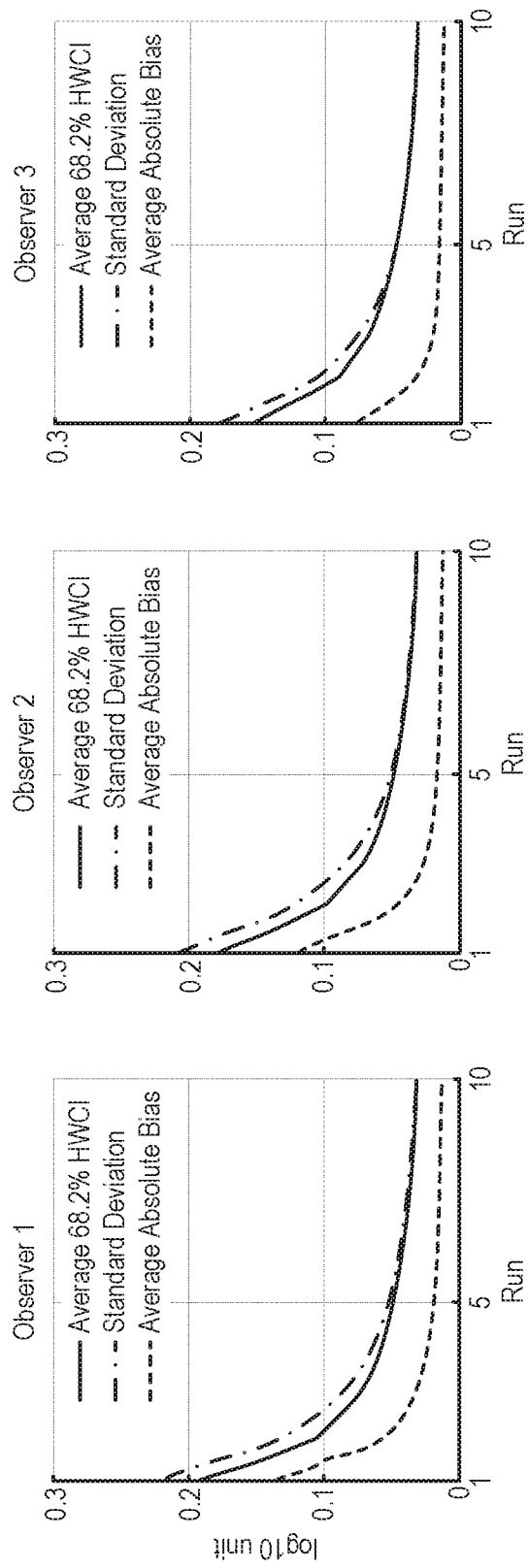
FIG. 9(b) depicts an average absolute bias, an average 68.2% HWCI and a standard deviation for three simulated observers in qFC simulations in a dark adaptation experiment.

FIG. 9(*a*) illustrates the estimated thresholds after the $1^{st}$ and $10^{th}$ qFC run for the three simulated observers. Results of the three simulated observers are presented in different columns. Estimates after the $1^{st}$ and $10^{th}$ runs are plotted in different rows. The solid lines are the true thresholds of the simulated observers, the dots are the threshold estimates by qFC and the error bars are the average 68.2% HWCI. FIG. 9(*b*) illustrates the accuracy (the average absolute bias, dashed lines) and the precision (the standard deviation and the average 68.2% HWCI, dotted lines and solid lines, respectively). For simulated observer 1, the average absolute bias was 0.133, 0.051, 0.032, and 0.017 log 10 units after $1^{st}$, $2^{nd}$, $3^{rd}$ and $10^{th}$ run, respectively; the standard deviation was 0.213, 0.128, 0.086, and 0.032 log 10 units after the $1^{st}$, $2^{nd}$, $3^{rd}$ and $10^{th}$ run, respectively; the average 68.2% HWCI was 0.193, 0.105, 0.073, and 0.032 log 10 units after the $1^{st}$, $2^{nd}$, $3^{rd}$ and $10^{th}$ run, respectively. For simulated observer 2, the average absolute bias was 0.112, 0.042, 0.026, and 0.015 log 10 units after the $1^{st}$, $2^{nd}$, $3^{rd}$ and $10^{th}$ run, respectively; the standard deviation was 0.210, 0.121, 0.081, and 0.031 log 10 units after the $1^{st}$, $2^{nd}$, $3^{rd}$ and $10^{th}$ run, respectively; the average 68.2% HWCI was 0.180, 0.101, 0.071, and 0.032 log 10 units after the $1^{st}$, $2^{nd}$, $3^{rd}$ and $10^{th}$ run, respectively. For simulated observer 3, the average absolute bias was 0.066, 0.024, 0.016, and 0.013 log 10 units after the $1^{st}$, $2^{nd}$, $3^{rd}$ and $10^{th}$ run, respectively; the standard deviation was 0.177, 0.104, 0.073, and 0.031 log 10 units after the $1^{st}$, $2^{nd}$, $3^{rd}$ and $10^{th}$ run, respectively; the average 68.2% HWCI was 0.153, 0.091, 0.066, and 0.031 log 10 units after the $1^{st}$, $2^{nd}$, $3^{rd}$ and $10^{th}$ run, respectively.

Figure 10A:
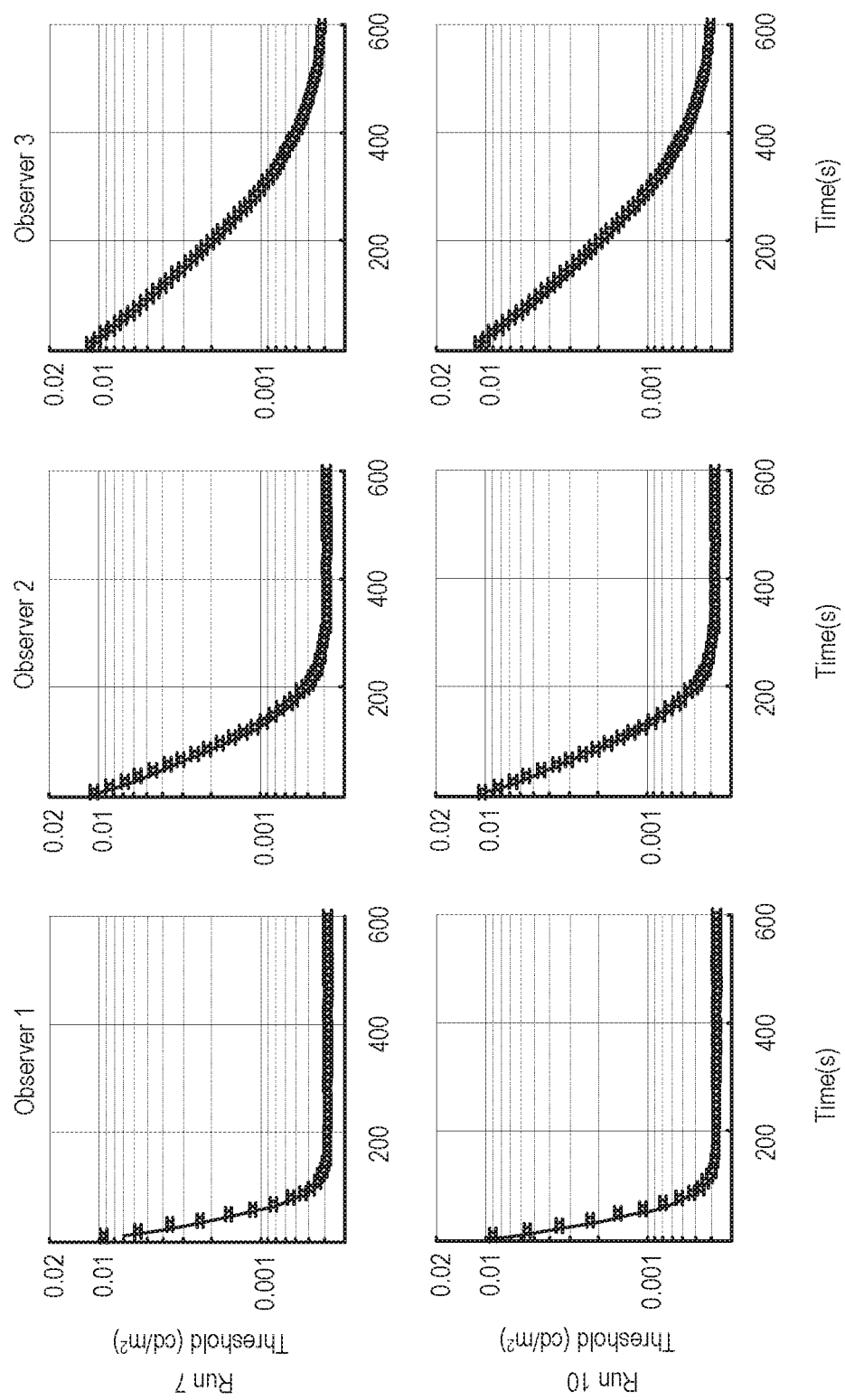
FIG. 10(a) depicts a history of estimated thresholds for three simulated observers by a weighted staircase (WS) method in a dark adaptation experiment.
Figure 10B:
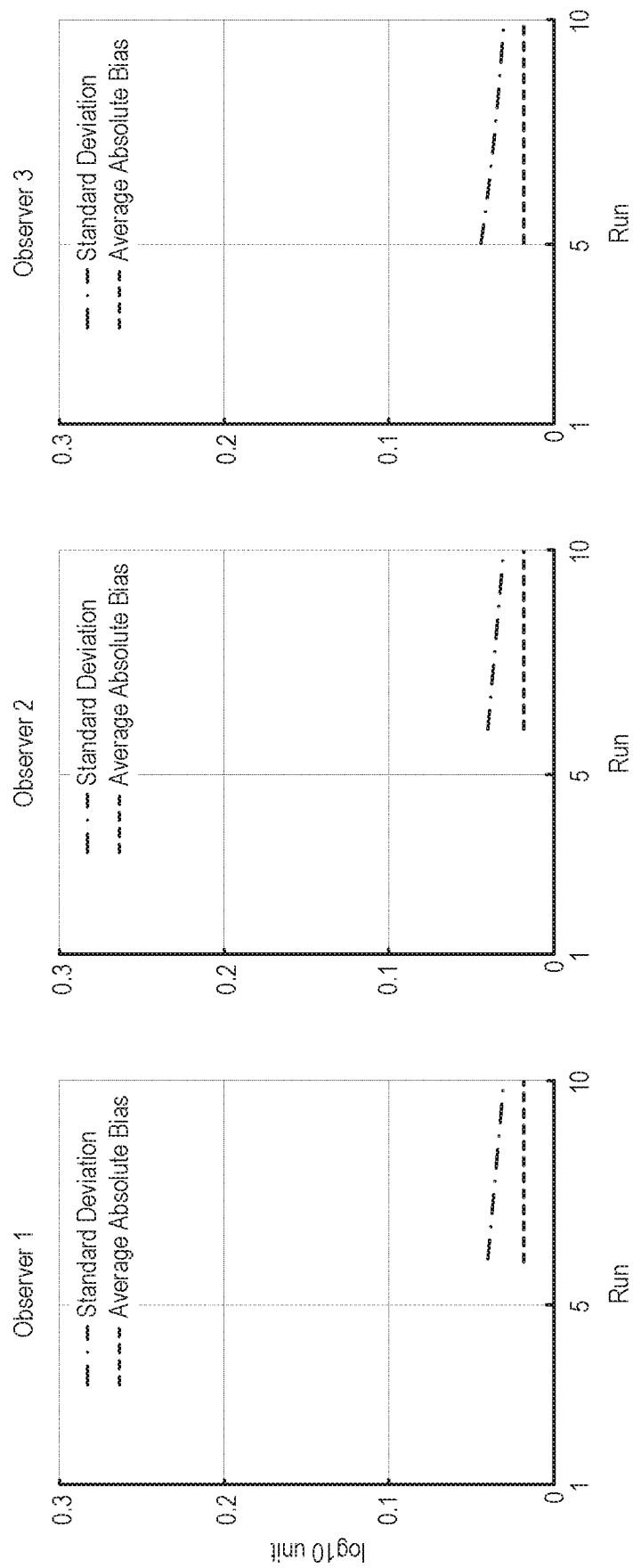
FIG. 10(b) depicts an average absolute bias, and a standard deviation for three simulated observers in WS simulations in a dark adaptation experiment.

With regard to the WS method, it did not converge (with at least 4 reversals) until the $6^{th}$, $6^{th}$ and $5^{th}$ run for simulated observer 1, 2, and 3, respectively. FIG. 10(*a*) illustrates the estimated thresholds after the $7^{th}$ and $10^{th}$ staircase run for the three observers. The solid lines are the true values of the simulated observers, the dots are the threshold estimates by staircase and the error bars are the average 68.2% HWCI. FIG. 10(*b*) illustrates the accuracy (the average absolute bias, dashed lines) and the precision (the standard deviation, dotted lines). For simulated observer 1, the average absolute bias and the standard deviation was 0.019 and 0.031 log 10 units after the $10^{th}$ run. For simulated observer 2, the average absolute bias and the standard deviation was 0.019 and 0.031 log 10 units after the $10^{th}$ run. For simulated observer 3, the average absolute bias and the standard deviation was 0.019 and 0.031 log 10 units after the $10^{th}$ run.

Example 2

Simulation. Two observers whose luminance threshold change as a cascade exponential function in dark adaptation:

$$\alpha(\vec{\theta}, t) = \begin{cases} \alpha_{01} + \alpha_{11} \exp(-t/\tau_1), t \le t_c \\ \alpha_{02} + \alpha_{12} \exp(-(t-t_c)/\tau_2), t > t_c \end{cases} \quad (51)$$

where $\alpha_{02} = \alpha_{01} + \alpha_{11} \exp(-t_c/\tau) - \alpha_{12}$. Parameters for observer 4 were set as follows $\vec{\theta}_{4,observer} = (\alpha_{11}, \tau_1, \alpha_{01}, \tau_2, t_c) = (0.0150, 50, 0.0030, 0.0023, 85, 270)$, and observer 5 to $\vec{\theta}_{5,observer} = (\alpha_{11}, \tau_1, \alpha_{01}, \alpha_{12}, \tau_2, t_c) = (0.0150, 50, 0.0030, 0.0023, 200, 270)$.

For observer 4, a 600-second experiment was simulated. For observer 5, a 1200-second experiment was simulated. A 2-second inter-trial-interval (ITI) was implemented in all the simulations. For each run of the simulated 600-second experiment, there were 300 trials; for each run of the 1200-second experiment, there were 600 trials.

Analysis. Same as in Example 1.

Evaluation. Same as in Example 1. Only the threshold estimates were evaluated.

Figure 11:
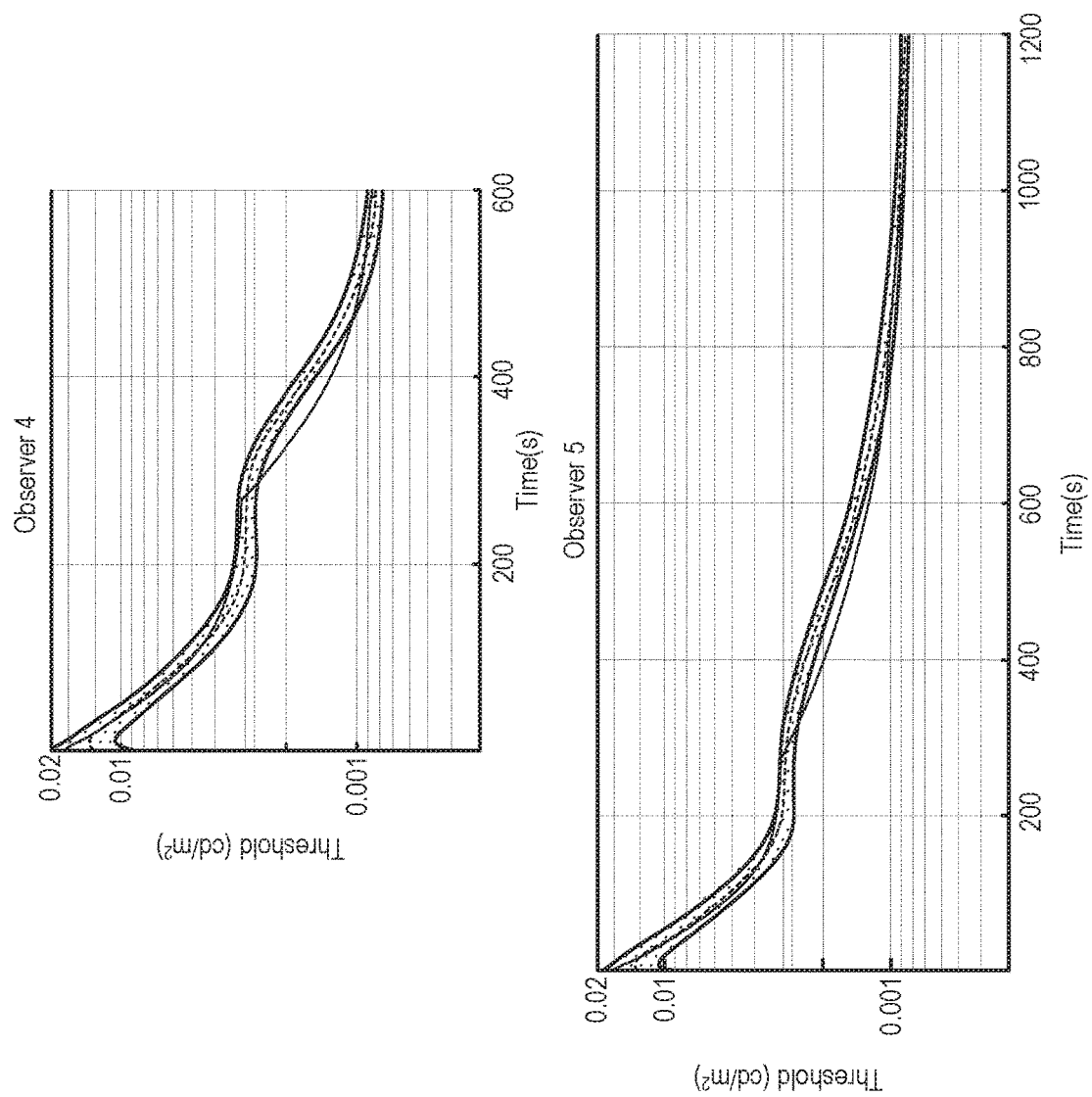
FIG. 11 depicts trial-by-trial threshold estimates for two simulated observers in qCD simulations in a dark adaptation experiment.

Example Results. FIG. 11 illustrates the trial-by-trial threshold estimates by the qCD method for observers 4 and 5. The solid lines represent the true thresholds of the simulated observers, the dashed lines represent the average estimates, and the shaded areas represent the average 68.2% HWCI. For observer 4, the average absolute bias, standard deviation, and average 68.2% HWCI of the estimated trial-by-trial thresholds was 0.042, 0.048, and 0.049 log 10 units, respectively. For observer 5, the average absolute bias, standard deviation, and average 68.2% HWCI of the estimated trial-by-trial thresholds was 0.037, 0.035, and 0.034 log 10 units, respectively.

Figure 12:
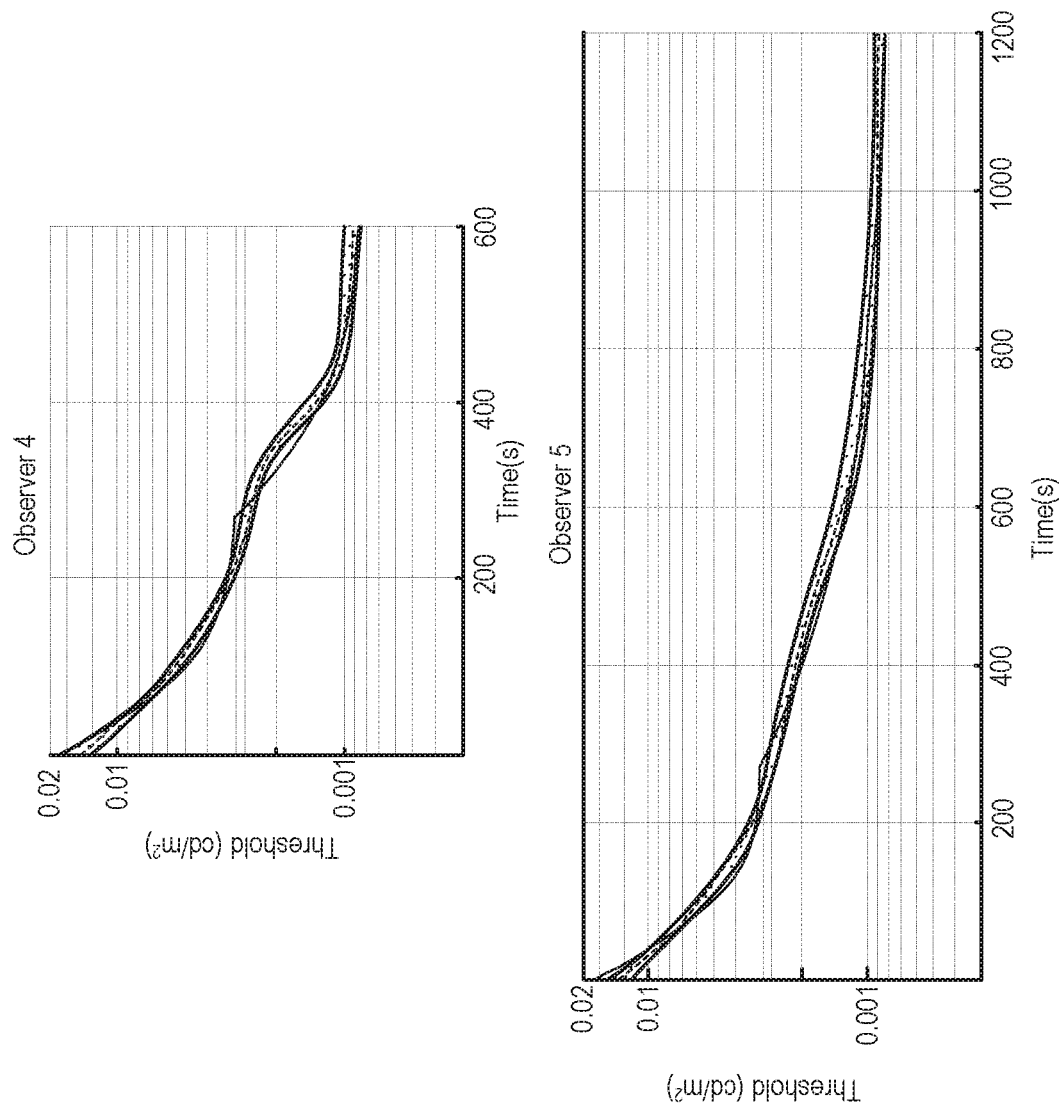
FIG. 12 depicts segment-by-segment threshold estimates for two simulated observers in qCD simulations in a dark adaptation experiment.

FIG. 12 illustrates the segmented threshold estimates by the qCD method for observers 4 and 5. The solid lines represent the true exponential decay functions of the simulated observers, the dashed lines represent the estimated exponential decay functions and the shaded areas represent the average 68.2% HWCI. For observer 4, the number of runs with one, two, and three segments were 133, 864, and 3, respectively. For the 864 two-segment simulation runs, the average $t_c$ is 337±51.6 seconds. The average absolute bias, standard deviation, and average 68.2% HWCI of the segmented threshold estimations was 0.027, 0.040, and 0.027 log 10 units, respectively. For observer 5, the number of runs with one, two, three and four segments were 9, 838, 151, and 2, respectively. For the 838 two-segment simulation runs, the average estimated $t_c$ is 479.9±79.6 seconds. For the 151 three-segment simulation runs, the average estimated $t_c$ is 352.6±64.1 seconds, with the second $t_c$ at 607.4±64.7 seconds. The average absolute bias, standard deviation, and average 68.2% HWCI of the segmented threshold estimations was 0.023, 0.028, and 0.023 log 10 units, respectively.

Example 3

Experiment. A psychophysical experiment was conducted to evaluate and compare the performance of the qCD and qFC methods. Each experimental run consisted of two parts: exposure to high luminance of 75 cd/m² for 15 seconds and 150 cd/m² for 120 seconds with room lights on, which resulted in about 3% bleach of retinal pigments. This was immediately followed by measurement of luminance detection thresholds during 600-second dark adaptation at 0.000 cd/m² mean luminance with room lights off. Only one method, qCD or qFC, was used in each run. Each subject finished four independent qCD runs and four connected qFC runs. Two different assessment methods were used in any two consecutive runs. The method used in the first run was randomly selected for each subject.

In each qFC run, thresholds were estimated every 10 seconds. The prior distribution $p_0(\theta_{FC} = \alpha_{FC})$ was updated only during the corresponding 10-second interval which resulted in 60 posterior distributions after one run of the 600-second experiment. The 60 posterior distributions obtained in one run were used as the priors in the next run. The qFC procedure was iterated in four runs for a single subject in the psychophysical experiment. Consistent with the simulations, qCD showed higher precision and efficiency than qFC in all four subjects.

Methods. The experiment was conducted on a PC computer with Pyschtoolbox 3.0.11 extensions in MATLAB R2013a. The computer was used to drive a 46-inch NEC MultiSync P463 LCD monitor that was viewed binocularly with natural pupils at a two-meter viewing distance. A chin rest was used to stabilize subject's head. Responses were collected via a wireless keyboard. Luminance was controlled by a pair of goggles with removable neutral density filters with a total of 3.3 ND (one 2.4 ND and one 0.9 ND), reducing light intensity by a factor of $10^{33}$ (or 99.95%) in each eye. The goggles were worn throughout the whole experiment but the neutral density filters were flipped on only during the 600-second dark adaptation phase. Room lights were turned off during dark adaptation.

Figure 13A:
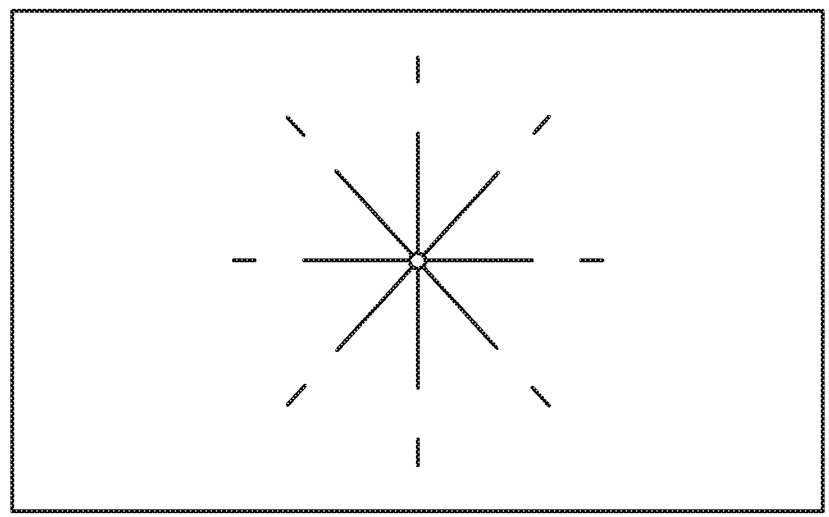
FIG. 13(a) depicts an example of an imaginary circle with a fixation dot used in a dark adaptation experiment.
Figure 13B:
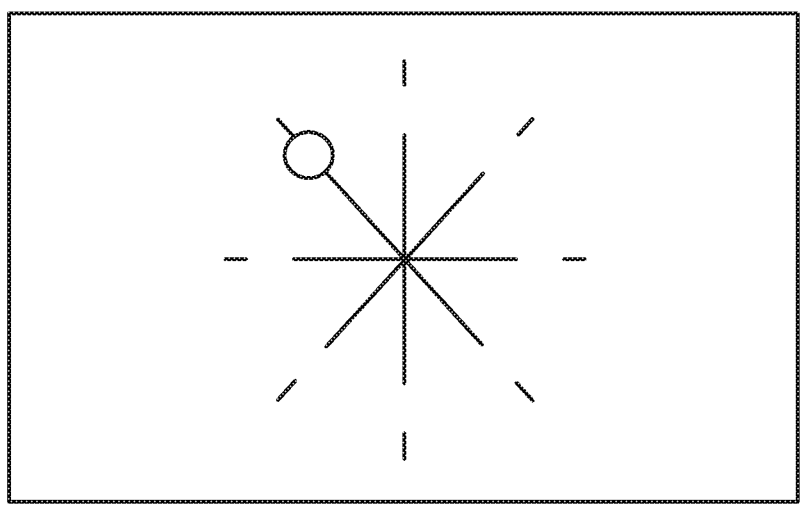
FIG. 13(b) depicts another example of an imaginary circle with luminance disk used in a dark adaptation experiment.

The target in each trial was a 1.7°-diameter luminance disk that could occur at one of eight locations of an imaginary 5-diameter circle. The luminance of the disk varied trial by trial and was determined by the adaptive procedures. Four 13.4°-long and 0.06°-wide lines crossing the centers of the eight potential locations and the center of the display (with gaps to allow potential stimulus presentation), were presented throughout the experiment to reduce spatial uncertainty of the stimuli. A 0.5°-diameter dot was also presented at the fixation, as illustrated in FIG. 13(a), but disappeared during the presentation of the target disk, as illustrated in FIG. 13(b). The disappearance of the fixation dot served as a temporal cue. The luminance of the cues was 60, 135, and 0.0376 cd/m² during the 15-second exposure, 120-second exposure and 600-second dark adaptation phase, respectively.

During each trial, one single disk appeared for 0.2 second randomly at one of the eight possible locations (gaps on the lines), simultaneous with the offset of the 0.5°-diameter center fixation dot (example shown in FIG. 13(b)). The subject pressed one of the eight keys to indicate the location where the disk occurred. No feedback was given to the subject. The next trial started 0.2 second after a key was pressed. Each experimental run started with a 15-second exposure to a screen with a uniform luminance of 75 cd/m². Then the screen luminance doubled to 150 cd/m² for the duration of 120 seconds. During 120-second exposure, the respective adaptive method selected the luminance decrease of the disk as a practice for the following dark adaptation. The text "Lights off, Filters on" showed up on the screen during the last 3 seconds of this phase to instruct the subject to flip on the neutral density filters as soon as when the dark adaptation started. The screen luminance fell to 0.000 cd/m² immediately at the end of the 120-second exposure and the room lights were turned off simultaneously. A new text "Press 5 when ready" instructed the subject to press "5" key to initiate the first trial in the dark adaptation.

Evaluation. The agreement between the qCD and qFC measurements was quantified by the root mean squared error (RMSE) between the estimated thresholds from the two methods:

$$\text{RMSE} = \sqrt{\Sigma_k (\log_{10}(\hat{\alpha}_4^{t_k}) - \log_{10}(\overline{\hat{\alpha}}^{t_k}))^2 / K}, \tag{52}$$

where $\hat{\alpha}_4^{t_k}$ is the estimated threshold of the $k^{th}$ interval in the $4^{th}$ qFC run and $\overline{\hat{\alpha}}^{t_k}$ is the average trail-by-trial threshold estimate at time $t_k$ by the qCD across $M_{CD} = 4$ runs.

$$\overline{\hat{\alpha}}^{t_k} = \Sigma_m \hat{\alpha}_m^{t_k} / M_{CD}. \tag{53}$$

Figure 14:
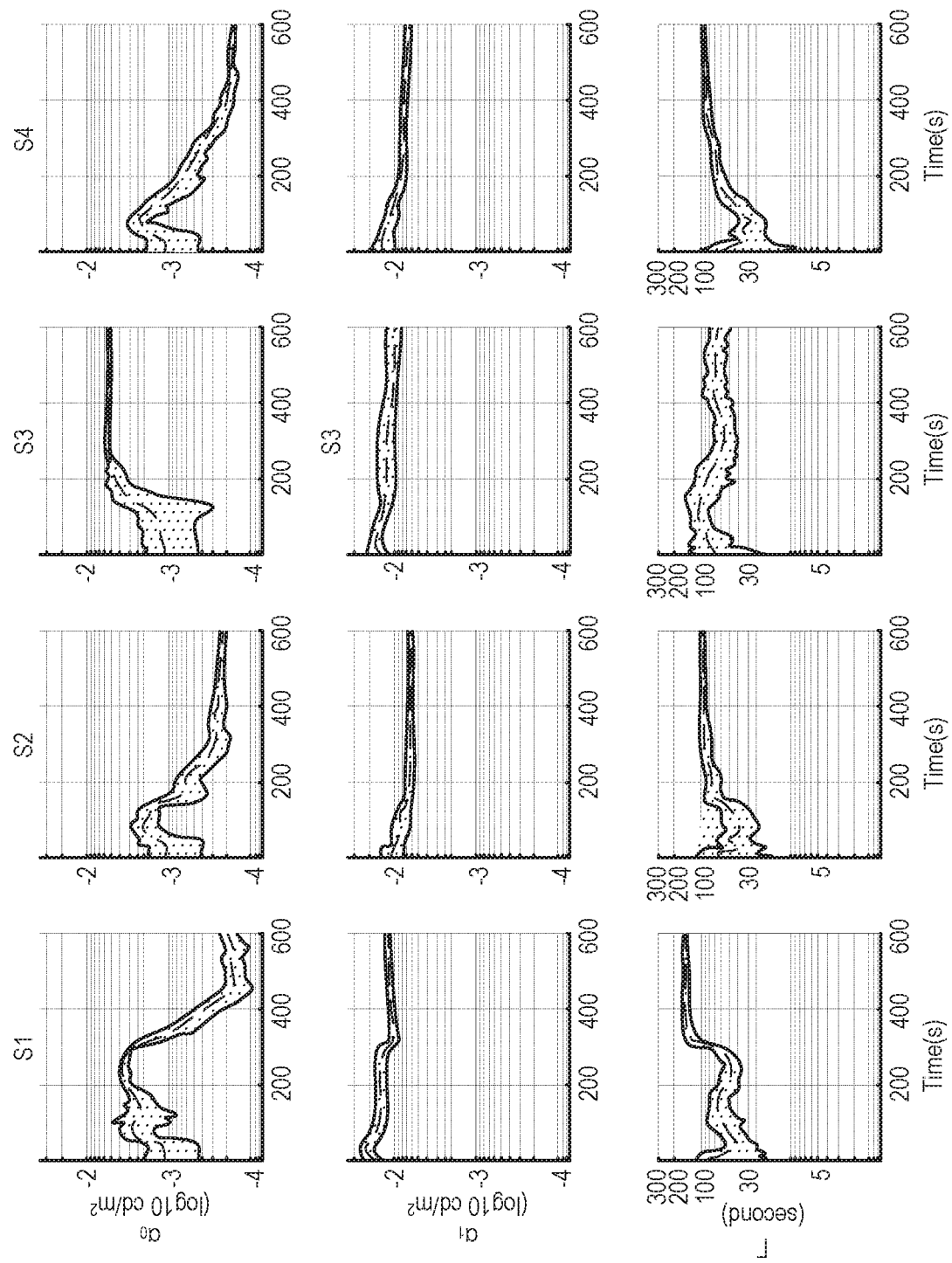
FIG. 14 depicts average trial-by-trial parameter estimates by four independent applications of a qCD method in a dark adaptation experiment.

Example Results. FIG. 14 illustrates that the average 68.2% HWCIs (shaded areas) of the marginalized joint probability density were wide in the beginning and became narrower as the experiment proceeded. Furthermore, the parameter estimates (dashed lines) changed over time.

Figure 15:
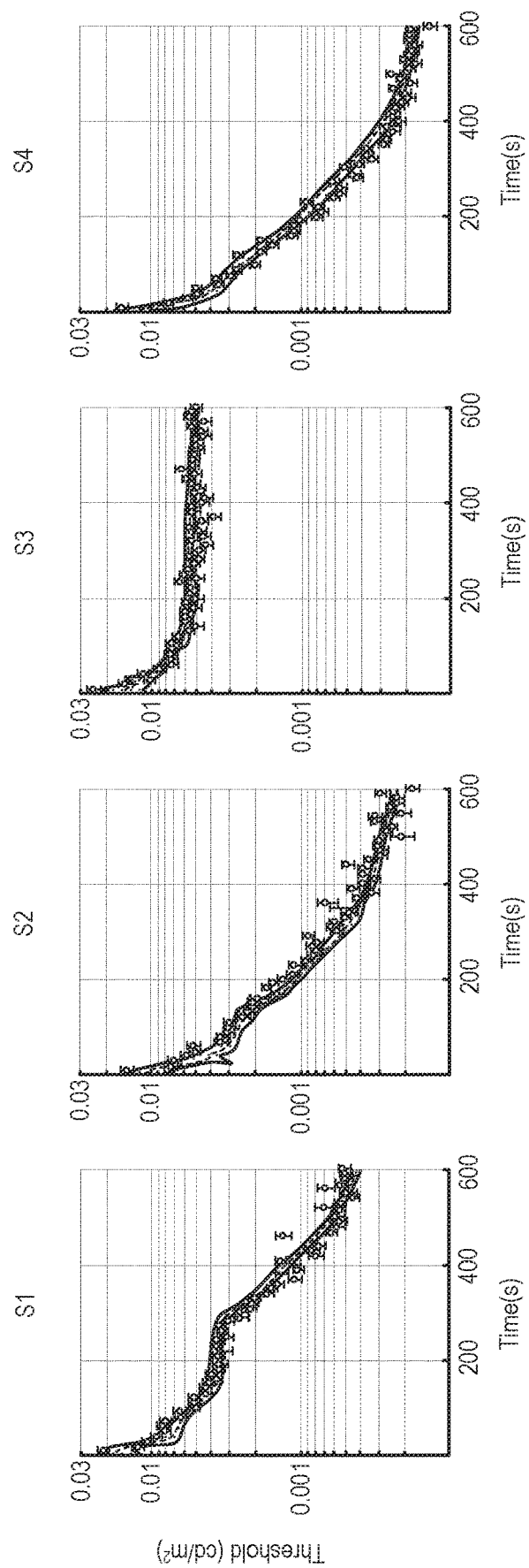
FIG. 15 depicts average trial-by-trial threshold estimates by four independent applications of a qCD method and threshold estimates by a qFC method in a dark adaptation experiment.

FIG. 15 illustrates the average trial-by-trial threshold estimates by the four independent qCD runs and the threshold estimates by all four qFC runs. The dashed lines are the estimates by qCD and the shaded areas represent the average 68.2% HWCI. The dots are the threshold estimates by qFC and the error bars are the corresponding average 68.2% HWCI. The average 68.2% HWCI of threshold estimates by the four independent qCD runs was 0.037, 0.038, 0.028 and 0.040 log 10 units for subjects S1, S2, S3, and S4, respectively. In comparison, the precision from the final posteriors of all four qFC runs was worse. The average 68.2% HWCI was 0.040, 0.043, 0.040, and 0.038 log 10 units after the 4th qFC run, for subjects S1, S2, S3, and S4, respectively.

The average RMSEs between the average trial-by-trial threshold estimates by the qCD and the threshold estimates by all four qFC runs were 0.074, 0.106, 0.057 and 0.069 log 10 units for S1, S2, S3, and S4, respectively. The correlation coefficients were 0.989, 0.984, 0.924, and 0.980 for S1, S2, S3, and S4, respectively (p<0.001 for all four subjects). These results indicate that the trial-by-trial threshold estimates by qCD were consistent with those by qFC.

Figure 16A:
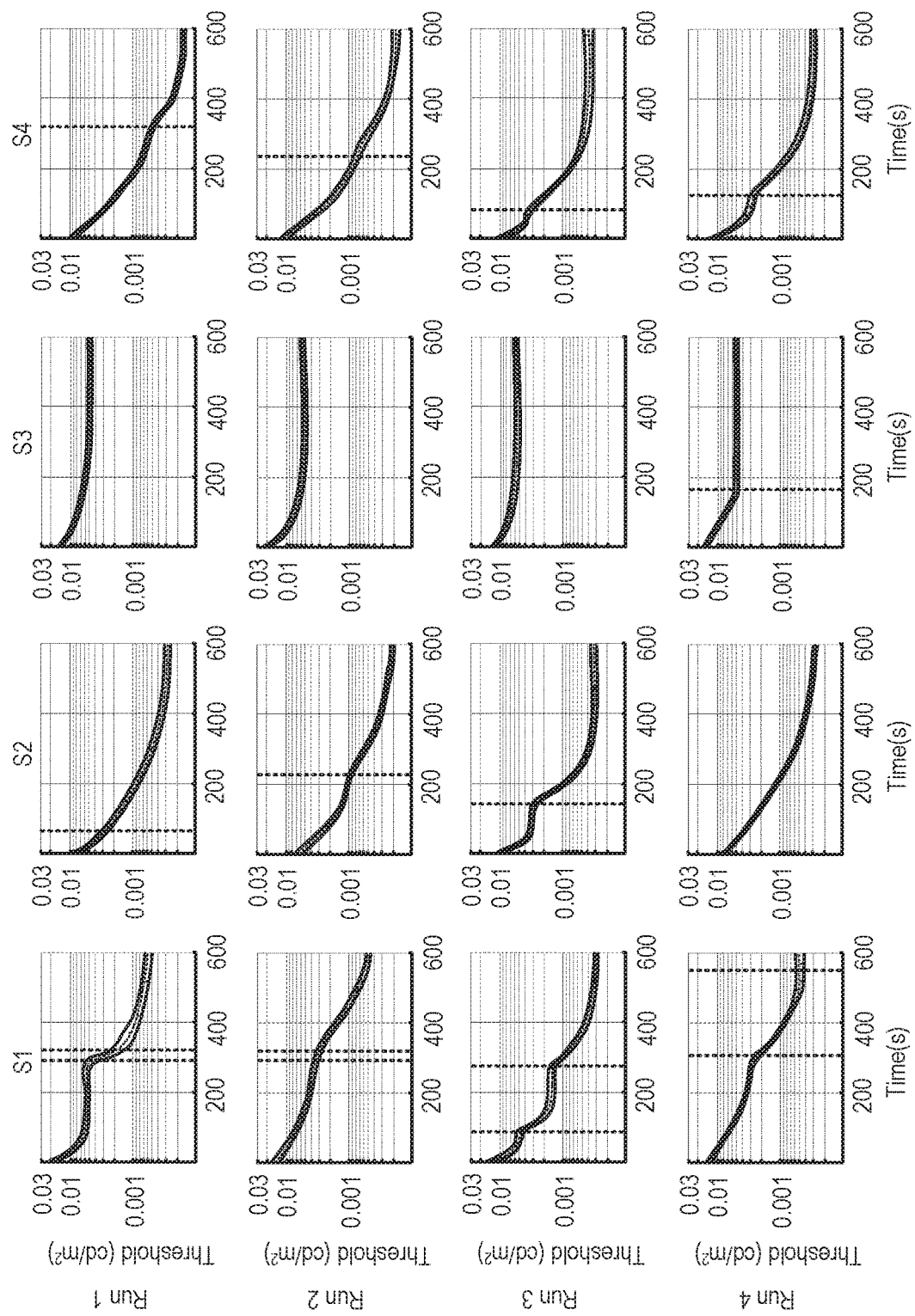
FIG. 16(a) depicts segment-by-segment threshold estimates by each application of qCD method in a dark adaptation experiment.
Figure 16B:
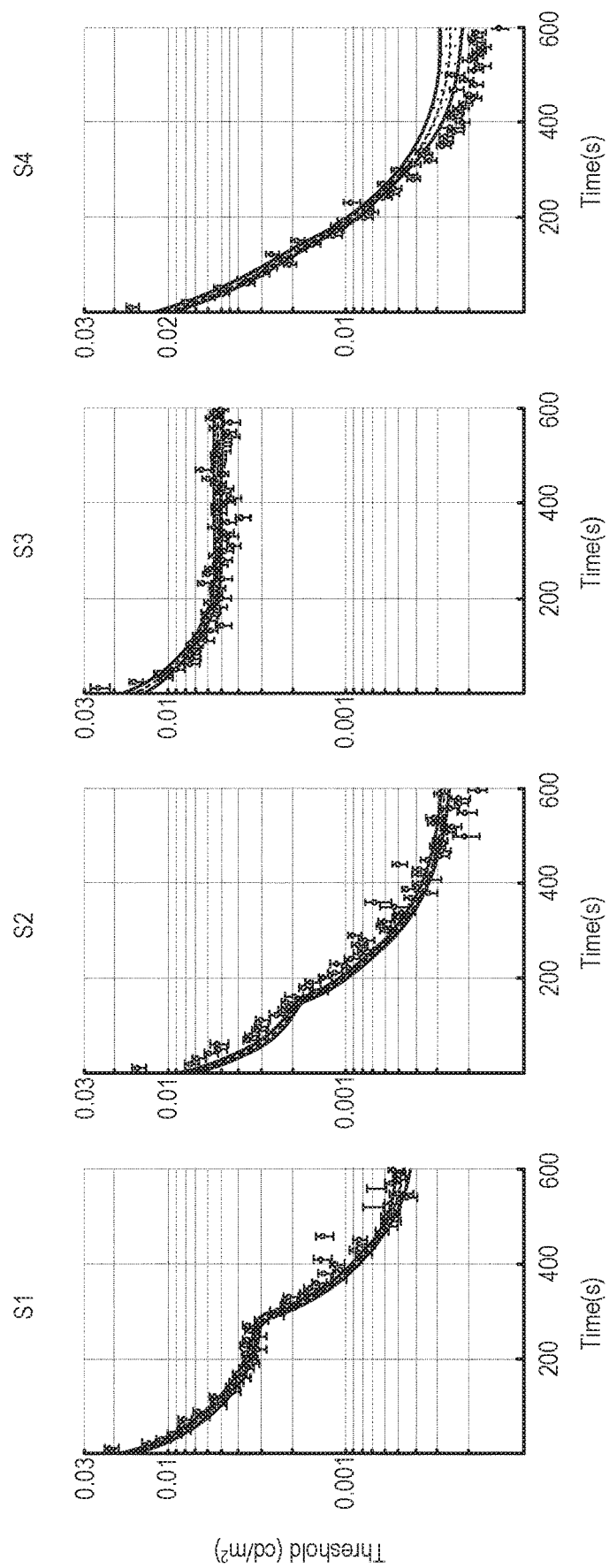
FIG. 16(b) depicts average estimated segment-by-segment dark adaptation curves by four independent applications of a qCD method and threshold estimates by a qFC method.

Using a criterion of $MD_0 = 6.58$, the number of segments of the four independent qCD runs are 3, 2, 3, and 3 for S1; 2, 2, 2, and 1 for S2; 1, 1, 1, and 2 for S3; 2, 2, 2, and 2 for S4. FIG. 16(a) illustrates segment-by-segment qCD estimates for individual runs of the four subjects. The dashed lines represent the estimates by the qCD and the shaded areas represent the average 68.2% HWCI. Different segments (if any) are separated by vertical dashed lines. FIG. 16(b) illustrates the average segment-by-segment threshold estimates of the four independent qCD runs and the threshold estimates by four qFC runs. The dashed lines represent the estimates by the qCD and the shaded areas represent the average 68.2% HWCI. The dots represent the threshold estimates by qFC and the error bars represent the average 68.2% HWCI. The average 68.2% HWCI of the segment-by-segment threshold estimates by the four qCD runs was 0.036, 0.024, 0.017 and 0.033 log 10 units for S1, S2, S3, and S4, respectively. The average RMSEs between the segment-by-segment threshold estimates by qCD and the threshold estimates by four qFC runs were 0.111, 0.124, 0.164 and 0.105 log 10 units for S1, S2, S3, and S4, respectively. The segment-by-segment threshold estimates by qCD had higher precision than the trial-by-trial estimates by qFC.

Results from both the simulations and psychophysical experiment illustrated a superiority of the qCD method over the other methods, such as the qFC method and the WS method in measuring a dark adaptation curve. A single run of the qCD method can capture the exponential decay function with high precision and no bias. Multiple qFC runs and staircase runs still cannot achieve a similar precision level, as a single qCD run. Furthermore, correction is needed to reduce the intrinsic bias in the measurement of perceptual sensitivity changing over time by any method designed to measure single static thresholds.

Example 4

Perceptual learning improves perceptual sensitivity through training. The learning curve is typically sampled in blocks of trials because of the number of trials required for each estimation. This results in imprecise and biased estimates of the learning curve, and may affect many conclusions on perceptual learning, such as the segments of learning regimes, functional form of learning, dynamic range or learning, and specificity and transfer index.

Experiment. The qCD was implemented and tested in a 4-alternative forced-choice (4AFC) global motion direction identification task. Five subjects performed 880 trials with the quick CD method interleaved with 880 trials of an SC method, with feedback. In each trial, a random dot kinematogram (RDK) moved in one of four directions (45, 135, 225, or 315 degrees), with coherence on the next trial determined by the qCD or the SC method.

Possible stimulus coherence was sampled from 0.01 to 1 with 100 equally spaced samples on a logarithmic scale. The parameter space included 50 log-linearly spaced $\alpha_0$ values equally between 0.1 and 0.4, 50 log-linearly spaced $\alpha_1$ values equally between 0.05 and 0.7, and 50 log-linearly spaced r values equally between 100 and 600 trials. For $\alpha_1$, 0 was also included to account for a constant threshold. The prior distribution, $p_0(\vec{\theta}_{PL})$, was defined by a hyperbolic secant function:

$$p_0(\vec{\theta}_{PL}) = \Pi_{a=1}^{3} \operatorname{sech}(\theta_{PL,a,confidence} \times (\log_{10}(\theta_{PL,a}) - \log_{10}(\theta_{PL,a,guess}))), \quad (54)$$

where $$\operatorname{sech}(x) = \frac{2}{e^x + e^{-x}};$$

where $\theta_{PL,a} = (\alpha_0, \alpha_1, \tau)$, for a=1, 2, and 3, respectively; $\theta_{PL,a,guess} = (0.26, 0.36, 328)$, for a=1, 2, and 3, respectively; $\theta_{PL,a,confidence} = (12.27, 5.80, 9.83)$, for a=1, 2, and 3, respectively.

Figure 17:
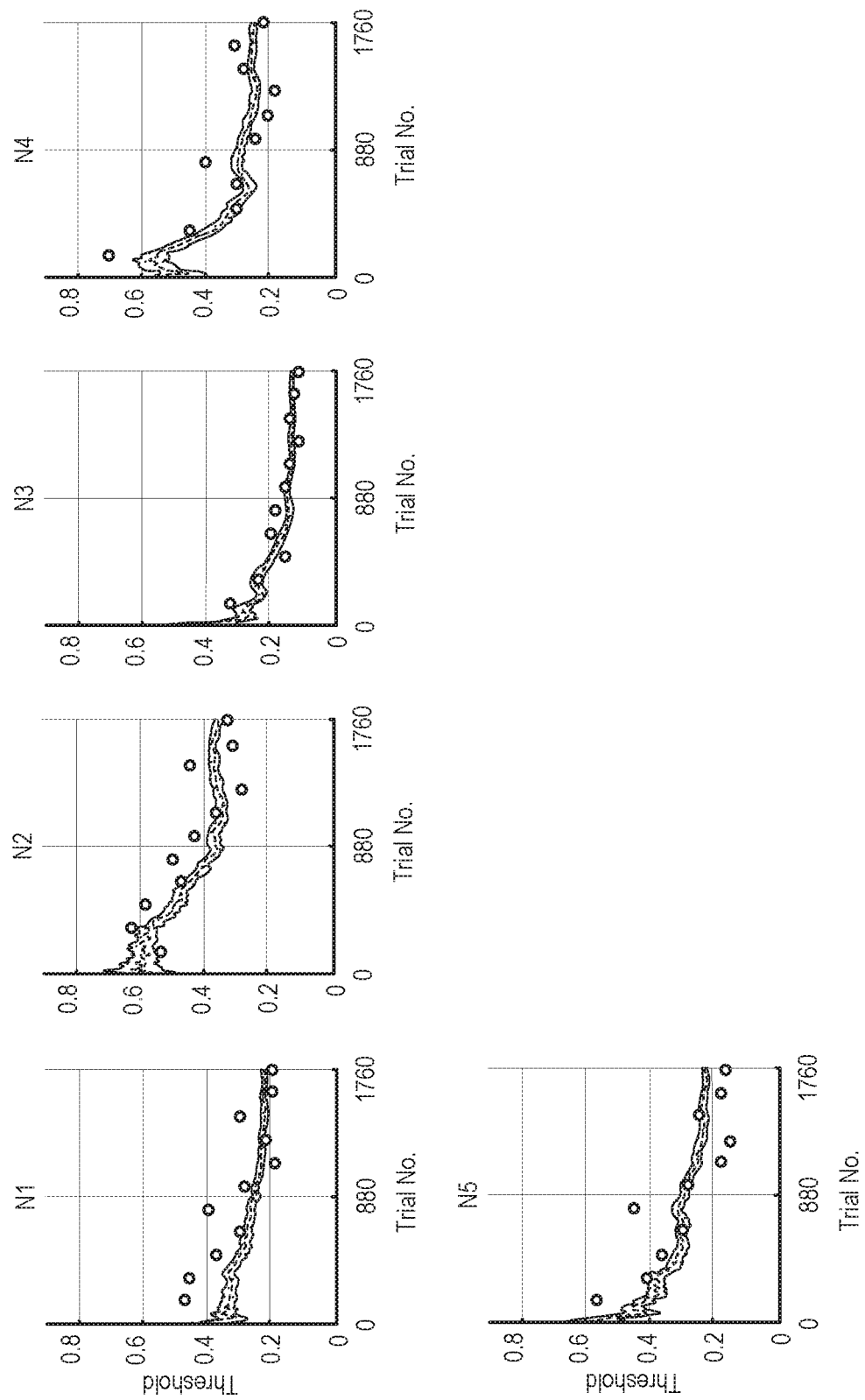
FIG. 17 depicts trial-by-trial threshold estimates by a qCD method and block threshold estimates by a 3-down/1-up staircase (SC) method in a perceptual learning experiment.

Example Results. On average, training reduced coherence thresholds by 57.3%±2.1% and 59.9%±3.0%, estimated with the qCD and SC methods, respectively. FIG. 17 illustrates the trial-by-trial threshold estimates for each subject. The dashed lines represent the estimates by the qCD, the shaded areas represent the 68.2% HWCI of the qCD, and the circles represent threshold estimates by the SC method in blocks of trials. The average 68.2% HWCI of threshold estimates was 0.023, 0.023, 0.025, 0.025, and 0.024 log 10 units for subjects N1, N2, N3, N4, and N5, respectively. Additionally, the overall estimates from the two methods matched extremely well. The average RMSEs were 0.103, 0.064, 0.070, 0.083, and 0.110 log 10 units for subjects N1, N2, N3, N4, and N5, respectively.

Figure 18:
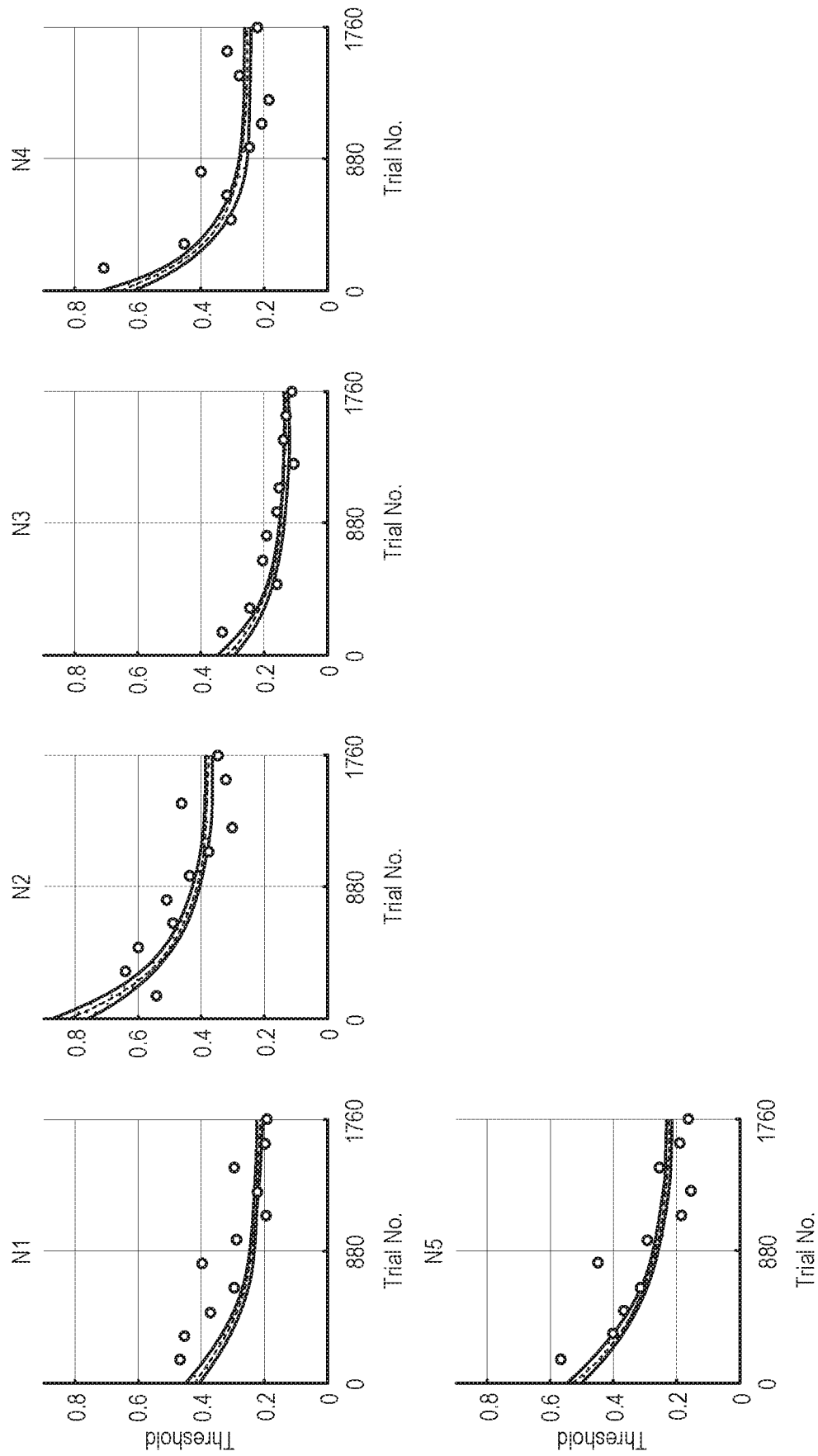
FIG. 18 depicts learning curve estimates by a qCD method and block threshold estimates by a SC method in a perceptual learning experiment.

FIG. 18 illustrates the threshold estimates of the entire learning curve as a single exponential function. The dashed lines represent the estimates by the qCD, the shaded areas represent the 68.2% HWCI of the qCD, and the circles represent threshold estimates by the SC method in blocks of trials. The averaged 68.2% HWCI estimated from the entire exponential learning curve was 0.012, 0.013, 0.013, 0.015, and 0.013 log 10 units for subjects N1, N2, N3, N4, and N5, respectively. Additionally, the overall estimates from the two methods matched extremely well. The average RMSEs were 0.108, 0.068, 0.074, 0.096, and 0.112 log 10 units for subjects N1, N2, N3, N4, and N5, respectively.

Example 5

Method. The trial-by-trail stimuli $x_{SC,n}$ and response data, $r_{SC,n}$, collected in the SC method in example 4 was rescored using the qCD method defined in (3)~(16).

Figure 19:
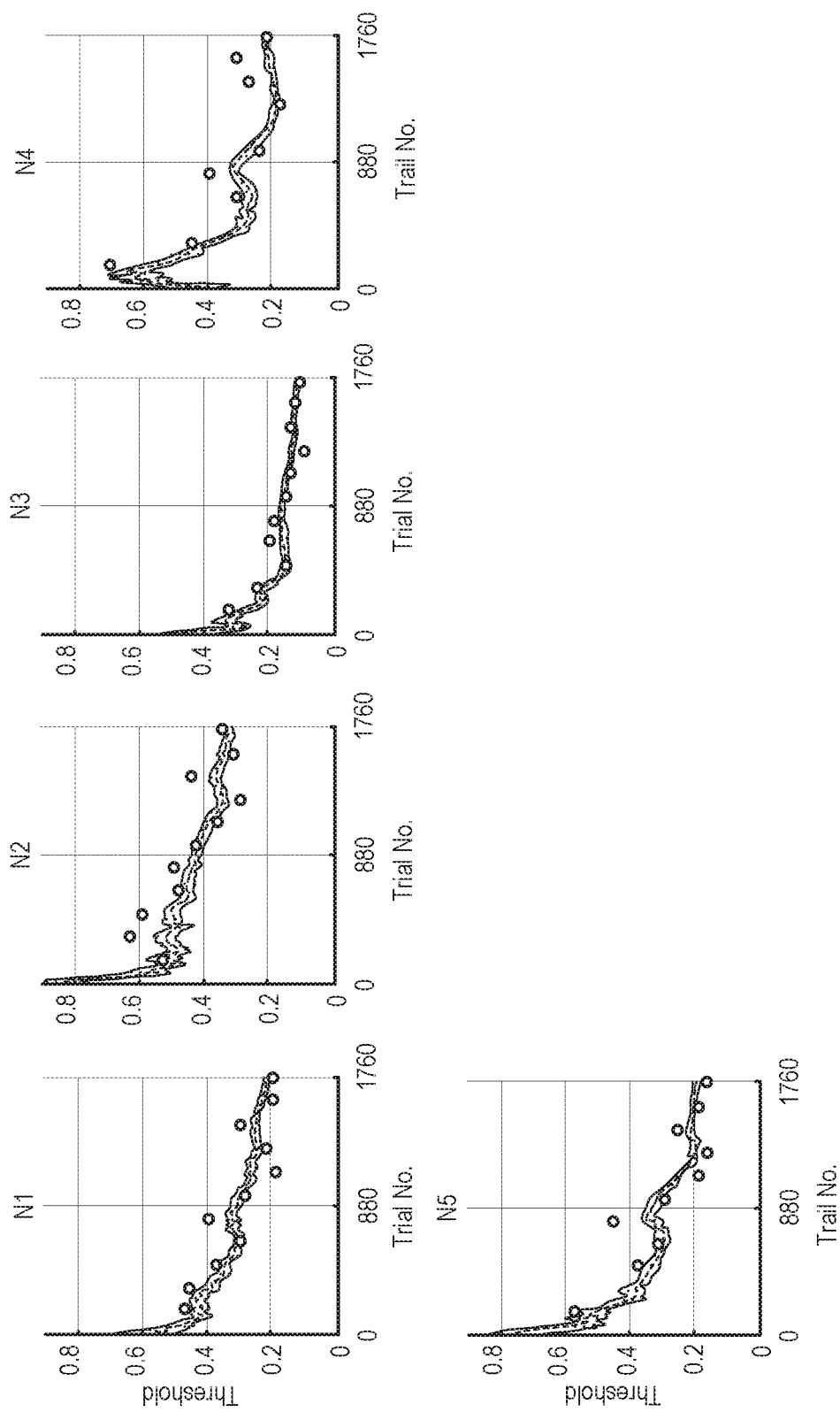
FIG. 19 depicts trial-by-trial threshold estimates based on the data from a SC method rescored by a qCD method and block threshold estimates by a SC method in a perceptual learning experiment.

Example Results. FIG. 19 illustrates the trial-by-trial threshold estimates for each subject. The dashed lines represent the estimates by the qCD method, the shaded areas represent the 68.2% HWCI of the qCD estimates, and the circles represent threshold estimates by the SC method in blocks of trials. The average 68.2% HWCI of the threshold estimates was 0.025, 0.023, 0.027, 0.029, and 0.029 log 10 units for subjects N1, N2, N3, N4, and N5, respectively. Additionally, the overall estimates from the two methods matched extremely well. The average RMSEs were 0.065, 0.051, 0.054, 0.084, and 0.072 log 10 units for subjects N1, N2, N3, N4, and N5, respectively.

Figure 20:
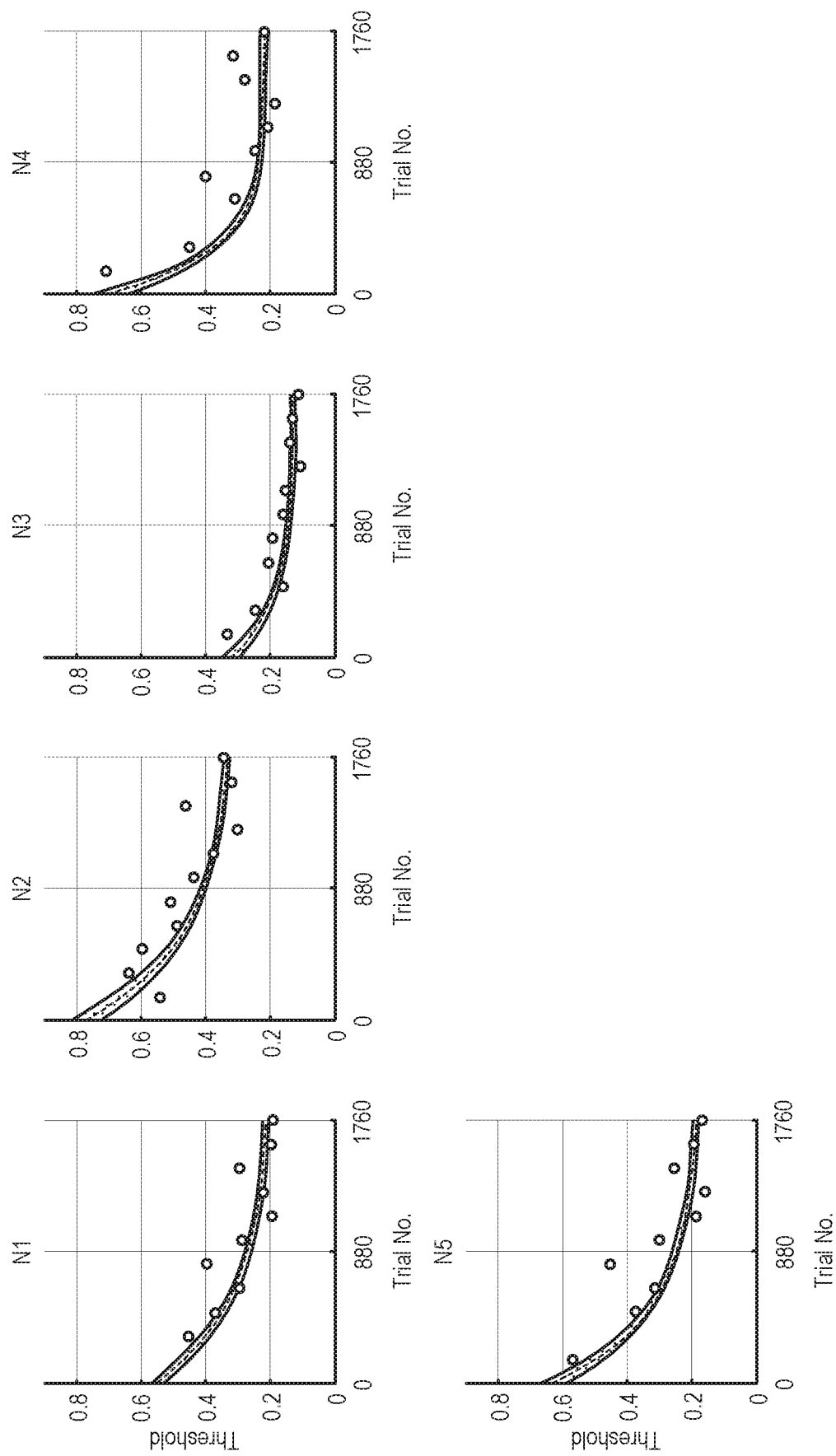
FIG. 20 depicts learning curve estimates based on the data from a SC method rescored by a qCD method and block threshold estimates by a SC method in a perceptual learning experiment.

FIG. 20 illustrates the threshold estimates of the entire learning curve with a single exponential function. The dashed lines represent the estimates by the qCD method, the shaded areas represent the 68.2% HWCI of the qCD estimates, and the circles represent threshold estimates by the SC method in blocks of trials. The averaged 68.2% HWCI estimated from the entire exponential learning curve was 0.013, 0.013, 0.015, 0.019, and 0.016 log 10 units for subjects N1, N2, N3, N4, and N5, respectively. Additionally, the overall estimates from the two methods matched extremely well. The average RMSEs were 0.072, 0.064, 0.072, 0.106, and 0.099 log 10 units for subjects N1, N2, N3, N4, and N5, respectively.

Example 6

When the functional form of the visual system (202 in FIG. 2) is unknown, a piecewise linear function could be used in the qCD method (210 and 212 in FIG. 2). The procedure can be used to access the time course of perceptual sensitivity with any possible forms. In this example, an exponential decay function was assumed as the unknown functional form of the visual system for the simulated observers in dark adaptation. However, the qCD used a piece-wise linear function to estimate the time course of perceptual sensitivity change of the observers.

Simulation. Three observers were simulated $\vec{\theta}_{i,observer} = (\alpha_0, \alpha_1, \tau)$:

$\vec{\theta}_{1,observer} = (0.000376, 0.0113, 20)$ $\vec{\theta}_{2,observer} = (0.000376, 0.0113, 45)$ $\vec{\theta}_{3,observer} = (0.000376, 0.0113, 100)$ as defined in (3).

The non-parametric qCD method is defined in (3)~(16), with $\alpha(\vec{\theta}, t)$ in (13) replaced by $\alpha(\vec{\theta}_{NP}, t_n)$:

$$\log_{10}\alpha_w(\vec{\theta}, t_n) = \log_{10}(\alpha(\vec{\theta}_{NP}, t_n)) - \frac{1}{\gamma}\log_{10}\left(\log\left(\frac{1-g}{1-p_{1.5}}\right)\right), \quad (55)$$

$$\log_{10}(\alpha(\vec{\theta}_{NP}, t_n)) = \log_{10}(b) + k(t_n - t_{n-1}), \quad (56)$$

where $\vec{\theta}_{NP} = (\theta_{NP,1}, \theta_{NP,2}) = (b,k)$, $t_n$ and $t_{n-1}$ can be an amount of time elapsed at the $n^{th}$ and $n-1^{th}$ trial since the start of a test measured in one of seconds and minutes, $\alpha(\vec{\theta}_{NP}, t)$ can be a luminance threshold corresponding to a sensitivity index of d'=1.5. The parameter space included 50 log-linearly spaced b values equally between 0.000075 and 0.037 cd/m², and 101 k values including 50 log-linearly spaced equally between $-\log_{10}(e)/5$ and $-\log_{10}(e)/200$, 0, and 50 log-linearly spaced equally between $\log_{10}(e)/200$ and $\log_{10}(e)/100$ cd/(m²×second). The prior distribution, $p_0(\vec{\theta}_{NP})$, was a uniform distribution. Possible stimulus luminance was sampled from 0.000075 to 0.075 cd/m² with 120 equally spaced samples on a logarithmic scale.

Figure 21:
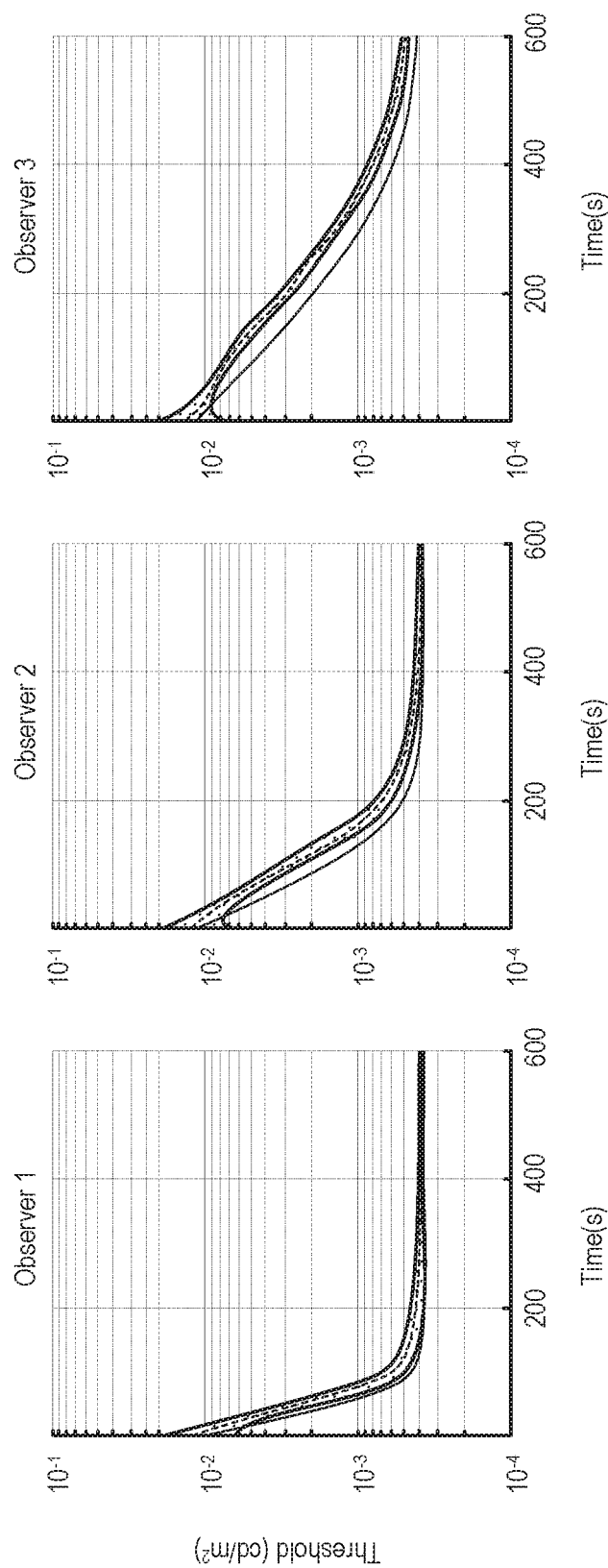
FIG. 21 depicts trial-by-trial threshold estimates for three simulated observers in non-parametric qCD simulations in a dark adaptation experiment.

Example Results. FIG. 21 illustrates the trial-by-trial threshold estimates by the non-parametric qCD for the three simulated observers. To compute the trial-by-trial threshold, the posterior distribution after each trial was used. Threshold estimates are plotted as functions of time (in seconds) elapsed since the beginning of the dark adaptation. The solid lines represent the true values of the simulated observers, the dashed lines represent the average estimates and the shaded areas represent the average 68.2% HWCI. For simulated observer 1, the average absolute bias, standard deviation, and average 68.2% HWCI of the estimated thresholds during 600-second dark adaptation was 0.052, 0.048, and 0.041 log 10 units, respectively. For simulated observer 2, the average absolute bias, standard deviation, and average 68.2% HWCI of the estimated thresholds in the 600-second dark adaptation was 0.087, 0.067, and 0.045 log 10 units, respectively. For simulated observer 3, the average absolute bias, standard deviation, and average 68.2% HWCI of the estimated thresholds in the 600-second dark adaptation was 0.131, 0.088, and 0.049 log 10 units, respectively.

As illustrated by the above examples, the qCD method accurately, precisely and efficiently can measure a time course of perceptual sensitivity change. The qCD method can have direct implications for laboratory and clinical applications. A clinician can employ the qCD method to make diagnostics, monitor a disease progression and prescribe appropriate treatments. In an example, the qCD method can be used to control delivery of a therapy to a patient. The qCD method can be used to adjust parameters, such as the frequency and dose associated with the therapy.

For example, early detection of AMD is essential for successful treatment of this type of a disease. AMD is known to adversely affect a dark adaptation of the visual system. The qCD method can be employed to measure a dark adaptation curve of the visual system. The dark adaptation curve can be evaluated to improve a diagnosis of AMD and thus a subsequent treatment of AMD. Additionally or alternatively, the qCD method can be directly applied to efficiently, accurately, and precisely quantify the time course of perceptual sensitivity changes with any functional forms in any sensory modality.

The qCD method can provide bias-free estimates of the full time course, which is especially critical in process of rapid changes in the order of seconds or/and minutes, such as dark adaptation. Furthermore, with higher precision and accuracy, the qCD method can further an understanding of the time course of other processes, which could not be measured repeatedly, such as perceptual learning. Moreover, the qCD method can be extended to simultaneously measure the time courses of multiple parameters changes over time. CSFs have been shown to describe important properties of the visual system. A quick CSF (qCSF) method, as described in U.S. Pat. No. 7,938,538, which is incorporated herein by reference, has been shown to efficiently, precisely and accurately measure static CSFs. Combining the qCD method with the qCSF method can enable not only the measurement of CSFs but also the time course of potential changes in CSFs. Given that changes in CSFs have major implications on normal aging, as well as disease states, efficient, precise and accurate measurement of changes in CSFs over time will further an understanding of the underlying mechanisms of changes in visual functions and contribute to diagnosis and/or treatment of eye diseases with known changes in CSFs.

In another example, the BMS 200 can be programmed to characterize a time course of contrast sensitivity function (CSF) changes of the visual system 202. The visual behavior modeling module 210 can be programmed to generate another perceptual sensitivity model. The other perceptual sensitivity model can include a set of behavior parameters and correspond to a changing CSF model. The set of behavior parameters can characterize a complete estimate of the time course of a behavior performance of the visual system 202. The other perceptual sensitivity model can include a four-parameter CSF and exponential decay functions of at least two of the four CSF parameters. The perceptual sensitivity model can be described by the following equations, wherein $\alpha(f, \vec{\theta}_{csf}, t)$ is the reciprocal of contrast sensitivity $S(f, \vec{\theta}_{csf}, t)$:

$$\alpha(f, \vec{\theta}_{csf}, t) = \frac{1}{s(f, \vec{\theta}_{csf}, t)}, \quad (57)$$

where $S(f, \vec{\theta}_{csf}, t)$ is a truncated log parabola with four parameters:

$$\log_{10}(S(f, \vec{\theta}_{csf}, t)) = \begin{cases} \log_{10}(g_{max}(\vec{\theta}_{csf}, t)) - \delta(\vec{\theta}_{csf}, t), \\ f < f_{max} \wedge S_0 < \log_{10}(g_{max}(\vec{\theta}_{csf}, t)) - \delta(\vec{\theta}_{csf}, t), \\ \log_{10}(S_0(f, \vec{\theta}_{csf}, t)), \quad f > f_{max} \end{cases} \quad (58)$$

$$\log_{10}(S_0(f, \vec{\theta}_{csf}, t)) = \log_{10}(g_{max}(\vec{\theta}_{csf}, t)) - \frac{4}{\log_{10}(2)}\left(\frac{\log_{10}(f) - \log_{10}(f_{max})}{\beta}\right), \quad (59)$$

$$g_{max}(\vec{\theta}_{csf}, t) = g_{max,0} + \Delta\exp(-t/\tau), \quad (60)$$

$$\delta(\vec{\theta}_{csf}, t) = \delta_0 + \Delta\exp(-t/\tau), \quad (61)$$

where $\alpha(f, \vec{\theta}_{csf}, t)$ can be a contrast threshold corresponding to a sensitivity index of d'=1.5. $\vec{\theta}_{csf} = (g_{max,0}, f_{max}, \beta, \delta_0, \Delta,$ τ) represents the four CSF parameters: peak gain $g_{max,0}$, peak spatial frequency $f_{max}$, bandwidth at half-height β (in octaves), low frequency truncation level $δ_0$, and two parameters (Δ, τ) of the exponential decay function a $g_{max}(\vec{θ}_{csf}, t)$ and $δ(\vec{θ}_{csf}, t)$. t can be an amount of time elapsed since a start of a test measured in one of seconds and minutes.

The CSF can be defined at a given performance level, d', a statistic of signal detection theory that can provide a separation between means of a signal and noise distribution, compared against a standard deviation of the noise distribution. The functional form of the CSF can assume a different formula that can have general contrast sensitivity function characteristics and the functional form of the parameter changes can assume a different formula (e.g., a power function) that can have general decay characteristics.

Initially, the set of behavior parameters of the CSF can be defined to provide prior estimate values based on the prior visual behavior data 208. The prior estimate values can be updated based on future visual behavior data associated with the visual system 202 in accordance to the methods described herein to refine the behavior model to provide a more accurate estimate of the time course of the behavior change of the visual system 202. The BMS 200 can be programmed to employ the qCD module 212 to update the set of behavior parameters of the CSF (e.g., update the estimate values) to refine the CSF based on observed visual behavior data 214 for the visual system 202 generated during a plurality of vision tests applied to the visual system 202.

In an example, the vision test can include an eight-alternative-forced-choice task (8AFC). The BMS 200 can be programmed to refine the CSF to provide a more accurate approximation of the time course of contrast sensitivity function change by iteratively updating the set of behavior parameters of the CSF based on the observed visual behavior data 222 from each application of the vision test to the visual system 202. The qCD module 212 can be programmed to update the set of behavior parameters of the CSF using a Bayesian inference. The qCD module 212 can be programmed to start with a prior probability distribution of each parameter of CSF and its temporal change parameters and update the probability distribution of each of the behavior parameters based on the observed data generated during each application of the vision test to the visual system 202.

The qCD module 212 can be programmed to characterize each behavior parameter of the set of behavior parameters by a probability density function, $p(\vec{θ}_{csf})$, to represent a relative likelihood that the value of a given parameter would equal that sample. In an example, each of the probability density functions, $p(\vec{θ}_{csf})$, are one of a uniform density function, a hyperbolic probability density function and a combination thereof. In an example, the qCD module 212 can be programmed to characterize each behavior parameter of the behavior model by a six-dimensional joint probability distribution in a parameter space. The qCD module 212 can be programmed to define a broad joint prior distribution $p_0(\vec{θ}_{csf})$ (uniform or hyperbolic) in a six-dimensional parameter space $\vec{θ}_{csf}=(g_{max,0}, f_{max}, β, δ_0, Δ, τ)$. The parameter space can represent all possible variations of the CSF function and its change over time.

The qCD module 212 can be programmed to determine multiple stimulus parameters x for each application of the vision test. The determined stimulus parameters can include a contrast threshold corresponding to a given contrast value of an optotype (e.g., grating, or filtered letter) and a spatial frequency corresponding to a given spatial frequency value of an optotype measured in cycle per degree (cpd). The vision test can be performed according to the stimulus parameters relative to the visual system 202. The vision test can be performed to provide a measure of perceptual sensitivity change of the visual system 202. The qCD module 212 can be programmed to provide the determined stimulus parameters, contrast and spatial frequency, to a visual behavior test module 216.

The visual behavior test module 216 can be programmed to control the visual stimulation system 218 to perform the vision test on the visual system 202 based on the determined stimulus parameters, and in some examples, further based on the contrast and the spatial frequency. The visual behavior test module 216 can apply the vision test according to the determined stimulus parameters to the visual system 202 by controlling the visual stimulation system 218. Thus, the visual behavior test module 216 can be programmed to control the visual stimulation system 218 to expose the visual system 202 to an optotype with a contrast and a spatial frequency specified by the stimulus parameters. In an example, the visual behavior test module 216 can be programmed to monitor for one or more responses from the observer during the vision test and store the one or more responses $r_n$, in the memory 204 as the observed visual behavior data 222. The one or more responses $r_n$ can be provided by the observer at the input device 220 based on the stimulus parameter x applied to the visual system 202. The one or more response can include one of an indication that the grating was detected, the grating was not detected and a combination thereof.

The visual behavior test module 216 can be programmed to provide the visual behavior test module 216 to the qCD module 212. The qCD module 212 can be programmed, after each application of the vision test, to update the prior distribution of the probability density functions for each of the behavior parameters of the set of behavior parameters of the CSF function to a posterior distribution based on the observed visual behavior data 222 by a Bayes' rule:

$$p_{t_n}(\vec{θ}_{csf} \mid r_n, x_n) = \frac{p_{t_n}(r_n \mid \vec{θ}_{csf}, x_n) p_{t_n}(\vec{θ}_{csf})}{p_{t_n}(r_n \mid x_n)}, \quad (62)$$

$$p_{t_n}(r_n \mid x_n) = \Sigma_{\vec{θ}_{csf}} p_{t_n}(r_n \mid \vec{θ}_{csf}, x_n) p_{t_n}(\vec{θ}_{csf}). \quad (63)$$

wherein $\vec{θ}_{csf}$ represents parameters of the CSF and its change over time, $p_{t_n}(\vec{θ}_{csf})$ is the prior probability density function of $\vec{θ}_{csf}$ of a previous application of the vision test, $p_{t(n)}(r(n)|θ,x)$ is a likelihood of observing a response (e.g., correct or incorrect) given $\vec{θ}_{csf}$ and stimulus x=(c,f), $r_n$ is the observer's response in a subsequent application of the vision test, and $p_{t_n}(\vec{θ}_{csf}|r_n, x_n)$ is the posterior distribution of $\vec{θ}_{csf}$ after the subsequent application of the vision test. Thus, a given observer's response $r_n$ to a stimulus with contrast c and spatial frequency f presented at time $t_n$ in a $n^{th}$ test (e.g., trial), the prior distribution $p_{t_n}(\vec{θ}_{csf})$ can be updated to the posterior distribution $p_{t_n}(\vec{θ}_{csf}|r_n, x_n)$ by the Bayes' rule.

The qCD module 212 can be programmed to use the posterior distribution of $n^{th}$ test as the prior of $n+1^{th}$ test:

$$p_{t_{n+1}}(\vec{\theta}_{csf}) = p_{t_n}(\vec{\theta}_{csf}|r_n, x_n). \tag{64}$$

The qCD module 212 can be programmed to compute the marginal posterior distributions of the parameters via a summation:

$$p_{t_n}(g_{max,0}|r_n, x_n) = \Sigma_{f_{max}} \Sigma_\beta \Sigma_{\delta_0} \Sigma_\Delta \Sigma_\tau p_{t_n}(\vec{\theta}_{csf}|r_n, x_n),$$

$$p_{t_n}(f_{max,0}|r_n, x_n) = \Sigma_{g_{max,0}} \Sigma_\beta \Sigma_{\delta_0} \Sigma_\Delta \Sigma_\tau p_{t_n}(\vec{\theta}_{csf}|r_n, x_n),$$

$$p_{t_n}(\beta|r_n, x_n) = \Sigma_{g_{max,0}} \Sigma_{f_{max}} \Sigma_{\delta_0} \Sigma_\Delta \Sigma_\tau p_{t_n}(\vec{\theta}_{csf}|r_n, x_n),$$

$$p_{t_n}(\delta_0|r_n, x_n) = \Sigma_{g_{max,0}} \Sigma_{f_{max}} \Sigma_\beta \Sigma_\Delta \Sigma_\tau p_{t_n}(\vec{\theta}_{csf}|r_n, x_n),$$

$$p_{t_n}(\Delta|r_n, x_n) = \Sigma_{g_{max,0}} \Sigma_{f_{max}} \Sigma_\beta \Sigma_{\delta_0} \Sigma_\tau p_{t_n}(\vec{\theta}_{csf}|r_n, x_n),$$

$$p_{t_n}(\tau|r_n, x_n) = \Sigma_{g_{max,0}} \Sigma_{f_{max}} \Sigma_\beta \Sigma_{\delta_0} \Sigma_\Delta p_{t_n}(\vec{\theta}_{csf}|r_n, x_n), \tag{65}$$

The expected mean of the marginal posterior distributions are the estimates of the parameters of the exponential decay function after the $n^{th}$ test:

$$\bar{\theta}_{csf,a,n} = \Sigma_{\theta_{csf,a}} \theta_{csf,a} p_{t_n}(\theta_{csf,a}|r_n, x_n), \tag{66}$$

where $\theta_{csf,a} = g_{max,0}, f_{max}, \beta, \delta_0, \Delta,$ and $\tau$, for $a=1, 2, 3, 4, 5$ and $6$.

To determine $p_{t_n}(\vec{\theta}_{csf}|r_n, x_n)$, the likelihood of observing a correct and incorrect response given $\vec{\theta}_{csf}$, the qCD module 212 can be programmed to determine a probability correct $p(r=1)$ psychometric function by a Weibull function:

$$p'_t(r=1|\vec{\theta}_{csf}, x) = g + (1-g)\left(1 - \exp\left(-\left(\frac{x}{\alpha_w(f, \vec{\theta}_{csf}, t)}\right)^\gamma\right)\right), \tag{67}$$

$$p_t(r=1|\vec{\theta}_{csf}, x) = (1-\lambda)p'_t(r=1|\vec{\theta}_{csf}, x) + \lambda g, \tag{68}$$

where $g=0.125$ is a guessing rate of a given AFC task, in an example, the given AFC is an 8AFC, $\gamma=3.8959$ is the slope of the psychometric function, $\lambda=0.04$ is the lapse rate and $x=(c,f)$ is the stimulus contrast and spatial frequency.

$\alpha_w(f, \vec{\theta}_{csf}, t)$ is a threshold at time t given parameter $\theta$:

$$\log_{10}\alpha_w(f, \vec{\theta}_{csf}, t) = \log_{10}(\alpha(f, \vec{\theta}_{csf}, t)) - \frac{1}{\gamma}\log_{10}\left(\log\left(\frac{1-g}{1-p_{1.5}}\right)\right), \tag{69}$$

where $p_{1.5}=0.553$ is the probability correct when $d'=1.5$ in the 8AFC task.

The probability of an incorrect response (r=0) is:

$$p_t(r=0|\vec{\theta}_{csf}, x) = 1 - p_t(r=1|\vec{\theta}_{csf}, x). \tag{70}$$

The qCD module 212 can be programmed to determine a given stimulus parameter x for each application of the vision test to the visual system 202. The qCD module 212 can be programmed to select an appropriate stimulus parameter x among a plurality of stimulus parameters x in a two-dimension stimulus space X that can cover all possible contrast $c \in C$ and spatial frequency $f \in F$ that maximizes an expected information gain about the set of behavior parameters of the decay of the contrast sensitivity function. In an example, the qCD module 212 can be programmed to perform a one-step ahead search for minimum entropy.

To determine given stimulus parameter x for an $n^{th}$ application of the vision test, the qCD module 212 can be programmed to predict the visual system's 202 response to every possible stimulus parameter x in the $n^{th}$ application of the vision test based on the current estimated posterior probability density functions of the set of parameters. The qCD module 212 can be programmed to compute the expected posterior distribution of the set of parameters for each possible combination of stimulus parameters. The stimulus parameter x among the plurality of stimulus parameters x with one of the least expected entropy is selected by the qCD module 212 for the $n^{th}$ application of the vision test. This is equivalent to maximizing the expected information gain, quantified as the entropy change between the prior and the posterior. In an example, the stimulus parameter x to be presented in the next vision test is randomly picked among the plurality of stimulus parameters x, for example with a top 10% of an expected information gain. The expected information gain of stimulus x can be defined as $l_t(x)$:

$$l_t(x) = h(\Sigma_{\vec{\theta}_{csf}} p_t(\vec{\theta}_{csf}) p_t(r=1|\vec{\theta}_{csf}, x)) - \Sigma_{\vec{\theta}_{csf}} p_t(\vec{\theta}_{csf}) h(p_t)r=1|\vec{\theta}_{csf}, x)), \tag{71}$$

$$h(p) = -p \log(p) - (1-p)\log(1-p). \tag{72}$$

The BMS 200 can be programmed for a plurality of application of the vision test to the visual system 202 to update the parameters of the probability density functions for each of the behavior parameters of the CSF and its change. The BMS 200 can update the parameters based on the observed visual behavior data 214 received by the visual behavior test module 216 during each application of the vision test to the visual system 202 by the visual stimulation system 214 according to the Bayes' rule. The BMS 200 can update the CSF to provide a more accurate representation of the time course of CSF change of the visual system 202. The BMS 200 can be programmed to update the CSF and its change according to a stopping criterion. In an example the stopping criterion is a given number of application of the vision test to the visual system 202. In another example, the stopping criterion is a precision level for a defined objective. Accordingly, by iteratively refining the behavior parameters of the probability density $p((\vec{\theta}_{csf})$, for each of the behavior parameters of the CSF based on vision test response behavior data 216 received during each application of the vision test according to the Bayes' rule, the time course of CSF change of the visual system 202 can be precisely, accurately and efficiently measured.

Example 1

Simulation. One observer was simulated $\vec{\theta}_{i,observer} = (g_{max,0}, f_{max}, \beta, \delta_0, \Delta, \tau)$:

$$\vec{\theta}_{1,observer} = (5, 3, 0.5, 4, 3, 40)$$

Performance of the qCD method was evaluated by a Monte Carlo simulation. Possible stimulus contrast was sampled from 0.002 to 1 with 128 equally spaced samples on a logarithmic scale. Possible stimulus spatial frequency was sampled from 1 to 8 cpd with 19 equally spaced samples on a logarithmic scale.

In the qCD method, parameter space included 20 log-linearly spaced $g_{max,0}$ values equally between 1 and 8, 20 log-linearly spaced $f_{max}$ values equally between 1 and 5 cpd, 20 log-linearly spaced β values equally between 0.1 and 3, 10 log-linearly spaced $\delta_0$ values equally between 1 and 3, 20 log-linearly spaced Δ values equally between 0.5 and 5, and 20 log-linearly spaced r values equally between 10 and 120 seconds. For Δ, 0 was also included to account for constant threshold.

The prior distribution, $p_0(\vec{\theta}_{csf})$, in the qCD method was defined by a hyperbolic secant function:

$$p_0(\vec{\theta}_{csf}) = \Pi_{a=1}^{6} \text{sech}(\theta_{csf,a,confidence} \times (\log_{10}(\theta_{csf,a}) - \log_{10}(\theta_{csf,a,guess})))) \quad (73)$$

where $$\text{sech}(x) = \frac{2}{e^x + e^{-x}};$$

where $\theta_{csf,a} = g_{max,0}, f_{max}, \beta, \delta_0, \Delta$, and, $\tau$, for a=1, 2, 3, 4, 5 and 6, respectively; $\theta_{csf,a,guess} = (3, 2, 0.5, 2, 1.5, 35)$, for a=1, 2, 3, 4, 5 and 6, respectively; $\theta_{csf,a,confidence} = (7.72, 9.84, 4.72, 8.20, 6.98, 6.48)$, for a=1, 2, 3, 4, 5 and 6, respectively.

Each simulated experimental run consisted of 150 trials and lasted for 300 seconds with 2-second inter-trial-interval (ITI). A simulated observer performed an 8AFC location identification task in a signal detection procedure. In each trial, a grating appeared randomly in one of eight locations on an imaginary circle. The task of the simulated observer was to identify the location where the grating appeared. The probability of a correct response was calculated response for the qCD method by the following Weibull function:

$$p'_t(r = 1 \mid \vec{\theta}_{csf}, x) = g + (1 - g)\left(1 - \exp\left(-\left(\frac{x}{\alpha_w(f, \vec{\theta}_{csf}, t)}\right)^\gamma\right)\right) \quad (74)$$

$$p_t(r = 1 \mid \vec{\theta}_{csf}, x) = (1 - \lambda)p'_t(r = 1 \mid \vec{\theta}_{csf}, x) + \lambda g, \quad (75)$$

where g=0.125 is the guessing rate of the 8AFC, γ=3.8959 is the slope of the psychometric function, λ=0.04 is the lapse rate and x=(c,f) is the stimulus contrast and spatial frequency. $\alpha_w(f, \vec{\theta}_{csf}, t)$ is the threshold at time t given parameter $\vec{\theta}_{csf}$:

$$\log_{10}\alpha_w(f, \vec{\theta}_{csf}, t) = \log_{10}(\alpha(f, \vec{\theta}_{csf}, t)) - \frac{1}{\gamma}\log_{10}\left(\log\left(\frac{1-g}{1-p_{1.5}}\right)\right), \quad (76)$$

where $p_{1.5}$=0.553 is the probability correct when d'=1.5 in the 8AFC task.

The probability of an incorrect response (r=0) is:

$$p_t(r=0 \mid \vec{\theta}_{csf}, x) = 1 - p_t(r=1 \mid \vec{\theta}_{csf}, x). \quad (77)$$

The response was simulated by drawing a random number y from a uniform distribution over the interval from 0 to 1. The response was scored as correct (r=1) if y<$p_t(r=1|_{csf}, x)$, and incorrect otherwise. In the qCD method, the joint prior distribution $p_0(\vec{\theta}_{csf})$ was updated trial-by-trial throughout one run of the 300-second experiment. The simulations were performed 100 times.

Evaluation. At each stop criterion, the accuracy and precision of the CSF estimates were evaluated at 10, 20, 50, 100, 200 and 300 seconds with 19 spatial frequencies equally spaced on a logarithmic scale between 1 and 8 cpd. Therefore, 114 contrast sensitivity estimates in 19 spatial frequencies at 6 different time points were included in calculations of the accuracy and precision at each stop criterion. Accuracy was quantified by an average absolute bias and precision was quantified by an average standard deviation and an average 68.2% half width of credible interval. Both accuracy and precision were expressed in log 10 unit.

Figure 23:
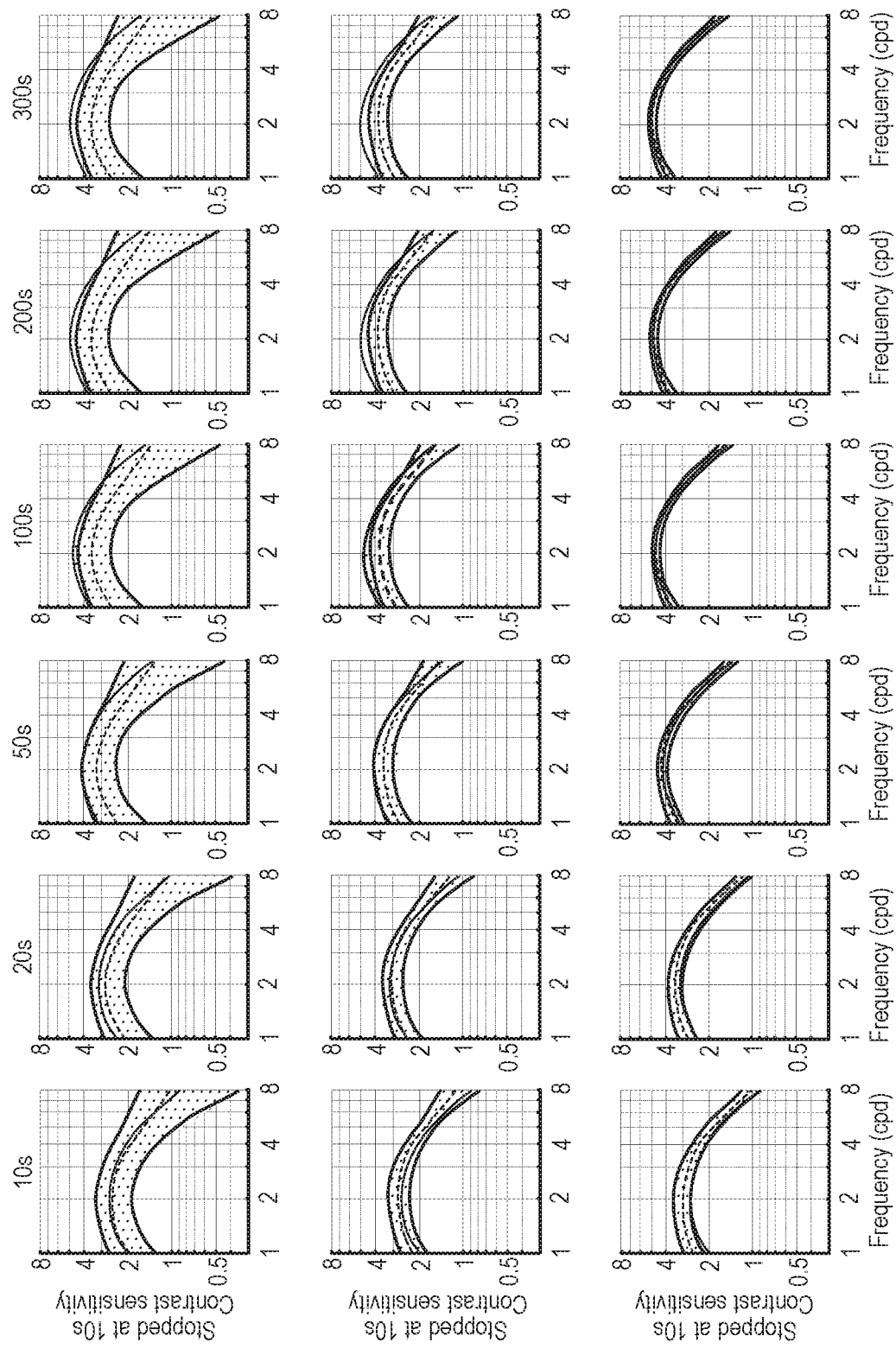
FIG. 23 depicts a history of CSFs estimated by the qCD method in a dark adaptation experiment.

Example Results. FIG. 22 illustrates a history of CSF estimated by the qCD method. The solid lines were true CSFs, dashed lines were average estimates of CSFs and shaded areas were 68.2% HWCI. Each row represented the estimates at one stop criterion and each column represented the estimates for one time point. The average absolute bias was 0.1384 log 10 units at t=0 and decreased to 0.0381 log 10 units after 300 seconds; the 68.2% HWCI was 0.1833 log 10 units at t=0 and 0.0382 log 10 units after 300 seconds; the average standard deviation 0.1219 log 10 units at t=0 and 0.0404 log 10 units after 300 seconds. The average absolute bias, the average 68.2% HWCI and the average standard deviation are summarized in Tables 1 of FIG. 23.

Additionally or alternatively, the qCD method can be used in an estimation of time course of changes in parameters in decision criterion in Yes-No task and/or in individual variability in decision. Furthermore, the qCD method can be used to estimate distribution (certainty) of changes in quantities of interests. When functional forms of the changes are unknown, non-parametric methods can be used as the first step to determine possible functional forms.

In an example, the qCD method can be based at least on informative priors, which are based on known ranges of the parameters and/or the time course of parameters. Alternatively, uniform known priors can be used when litter prior knowledge is available and/or when a categorization of subpopulations with different time course is part of a goal. In an example, prior knowledge can be integrated into the qCD method in a form of hierarchical modeling. In another example, Bayesian algorithms, such as Markov Chain Monte Carlo (MCMC), can be incorporated into the qCD method to reduce a computation time and thus maximize an information collected in a certain time period. Additionally or alternatively, global optimization algorithms, instead of one-step-ahead search, can be incorporated into the qCD method to further improve the efficiency of qCD method.

What have been described above are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A computer-implemented method comprising:
   receiving behavior data characterizing a prior behavior change of a process, wherein the process comprises a physiological process of a physiological system, wherein the behavior data characterizes a behavior change of one of electroencephalogram (EEG), Magnetoencephalography (MEG), functional magnetic resonance imaging (fMRI), functional near-infrared spectroscopy (fNIR), skin conductance, a heart rate and a release of a chemical from a body of one of an human and an animal;

generating a behavior model comprising a set of behavior parameters based on the behavior data;

determining one or more stimulus parameters for one or more performance tests based on the one or more behavior parameters;

controlling an application of the performance test to the process based on the one or more stimulus parameters to provide one or more measures of behavior change of the process;

receiving response data characterizing one or more responses associated with the process during the performance test; and updating the set of behavior parameters based on the response data to update the behavior model characterizing the behavior change of the process.

2. The computer-implemented method of claim 1, further comprising:

evaluating the behavior model after a given performance test; and generating behavior adjustment data based on the evaluation, wherein the behavior adjustment data comprises information for improving or affecting a future behavior performance of the process.

3. The computer-implemented method of claim 2, further comprising improving or affecting the future behavior performance of the process based on the generated behavior adjustment data.

4. The computer-implemented method of claim 2, further comprising rendering on a display the updated behavior model characterizing the behavior change of the process after the given performance test.

5. The computer-implemented method of claim 1, wherein the behavior model is one of a parametric behavior model, a non-parametric behavior model, and a combination thereof.

6. The computer-implemented method of claim 5, further comprising generating a prior probability density function, $p_0(\vec{\theta})$, for each combination of the behavior parameters of the behavior model, wherein the probability density function, p is one of an uninformative prior, a weakly informative prior, or an informative prior.

7. The computer-implemented method of claim 6, further comprising:

updating the prior probability density function, $p_0(\vec{\theta})$ for each combination of the parameters of the behavior model by a Bayes' rule based on the response data to generate a posterior probability density function, $p(\vec{\theta})$ for each combination of the behavior parameters of the behavior model.

8. The computer-implemented method of claim 7, wherein the Bayes' rule is defined as:

$$p_{t_n}(\vec{\theta} \mid r_n, x_n) = \frac{p_{t_n}(r_n \mid \vec{\theta}, x_n) p_{t_n}(\vec{\theta})}{p_{t_n}(r_n \mid x_n)},$$

wherein $\vec{\theta}$ represents the set of parameters of the behavior model, $p_{t_n}(\vec{\theta})$ is the prior probability density function of $\vec{\theta}$ of a given application of the performance test, $p_{t_n}(r_n \mid \vec{\theta}, x_n)$ is a likelihood of observing a desired response given $\vec{\theta}$ and stimulus $x_n$, $r_n$ is a response of the process in the given application of the performance test, and $p_{t_n}(\vec{\theta} \mid r_n, x_n)$ is the posterior distribution of $\vec{\theta}$ after the given application of the performance test.

9. The computer-implemented method of claim 7, further comprising:

determining one or more subsequent stimulus parameters to control a subsequent application of the performance test to the process based on the updated probability density function, $p(\vec{\theta})$, for each combination of the behavior parameters of the behavior model; and updating the probability density function, $p(\vec{\theta})$ for each combination of the behavior parameters of the behavior model.

10. The computer-implemented method of claim 9, wherein updating the probability density function, $p(\vec{\theta})$ for each combination of the behavior parameters of the behavior model comprises:

determining one or more corresponding stimulus parameters for each application of the performance test of a plurality of application of the performance test;

controlling each application of the performance test to the process based on the corresponding stimulus parameters; and receiving, during each application of performance test, the response data characterizing one or more responses associated with the process.

11. The computer-implemented method of claim 10, wherein the updating comprises:

refining the prior probability density function, $p_c(\vec{\theta})$ for each combination of the behavior parameters of the behavior model based on the response data of the given application of the performance test to generate the posterior probability density function, $p(\vec{\theta})$ for each combination of the behavior parameters of the behavior model; and determining the corresponding stimulus parameter(s) for the subsequent application of the performance test to the process based on the posterior probability density function, $p(\vec{\theta})$ for each combination of the behavior parameters of the behavior model.

12. The computer-implemented method of claim 11, wherein determining the corresponding parameter comprises selecting the corresponding stimulus parameter(s) among a plurality of stimulus parameters that one of maximizes and improves an expected information gain on the behavior parameters of the behavior model.

13. The computer-implemented method of claim 12, wherein the selecting of the corresponding stimulus parameter(s) is based on the posterior probability density function, $p(\vec{\theta})$, for each combination of the behavior parameters of the behavior model and based on an expected response to all possible performance tests.

14. The computer-implemented method of claim 1,
wherein the process comprises a psychophysical process of a sensory system; and
wherein the one or more behavior parameters comprises one of a response accuracy, a reaction time, a quality of choice, a perceptual sensitivity, a learning ability, an eye movement, a memorizing ability and decision making ability associated with the subject.

15. The computer-implemented method of claim 1,
wherein the process comprises a disease progression and/or evaluation of the corresponding treatment quantifiable by the behavior data; and
wherein the disease comprises one of maculopathy, cataract, glaucoma, amblyopia, myopia, dyslexia, presbyopia, schizophrenia, hearing loss, speech disorder, cerebral palsy, developmental disorder, autism, neurodegenerative disorders including one of Alzheimer's, Parkinson's, Huntington's, Amyotrophic lateral sclerosis, and multiple sclerosis.

16. A computer-implemented method comprising:
receiving behavior data characterizing a prior behavior change of a process, wherein the process comprises a psychophysical process of a natural or artificial sensory system,
wherein the behavior data characterizes one of a perception, a cognition, an emotion, a motor skill and a combination thereof of the sensory system,
wherein the perception comprises one of a vision, an audition, a taste, a tactile, an olfaction, a proprioception and a combination thereof of the sensory system,
wherein the cognition comprises one of an attention, a memory including one of working memory, short-term memory, long-term memory, a language including one of reading, speaking, writing, a learning, an executive function, a social cognition, a semantic cognition, a numerical cognition including one of mathematics, physics, and a combination thereof of the sensory system;
generating a behavior model comprising a set of behavior parameters based on the behavior data;
determining one or more stimulus parameters for one or more performance tests based on the one or more behavior parameters;
controlling an application of the performance test to the process based on the one or more stimulus parameters to provide one or more measures of behavior change of the process;
receiving response data characterizing one or more responses associated with the process during the performance test; and
updating the set of behavior parameters based on the response data to up date the behavior model characterizing the behavior change of the process.

17. A system comprising:
a non-transitory memory to store machine-readable instructions and data;
a processor to access the memory and execute the machine-readable instructions, the machine-readable instructions causing the processor to:
generate a behavior model comprising a set of behavior parameters based on behavior data characterizing a prior behavior change of a sensory system of a subject, wherein the sensory system comprises a visual system of one of a human, an animal, and an artificial intelligence system, wherein the behavior model corresponds to a perceptual sensitivity function characterizing a time course of perceptual sensitivity change of the visual system;
evaluate the perceptual sensitivity function and/or a time course of change of the perceptual sensitivity function after a given number of applications of the sensory test to the visual system to determine one of a progress of a visual disease, a progress of a treatment for the visual disease, and combinations thereof;
control an application of a sensory test to the sensory system based on one or more stimulus parameters to provide a measure of behavior change of the sensory system;
receive response data characterizing one or more responses associated with the sensory system during the sensory test;
update the set of behavior parameters based on the response data to update the behavior model characterizing the behavior change of the sensory system according to a stopping criterion;
evaluate the behavior model after a given sensory test; and
generate behavior adjustment data based on the evaluation, wherein the behavior adjustment data comprises information for improving or affecting a future behavior performance of the sensory system.

18. The system of claim 17, further comprising:
a display to render the updated behavior model characterizing the behavior change of the sensory system; and
a sensory stimulation system to apply the sensory test to the sensory system according to the one or more stimulus parameters, wherein the processor controls the stimulation system to control the application of the sensory test to the sensory system.

19. The system of claim 18, wherein the machine-readable instructions further cause the processor to generate a prior probability density function, $p_0(\vec{\theta})$, for each combination of the set of behavior parameters of the behavior model.

20. The system of claim 19, wherein the machine-readable instructions further cause the processor to update the prior probability density function, $p_0(\vec{\theta})$, for each combination of the set of behavior parameters of the behavior model by a Bayes' rule based on the response data to generate a posterior probability density function, $p(\vec{\theta})$, for each combination of the set of behavior parameters of the behavior model.

21. The system of claim 20, wherein the machine-readable instructions further cause the processor to:
determining one or more subsequent stimulus parameters to control a subsequent application of the sensory test to the sensory system based on the updated probability density function, $p(\vec{\theta})$, for each of the set of behavior parameters of the behavior model; and
updating the probability density function, $p(\vec{\theta})$, for each combination of the set of behavior parameters of the behavior model by (i) determining one or more corresponding stimulus parameters for each application of the sensory test of a plurality of application of the sensory test, (ii) controlling each application of the sensory test to the sensory system based on the one or more corresponding stimulus parameter, and (iii) receiving, during each application of sensory test, response data characterizing one or more responses of the process.

22. The system of claim 21,
wherein the behavior model corresponds to a perceptual sensitivity function characterizing a time course of perceptual sensitivity change of the visual system; and wherein the machine-readable instructions further cause the processor to determine the one or more corresponding stimulus parameters by selecting the one or more corresponding stimulus parameters among a plurality of stimulus parameters that one of maximizes and improves an expected information gain on the set of behavior parameters of the perceptual sensitivity function.

23. The system of claim 22, wherein the selecting of the one or more corresponding stimulus parameter is based on the posterior probability density function, $p(\vec{\theta})$, for each combination of the set of behavior parameters of the perceptual sensitivity function and based on the expected response to all possible sensory tests.

24. The system of claim 17,
wherein the sensory test is a vision test; and
wherein the response data characterizes one or more responses of the subject received at an input device.

25. The system of claim 17, wherein the disease is a maculopathy comprising one of age-related macular degeneration, inherited retinal disorders, retinal detachment, central serous retinopathy, diabetic retinopathy, diabetic macular edema, and choroidal neovascularization; cataract, glaucoma, amblyopia; myopia; dyslexia; schizophrenia; a neurodegenerative disorder which includes, but is not limited to Alzheimer's disease, Amyotrophic lateral sclerosis, multiple sclerosis, Huntington's disease, and Parkinson's disease.

26. The system of claim 17, wherein the machine-readable instructions further cause the processor to control delivery of a therapy to the visual system to treat the visual disease based on the evaluation of the perceptual sensitivity function.

27. A system comprising:
a non-transitory memory to store machine-readable instructions and data;
a processor to access the memory and execute the machine-readable instructions, the machine-readable instructions causing the processor to:
receive behavior data characterizing a prior behavior change of a visual system of one of a human and an animal and an artificial intelligence system;
generate a behavior model comprising a set of behavior parameters based on the behavior data, wherein the behavior model corresponds to a perceptual sensitivity function characterizing a time course of perceptual sensitivity change of the visual system;
evaluate the perceptual sensitivity function and/or a time course of change of the perceptual sensitivity function after a given number of applications of the sensory test to the visual system to determine one of a progress of a visual disease, a progress of a treatment for the visual disease, and combinations thereof;
determine one or more stimulus parameters for a vision test based on the one or more behavior parameters;
control an application of the vision test to the visual system based on the one or more stimulus parameters to provide a measure of behavior change of the visual system;
receive response data characterizing one or more responses associated with the vision system during the vision test;
update the set of behavior parameters based on the response data to update the behavior model according to a stopping criterion; and
repeat the determining, the controlling, the receiving and the updating over a plurality of vision tests to update the behavior model characterizing the time course of perceptual sensitivity change of the visual system.

* * * * *